US006087513A

United States Patent [19]
Liao et al.

[11] Patent Number: 6,087,513
[45] Date of Patent: Jul. 11, 2000

[54] EPOXIDATION PROCESS FOR ARYL ALLYL ETHERS

[75] Inventors: Zeng K. Liao, Lake Jackson; Clinton J. Boriack, Jones Creek, both of Tex.

[73] Assignee: The Dow Chemical Company, Midland, Mich.

[21] Appl. No.: 09/316,854

[22] Filed: May 21, 1999

Related U.S. Application Data

[60] Provisional application No. 60/087,169, May 29, 1999.

[51] Int. Cl.$^7$ .................................................. C07D 301/03
[52] U.S. Cl. ......................... 549/524; 549/214; 549/218; 549/529; 549/531
[58] Field of Search .................................. 549/214, 218, 549/524, 529, 531

[56] References Cited

U.S. PATENT DOCUMENTS

| 4,507,492 | 3/1985 | Woo ......................................... | 560/64 |
| 4,740,330 | 4/1988 | Wang et al. .............................. | 260/395 |
| 5,118,822 | 6/1992 | Shum et al. .............................. | 549/529 |
| 5,319,114 | 6/1994 | Gaffney et al. .......................... | 549/529 |
| 5,578,740 | 11/1996 | Au et al. .................................. | 549/525 |
| 5,633,391 | 5/1997 | Fenelli ..................................... | 549/525 |

FOREIGN PATENT DOCUMENTS

2309655 of 1997 United Kingdom .

OTHER PUBLICATIONS

Crabtree, R., *The Organometallic Chemistry of the Transition Metals*, Second Edition, John Wiley & Sons, N.Y. (1994).

Yamamoto, A., *Organotransition Metal Chemistry*, John Wiley & Sons, N.Y. (1986).

Cotton, F., and Wilkinson, G., *Advanced Inorganic Chemistry*, Fourth Edition, John Wiley & Sons, N.Y. (1980).

Britovsek, G., et al., "Novel olefin polymerization catalysts based on iron and cobalt", Chem. Commun., pp. 849–850 (1998).

Brooke, S. L., et al., "Highly Active Iron and Cobalt Catalysts for the Polymerization of Ethylene", J. Am. Chem. Soc., vol. 120, No. 16, 4049–4050 (1998).

Hitchcock, S. R., et al., "Synthesis of ansa–Titanocenes from 1,2–Bis (2–indenyl) ethane and Structural Comparisons in the Catalytic Epoxidation of Unfunctionalized Alkenes", Organometallics, vol. 14, pp. 3732–3740 (1995).

Malisisch, W., et al., "Metallosilanediols of Molybdenum and Tungsten. Synthesis and Transformation to Functionalized Metallotrisiloxanes. Hydrogen–bonded Structure of [($C_5Me_5$) $(OC)_2(Me_3P)Mo–SiMe(OH)_2$]", J. Chem. Soc., Chem. Commun., pp. 1917–1919 (1995).

Schmitzer, S., "(Hydrosilyl)tungsten Complexes of the Type $(C_5Me_5)$ $(OC)_2$ $(Me_3P)$ $W–SIR_3$ ($SIR_3=SiH_3$, $Si(H)_2Me$, $Si(H)Me_2$, $Si(H)Me$, $Si(H)(Cl)Me$, $Si(H)Cl_2$): Synthesis, Crystal Structure, and Detailed Vibrational Analysis", Inorg. Chem., vol. 32, No. 3, pp. 303–309 (1993).

Poli, R., "Open–Shell Organometallics as a Bridge between Werner–Type and Low–Valent Organometallic Complexes. The Effect of the Spin State on the Stability, Reactivity, and Structure", Chem. Rev., vol. 96, No. 6, pp. 2135–2204 (1996).

Pleune, B., et al., "Synthesis, Structure, and Protonation Studies of $Cp*MH_3$(dppe) (M=Mo, W). Pseudo–Trigonal–Prismatic vs Pseudo–Octahedral Structures for Half–Sandwich Group 6 M(IV) Derivatives", Organometallics, vol. 16, No. 8, pp. 1581–1594 (1997).

Fettinger, J. C., et al., "Stable Mononuclear, 17–Electron Molybdenum (III) Carbonyl Complexes. Synthesis, Structure, Thermal Decomposition, and Cl$^-$ Addition Reactions", J. Am. Chem. Soc., vol. 118, No. 15, pp. 3617–3625 (1996).

Abugideiri, F., et al., "Stable 16–electron, Paramagnetic Cyclopentadienylmolybenum (II) Complexes", J. Chem. Soc., Chem. Commun., pp. 2317–2318 (1994).

Herrmann, W. A., et al., "Doubly Bridged rac–Metallocenes of Zirconium and Hafnium**", Angew. Chem., Int. Ed. Engl., vol. 33, No. 19, pp. 1946–1949 (1994).

Shah, S.A., et al., "Derivatives of Group 4 metal amide chlorides and fluorides: synthesis, and characterization of novel dimethyl and fluoro–chloro complexes", J. Chem. Soc., Dalton Trans., pp. 4143–4146 (1996).

Shah, S.A., et al., "Group 4 Metal Amido Fluorides and Chlorides: Molecular Structures and the First Comparsion in Ethylene Polymerization Catalysis", Organometallics, vol. 15. No. 14, pp. 3176–3181 (1996).

Malisisch, W. et al., "$C_5R_5(OC)_2(Me_3P)M$–Substituted Silanetriols of Molybdenum and Tungsten (R=H, Me). Synthesis via Oxofunctionalization of Metallotrihydridosilanes and Transformation into the Multifunctionalized Metallotetrasiloxane $C_5Me_5(OC)_2(Me_3P)$ $WSi(OSiMe_2H)_3$·", Inorganic Chemistry, vol. 34, No. 23, pp. 5701–5702 (1995).

Loy, D. A., et al., "Bridged Polysilsesquioxanes. Highly Porous Hybrid Organic–Inorganic Materials", Chem. Rev., vol. 95, No. 5, pp. 1431–1442 (1995).

Marjoral, J. P., et al., "Dendrimers Containing Heteroatoms (Si, P, B, Ge, or Bi)", Chem. Rev., vol. 99, No. 3, pp. 845–880 (1999).

van der Waal, J. C., et al., "Zeolite titanium beta as a selective catalyst in the epoxidation of bulky alkenes", Applied Catalysis, A: General, vol. 167, pp. 331–342 (1998).

(List continued on next page.)

*Primary Examiner*—Amelia Owens

[57] ABSTRACT

A process for making an aromatic glycidyl ether epoxy compound by contacting an allyl ether made from the hydroxy moiety of a hydroxy-containing aromatic compound with an inorganic or organic hydroperoxide oxidant in the presence of a transition metal complex catalyst, wherein at least (a) the allyl ether is conformationally restricted or (b) the transition metal complex catalyst contains at least one or more stable ligands attached to the transition metal. The process of the present invention provides for epoxidizing aryl allyl ethers with high epoxidation yield (for example, greater than 70% to 90%) and high hydroperoxide selectivity (for example, greater than 70% to 90%).

106 Claims, No Drawings

OTHER PUBLICATIONS

Wang, T., et al., "Silica Supported Methyltrioxorhenium Complex Of γ–(2,2'–Dipyridyl)–Amino–Propylpolysiloxane As A Novel Catalyst For Epoxidation Of Alkenes", J. Macromolecular Science, Part A: Chem., vol. 35, No. 3, pp. 531–538 (1998).

Clark, J. et al., "Catalysis of liquid phase organic reactions using chemically modified mesophorous inorganic solids", Chem. Commun., pp. 853–860 (1998).

Camblor, M. A., et al., "Epoxidation of unsaturated fatty esters over large–pore Ti–containing molecular sieves as catalysts: important role of the hydrophobic–hydrophilic properties of the molecular sieve", Chem. Commun., pp. 795–796 (1997).

Arai, T., et al., "Syntheses of Poly (siloxane)—Supported Zirconocene Catalysts and Application to Olefin Polymerizations", J. Polymer Sci., Part A: Polymer Chemistry, vol. 36, pp. 421–428 (1998).

Bedioui, F., "Zeolite encapsulated and clay–intercalated metal porphyrin, phthalocyanine and Schiff–base complexes as models for biomimetic oxidation catalysts: an overview", Coord. Chem. Rev. vol. 144, pp. 39–68 (1995).

EPOXIDATION PROCESS FOR ARYL ALLYL ETHERS

CROSS-REFERENCE TO RELATED APPLICATION

This application claims the benefit of U.S. Provisional Application No. 60/087,169, filed May 29, 1999.

BACKGROUND OF THE INVENTION

The present invention relates to a process for epoxidizing an allyl ether of an active hydrogen-containing compound, more specifically an aryl allyl ether, by contacting the aryl allyl ether with an inorganic oxidant, more specifically aqueous hydrogen peroxide, or with an organic oxidant, more specifically an organic hydroperoxide such as an alkyl or an aromatic hydroperoxide, in the presence of a transition metal catalyst effective to form an epoxide of the aryl allyl ether.

Aryl glycidyl ethers, commercially known as epoxy resins, are manufactured successfully on a large industrial scale and are widely used in a variety of industrial and commercial sectors. Two types of reactions have heretofore been known for making the epoxy moiety of aryl glycidyl ethers. In the first type of reaction, reactive hydrogen-containing molecules, such as phenol or polyphenols, alcohols, or carboxylic acids, are reacted with epichlorohydrin, with or without catalyst(s), under basic conditions to form glycidyl ethers or glycidyl esters. The glycidyl ethers made by the first type of reaction process may have a high organic chloride content which may be deemed as undesirable in some applications, for example, in electronic applications.

In the second type of reaction, an oxidant is utilized to directly epoxidize an allyl ether or allyl ester of the corresponding reactive hydrogen-containing organo compounds, such as alcohols, phenols or carboxylic acids. Some known oxidants useful in the second type of reaction include, for example, peracetic acid, hydrogen peroxide, dimethyldioxirane, and peroxyimidic acid.

U.S. Pat. No. 5,578,740 discloses known epoxidation processes to epoxidize aryl allyl ethers. The epoxidation processes include reacting the allyl ethers with a peroxygen compound such as peracetic acid and hydrogen peroxide in the presence of catalytic system such as $Na_2WO_4/H_3PO_4/$ quaternary ammonium salt, wherein the quaternary ammonium salt is for example, trioctylmethylammonium nitrate.

Because of the cost of the above known oxidants, the side reactions of epoxidation, or the difficulty of the purification processes associated with the above allyl ether and/or allyl ester epoxidation methods, none of these epoxidation methods using oxidants heretofore known are commercially viable for the production of large volume, basic chemicals.

Another known process for the formation of an epoxide uses organic oxidants, such as an organic hydroperoxide, for making propylene oxide via oxidation of propylene in the presence of a transition metal catalyst. This reaction is limited to the epoxidation of activated or electron-rich aliphatic or cycloaliphatic alkenes such as propylene, cyclohexene, and octene-1. In this known method, including the process currently being used for making propylene oxide on a large industrial scale, the limiting amount of reagent is the oxidant, and propylene is used in substantial excess. The overall conversion of propylene to epoxide is low (for example, less than 50 percent) based on propylene used. Therefore, a separation process through fractional distillation is used to easily separate the product propylene oxide from unreacted propylene, and the unreacted propylene is then recycled to the reactor used in the epoxidation reaction process.

U.S. Pat. No. 5,118,822 issued to Shum et al., discloses a process for epoxidizing olefins, including monomeric allyl phenyl ether, to epoxide compounds by contacting the olefins with organic hydroperoxides in the presence of a rhenium oxide salt catalyst comprised of perrhenate anions and organopnicogen-containing counter cations. Shum et al., do not disclose the use of a ligand-containing catalyst and do not report a yield for phenyl glycidyl ether. It is undesirable to have such an acidic, high oxidation state, perrhenate anion since such a perrhenate anion may be a catalyst which may promote epoxide ring hydrolysis.

U.S. Pat. No. 5,319,114 discloses a process for epoxidation of olefins including phenyl allyl ether by reacting an organic hydroperoxide in the presence of a heterogeneous catalyst comprised of a carbon molecular sieve containing a transition metal oxide, such as molybdenum trioxide. In U.S. Pat. No. 5,319,114, the transition metal is entrapped on the carbon through absorption and no stable chemical bond is formed between the transition metal oxide and the carbon molecular sieve. Thus, the active form of the catalyst is molybdenum trioxide which is ineffective for providing high epoxidation yields of phenyl allyl ether. There is no yield reported for phenyl allyl ether in U.S. Pat. No. 5,319,114.

U.S. Pat. No. 5,633,391 issued to Fenelli, S. P., discloses a process for the epoxidation of olefins, including monomeric phenyl allyl ether, by contacting the olefin with bis(trimethylsilyl)peroxide as the oxidant in the presence of a rhenium oxide catalyst in an organic solvent. The conversion of phenyl allyl ether to phenyl glycidyl ether using the process disclosed by Fenelli is low (36 percent) and bis (trimethylsilyl)peroxide is expensive and not available on a commercial scale. Without the presence of an organic basic additive in the epoxidation process described in U.S. Pat. No. 5,633,391 using a rhenium catalyst, the phenyl glycidyl ether epoxide will quickly decompose and hydrolyze to a glycol.

Furthermore, it was found that a low yield of epoxidation by the catalysts disclosed in U.S. Pat. Nos. 5,118,822; 5,319,114 and 5,633,391 is obtained and therefore the processes disclosed in these patents would be difficult to apply in the epoxidation of aryl allyl ethers, because most allyl ether substrates and the epoxidation products thereof having commercial value are high boiling point compounds. Therefore, the use of the processes and catalyst systems disclosed in U.S. Pat. Nos. 5,118,822; 5,319,114 and 5,633, 391 are limited because of the difficulty in separating reactant from the product to permit reactant recycle.

Great Britain Patent No. 2,309,655 discloses a process for making heterogeneous catalysts comprised of an inorganic molecular sieve containing a transition metal useful for oxidations of alkenes, including epoxidations of alkenes, with hydrogen peroxide or an organic hydroperoxide. However, the heterogeneous catalysts claimed in GB 2,309, 655 lack selectivity which results in low epoxidation yields, therefore requiring excess olefin to be used. The heterogeneous catalysts of GB 2,309,655 are also known to be very acidic and the use of such acidic catalysts results in the ring opening hydrolysis of an epoxide product forming an undesired glycol product. Furthermore, no data is given for any type of epoxidation reaction with aryl allyl ethers in GB 2,309,655.

Therefore, it would be desirable to provide a process for epoxidizing aryl allyl ethers without the disadvantages of prior known processes, to provide high conversions of the aryl allyl ether, and to provide high yields of epoxidation with good selectivity of organic oxidant.

SUMMARY OF THE INVENTION

The present invention is directed to a process for making an aromatic glycidyl ether epoxy compound by contacting an allyl ether made from the hydroxy moiety of a hydroxy-containing aromatic compound with an inorganic or an organic hydroperoxide oxidant in the presence of a transition metal complex catalyst, wherein at least (a) the allyl ether is conformationally restricted or (b) the transition metal complex catalyst contains at least one or more stable ligands attached to the transition metal.

An objective of the present invention is to prepare the epoxy moiety(ies) of aryl glycidyl ether(s) via epoxidation of aryl allyl ether(s) by using an inorganic or an organic hydroperoxide oxidant in the presence of a group of selected transition metal complexes selected to give high conversion of the aryl allyl ether and high yield of epoxidation with good selectivity of hydroperoxide.

DETAILED DESCRIPTION OF THE INVENTION

Generally, the present invention is a process for epoxidizing an allyl ether of an active hydrogen-containing compound, more specifically for epoxidizing the aryl allyl ether, made by allylation of the oxygen atom, of a hydroxyl-containing aromatic compound, by contacting the aryl allyl ether with an inorganic or an organic oxidant, for example, aqueous hydrogen peroxide or an organic hydroperoxide, such as an alkyl or aromatic hydroperoxide, in the presence of a transition metal catalyst effective to form the epoxide of the aryl allyl ether, more specifically to produce the epoxy moiety of the aryl glycidyl ether.

The process reaction of the present invention can be generally described according to the following Scheme I:

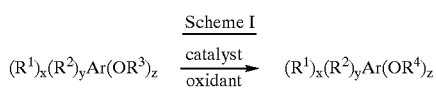

where the catalyst has the following general structure, Formula (A):

Formula (A)

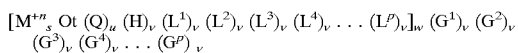

The various elements of the above reaction equation of Scheme I and the above general structure, Formula (A), of the transition metal catalyst complex are disclosed hereinafter in detail in the subheadings which follow herein.

In one embodiment of the present invention, the present invention relates to a process for making the epoxy moieties of aryl glycidyl ethers via epoxidation of aryl allyl ethers which optionally may be conformationally restricted and using an inorganic or an organic oxidant such as, for example, aqueous hydrogen peroxide or an organic hydroperoxide in the presence of a transition metal catalyst complex with the above general structure, Formula (A), which optionally may have one or more stable ligands. Therefore, high yields of epoxidation with good selectivity of the oxidant, for making glycidyl ether epoxy compounds via aryl allyl ethers as depicted in the above Scheme I reaction are achieved.

Aryl Allyl Ethers

In general, the process of the present invention is useful for epoxidizing allyl ether compounds. More particularly, the process of the present invention is suitable for epoxidizing aryl allyl ether compounds. "Aryl allyl ether compounds" or "aryl allyl ethers" as used herein means allyl ethers that contain an allyl ether moiety connected directly to an aromatic ring; or allyl ethers that contain an allyl ether moiety and an aromatic ring, but the allyl ether moiety is not connected directly to the aromatic ring, but instead the allyl ether moiety is linked to the aromatic ring via a linking group such as a polyalkylene oxide group. Typically, the aryl allyl ethers used in the present invention are made from hydroxy-containing aromatic compounds. The hydroxy moiety of the hydroxy-containing aromatic compound can be directly attached to the aromatic ring of the hydroxy-containing aromatic compound, or the hydroxy moiety may not necessarily be connected directly to the aromatic ring, but instead the hydroxy moiety may be linked to the aromatic ring via a linking group such as a polyalkylene oxide group.

The aryl allyl ethers useful in the present invention may be synthesized by reacting, for example, allyl chloride, methallyl chloride, allyl acetate, or allyl carbonate with hydroxy-containing aromatic precursor compounds with or without catalysts or with or without bases, for example, as disclosed in U.S. Pat. Nos. 5,578,740, 4,740,330 and 4,507,492.

Even more particularly, the process of the present invention is suitable for epoxidizing aryl monoallyl ethers, aryl diallyl ethers, or aryl multifunctional allyl ethers. An example of an aryl diallyl ether useful in the present invention includes the diallyl ether of bisphenol A.

In one embodiment of the present invention, the aryl allyl ethers manufactured in the present invention are conformationally restricted aryl allyl ethers. By "conformationally restricted aryl allyl ethers" it is meant that (a) the free rotation of the aromatic ring(s) of the aryl allyl ether is being restricted due to the close proximity of atoms on aromatic ring(s) adjacent to the aryl allyl ether-containing ring(s) providing a crowded spacing of the atoms which limits the mobility of the aryl allyl ether structure, for example, such as crowded spacing of atoms on adjacent aromatic rings can be found in the case of biphenol; (b) the free rotation of the aromatic rings of the aryl allyl ether is being restricted due to the presence of a rigid moiety(ies) linking aromatic ring(s) of the aryl allyl ether structure which limits the mobility of the aryl allyl ether structure, for example, such rigid moiety can be found in the case of the aromatic rings of stilbene and fluorene or in the case where the aromatic rings are linked by groups such as amide groups or ester groups; or (c) the free rotation of the aryl allyl ether group(s) on the aromatic ring(s) of the aryl allyl ether structure is being restricted due to the presence of at least one or more substituents on the aromatic ring(s) ortho to the aryl allyl ether group(s), that is, the aryl allyl ether group(s) is sterically hindered. Examples of such substituents include methyl, ethyl, isopropyl, tert-butyl, bromo, and chloro, and such groups that are partially or fully fluorinated.

It is theorized that when any one of the conformationally restricted aryl allyl ethers defined above are utilized, then deactivation of the epoxidation catalyst is impeded or prevented. It is further theorized that deactivation of an epoxidation catalyst occurs because the interaction between the epoxide from the aryl allyl ether and the transition metal will lead to the hydrolysis of the epoxide ring to form the hydrolyzed glycol. An excess of such a glycol, which is a strong ligand for the transition metal, may reduce catalyst activity by impeding the coordination of hydroperoxide to the active metal center and/or by hindering the approach of the aryl allyl ether to the catalytic site, and thus the glycol will act as a deactivator of the catalyst. However, in the present invention, it is theorized that the use of a conformationally restricted aryl ether impedes or prevents the formation of hydrolyzed glycol of an aryl glycidyl ether, which in turn, impedes or prevents deactivation of the epoxidation catalyst.

In one embodiment of the present invention, aryl allyl ethers containing alkyl, phenyl or halogen substituents on aromatic rings at the positions ortho to the aryl allyl ethers are used in the present epoxidation process described herein and may provide high aryl allyl ether conversion to epoxide (for example, in the range of from greater than 70 percent to 90 percent) and high selectivity (for example, in the range of from greater than 70 percent to 90 percent) of the organic hydroperoxide oxidant.

In another embodiment of the present invention, the aryl allyl ethers useful in the present invention are represented by but not limited to the structures of the following Formulas I–V. The following Formula I generically represents a preferred class of aryl allyl ethers used in the present invention:

Formula I

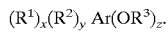

$(R^1)_x(R^2)_y \, Ar(OR^3)_z.$

In Formula I, x is from 0 to 750, y is from 0 to 750, and z is from 1 to 150.

In Formula I, Ar is a moiety containing a mononuclear aromatic ring such as phenyl. Ar may also be a moiety containing multinuclear aromatic rings, such as biphenyl, 2,2-diphenyl propane, bisphenylene oxide, tetrakis(1,1,2,2-phenyl)ethane, stilbene, phenol-formaldehyde novolac, cresol-formaldehyde novolac, phenol-dicyclopentadiene novolac, and hyper-branched aromatic phenol dendrimers. Ar may also be a moiety containing multinuclear fused aromatic rings such as naphthalene, anthracene, and naphthalene-formaldehyde novolac. Ar may also be a moiety containing multinuclear fused aromatic rings with one or more heteroatoms such as O, N, S, Si, B or P, or any combination of these heteroatoms, for example, quinoxaline, thiophene, and quinoline. Ar may also be a moiety containing mononuclear or multinuclear aromatic ring(s) fused with a cycloaliphatic ring(s) such as indane, 1,2,3,4-tetrahydronaphthalene, and fluorene. Ar may also be a moiety containing mononuclear or multinuclear aromatic ring(s) fused with a cycloaliphatic ring(s) containing one or more heteroatoms such as O, N, S, Si, B or P, or any combination of these heteroatoms, for example, chroman, indoline, and thioindane. Ar as described above in Formula I can also be partially or fully fluorinated.

In Formula I, Ar can also be a moiety containing aryl groups in which each aryl group is connected to oligomeric (for example, polymers with less than about 5000 molecular weight average) or high molecular weight (for example, greater than about 5000 molecular weight average) organosiloxane units. The aryl groups are attached directly to the Si atoms of the organosiloxane units, or the aryl groups are indirectly attached to the Si atoms of the organosiloxane units via an organic aliphatic moiety, organic cycloaliphatic moiety, organic aromatic moiety, or any combination thereof. The organic aliphatic, cycloaliphatic, or aromatic moiety should contain no more than 20 carbon atoms. When the Ar moiety contains such oligomeric or high molecular weight organosiloxane units, then z is preferably from 1 to 150.

In one embodiment of the present invention, the Ar moiety in Formula I is conformationally restricted. By "conformationally restricted" it is meant that (a) the free rotation of the allyl ether-containing aromatic ring(s) of the Ar moiety is being restricted due to the close proximity of atoms on the allyl ether-containing ring(s) of the Ar moiety to adjacent aromatic ring(s), which may or may not contain an allyl ether group(s), of the Ar moiety providing a crowded spacing of the atoms which limits the mobility of the allyl ether-containing aromatic ring(s) of the Ar moiety, such as in the case of the aromatic rings of biphenol; or (b) the free rotation of the allyl ether-containing aromatic ring(s) of the Ar moiety is being restricted due to the presence of a rigid segment(s) such as —CH=$CR^5$—, an amide group, and an ester group, linking the allyl ether-containing aromatic ring (s) to another aromatic ring(s), which may or may not contain an allyl ether group(s), of the Ar moiety which limits the mobility of the allyl ether-containing aromatic ring(s) of the Ar moiety or; (c) the free rotation of the $OR^3$ group(s) on the aromatic ring(s) of the Ar moiety is being restricted by the presence of at least one or more bulky sterically hindering $R^1$ groups other than hydrogen ortho to the $OR^3$ group (s).

In Formula I, $R^1$ is a group substituted for a hydrogen atom at a position that is ortho to the $OR^3$ group(s) on the aromatic ring(s) of the Ar moiety $R^1$ is a halogen such as bromo, and chloro; or a hydrocarbon radical such as an alkyl group, a cycloaliphatic group or aromatic group. $R^1$ is preferably an alkyl group having from 1 to 20 carbon atoms such as methyl, ethyl, or isopropyl; a cycloaliphatic group having from 3 to 20 carbon atoms such as cyclopentyl, and cyclohexyl; an aromatic group having from 6 to 20 carbon atoms such as phenyl, and naphthyl; or any combination thereof The hydrocarbon radicals above may also contain one or more heteroatoms such as O, N, S, Si, B or P, or any combination of these heteroatoms. An example of a hydrocarbon radical containing an O heteroatom is a methoxy group, an ethoxy group or a polyalkylene oxide group derived from ethylene oxide, propylene oxide, butylene oxide and cyclohexene oxide. $R^1$ as described above in Formula I can also be partially or fully fluorinated.

In one preferred embodiment, there is at least one or more $R^1$ substituents on the aromatic ring(s) of the Ar moiety in the position(s) ortho to the $OR^3$ group(s) because, in such instances, the allyl ether conversion, the epoxidation yield, and the selectivity of hydroperoxide are very high compared to those of an allyl ether without $R^1$ substituent(s) in the position(s) ortho to the $OR^3$ group(s).

In Formula I, $R^2$ is a group substituted for a hydrogen atom at a position that is not ortho to the $OR^3$ group(s) on the aromatic ring(s) of the Ar moiety. $R^2$ is a halogen such as bromo, and chloro; or a hydrocarbon radical such as an alkyl group, a cycloaliphatic group or aromatic group. $R^2$ is preferably an alkyl group having from 1 to 20 carbon atoms such as methyl, ethyl, and propyl; a cycloaliphatic group having from 3 to 20 carbon atoms such as cyclopentyl, and cyclohexyl; an aromatic group having from 6 to 20 carbon atoms such as phenyl, and naphthyl; or any combination thereof. The hydrocarbon radicals above may also contain one or more heteroatoms such as O, N, S, Si, B or P, or any combination of these heteroatoms. An example of a hydrocarbon radical containing an O heteroatom is a methoxy group, an ethoxy group or a polyalkylene oxide group derived from ethylene oxide, propylene oxide, butylene oxide and cyclohexene oxide. $R^2$ as described above in Formula I can be partially or fully fluorinated.

In Formula I, $OR^3$ is a propenyl-containing oxy group substituted for a hydrogen atom on the aromatic ring(s) of the Ar moiety, where $R^3$ preferably is a propenyl-containing moiety selected from:

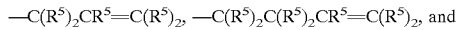

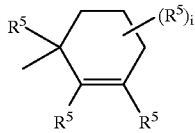

where $R^5$ is hydrogen or an alkyl group, a cycloaliphatic group or aromatic group and i is from 0 to 6. $R^5$ is preferably an alkyl group having from 1 to 20 carbon atoms such as methyl, ethyl, and propyl; a cycloaliphatic group having from 3 to 20 carbon atoms such as cyclopentyl, and cyclohexyl; an aromatic group having from 6 to 20 carbon atoms such as phenyl, and naphthyl; or any combination thereof. Each individual $R^5$ may be the same group or may be a different group from each other.

In Formula I, $R^3$ may also be a monoalkylene oxide group or a polyalkylene oxide group derived from ethylene oxide, propylene oxide, butylene oxide, or cyclohexene oxide, wherein each monoalkylene oxide group or each polyalkylene oxide group is terminated with a propenyl-containing moiety selected from:

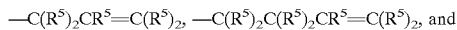

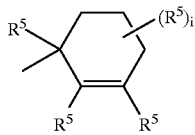

where $R^5$ is as described above.

In one embodiment, when $R^3$ in Formula I above is —$CH_2C$=$CH_2$, the ether is an "allyl ether."

In another embodiment, when $R^3$ is —$CH_2C(CH_3)$=$CH_2$ in Formula I above, the aryl ether is a "methallyl ether."

In yet another embodiment, when $R^3$ in Formula I above is

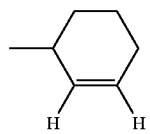

the aryl ether is a "cyclohexen-3-yl ether."

More specific and preferred examples of aryl allyl ethers useful in the present invention are represented by Formulas II–V which follow.

Examples of mononuclear aryl allyl ethers useful in the present invention are represented by the following Formula II:

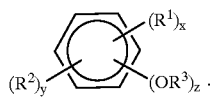

Formula II

In Formula II, R, $R^{2,}$ $OR^3$ and $R^3$ have the same meaning as described above with reference to Formula I. In Formula II, x is from 0 to 4, y is from 0 to 3, and z is from 1 to 4. Aryl allyl ethers of Formula II compound, can be prepared from aromatic hydroxyl group-containing precursors, such as, for example, 2,6-dimethylphenol; 2,6-diisopropylphenol; and 2,6-dibromophenol.

Other examples of aryl allyl ethers useful in the present invention are binuclear aryl allyl ethers which are represented by the following Formula III:

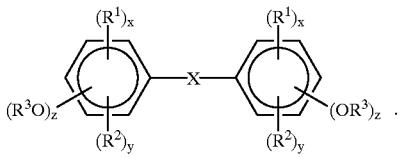

Formula III

In Formula III, $R^1$, $R^2$, $OR^3$ and $R^3$ have the same meaning as described above with reference to Formula I. In Formula III, each x is from 0 to 3, and each x can be the same or different, each y is from 0 to 3, and each y can be the same or different, and each z is from 1 to 2, and each z can be the same or different.

In Formula III, X may be nil; or X can be a heteroatom with or without substituents thereon to complete its necessary bonding valence; the heteroatom is selected from O, N, S, Si, B or P, or any combination of two or more of the above heteroatoms; X can also be, for example, —C(O)—; —S($O_2$)—; —C(O)NH—; —P(O)Ar—; an organic aliphatic moiety, with or without heteroatoms, such as, for example, oxydimethylene, methylene, 2,2-isopropylidene, isobutylene, and —$CR^5$=CH—, where $R^5$ is as defined with reference to Formula I above; a cycloaliphatic group, with or without heteroatoms, such as, for example, a cycloaliphatic ring with greater than 3 carbon atoms; or an aromatic group, with or without heteroatoms; or any combination thereof, preferably with no more than 60 carbon atoms. X as described above in Formula III can be partially or fully fluorinated, such as, for example, 2,2-perfluoroisopropylidene.

Precursors useful for making the aryl allyl ethers of Formula III include, for example, 4,4'-dihydroxybiphenyl; 3,3',5,5'-tetramethyl-4,4'-dihydroxybiphenyl; 3,3',5,5'-tetramethyl-2,2',6,6'-tetrabromo-4,4'-dihydroxybiphenyl; bis(4-hydroxyphenyl)methane; bis(4-hydroxyphenyl) sulfone; 4,4'-bis(2,6-dibromophenol)isopropylidene; 2,2'-bis(4-hydroxyphenyl)propane; bisphenol K; 9,9-bis(4-hydroxyphenyl)fluorene; 4,4'-dihydroxy-α-methylstilbene; and 1,3-bis(4-hydroxylphenyl)adamantane.

Other examples of aryl allyl ethers useful in the present invention are multinuclear aryl allyl ethers which are represented by the following Formula IV:

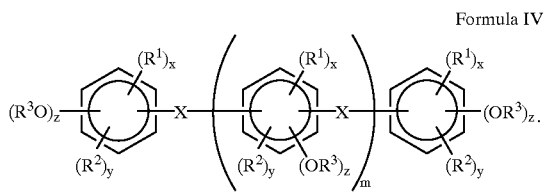

Formula IV

In Formula IV, $R^1$, $R^1$, $R^2$, $OR^3$, $R^3$, and X have the same meaning as described above with reference to Formula III. In Formula IV, each x is from 0 to 3, and each x can be the same or different, each y is from 0 to 3, and each y can be the same or different, and each z is from 1 to 2, and each z can be the same or different. In Formula IV, m is from 0.001 to 10.

Precursors useful for making the aryl allyl ethers of Formula IV include, for example, phenol-formaldehyde novolac (functionality greater than 2); o-cresol-formaldehyde novolac (functionality greater than 2); phenol-dicyclopentadienyl novolac (functionality greater than 2); and naphthol-formaldehyde novolac (functionality greater than 2).

Other examples of aryl allyl ethers useful in the present invention are multi-nuclear aryl allyl ethers which are represented by the following Formula V:

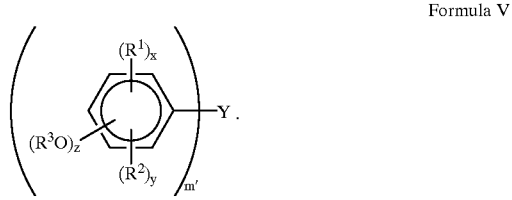

Formula V

In Formula V, $R^1$, $R^2$, $OR^3$ and $R^3$ have the same meaning as described previously with reference to Formula I. In Formula V, each x is from 0 to 3, and each x can be the same or different, each y is from 0 to 3, and each y can be the same or different, and each z is from 1 to 2, and each z can be the same or different.

In Formula V, Y is an organic aliphatic moiety, with or without heteroatoms such as O, N, S, Si, B or P, or any combination of two or more of the above heteroatoms, wherein the aliphatic moiety has from 1 to 20 carbon atoms, such as, for example, methine; a cycloaliphatic moiety, with or without heteroatoms, having from 3 to 20 carbon atoms, such as, for example, cyclohexane tri-yl; an aromatic moiety, with or without heteroatoms, such as, for example, benzenetriyl, naphthylenetriyl, fluorenetriyl; or any combination thereof, with no more than about 20 carbon atoms. Y as described above in Formula V can be partially or fully fluorinated, such as, fluoromethine.

In Formula V, m' is generally 3 or 4. However, Y may also be an oligomeric (for example, less than about 5000 molecular weight average) organosiloxane unit or high molecular weight (for example, greater than about 5000 molecular weight average) organosiloxane unit. In which case, the aryl groups are attached to the Si atoms of the organosiloxane unit directly or through an organic aliphatic, cycloaliphatic, aromatic group, or any combination thereof, with no more than about 20 carbon atoms. When Y is an oligomeric or high molecular weight organosiloxane unit, m' in Formula V is preferably from 1 to 150.

Precursors useful for making the aryl allyl ethers of Formula V include, for example, tris(4-hydroxyphenyl)methane and 1,1,2,2'-tetrakis(4-hydroxyphenyl)ethane.

In preferred embodiments of the present invention, in Formulas II to V above, there is at least one or more $R^1$ substituents on the aromatic ring(s) in the position(s) ortho to the $OR^3$ group(s) because, in such instances, the allyl ether conversion, the epoxidation yield, and the selectivity of hydroperoxide are very high compared to those of an allyl ether without $R^1$ substituent(s) in the position(s) ortho to the $OR^3$ group(s).

In other preferred embodiments of the present invention, in Formula III to V above, there is either the close proximity of atoms on aromatic ring(s) adjacent to the aryl allyl ether-containing aromatic ring(s) providing a crowded spacing of the atoms which limits the mobility of the aryl allyl ether structure; or there is the presence of a rigid moiety linking the aryl allyl ether-containing aromatic ring(s) of the aryl allyl ether structure which limits the mobility of the aryl allyl ether structure. In these instances, the allyl ether conversion, the epoxidation yield, and the selectivity of hydroperoxide are very high compared to instances wherein the aryl allyl ethers are without the effect of the crowded spacing of atoms or without the effect of a rigid moiety linking aromatic rings.

Oxidants

The oxidants useful in the present invention may be inorganic or organic hydroperoxides. Generally, the inorganic hydroperoxides used as the oxidizing agents in the process of the present invention include, for example, hydrogen peroxide. Generally, the hydrogen peroxide used is an aqueous hydrogen peroxide containing from 3 to 80 percent hydrogen peroxide by weight.

During epoxidation, the hydrogen peroxide is reduced to water. It may be necessary to remove the formed water from the reactor during the reaction in order to avoid the deactivation of the catalyst system. Water is known to be a ligand to some catalysts, and therefore, water can slow the epoxidation reaction, or water may hydrolyze and decompose the transition metal catalyst complex. Co-distillation of water with solvent by passing through a fractional distillation column will separate the water from the epoxidation reaction mixture.

Generally, the organic hydroperoxides used as the oxidizing agent in the process of the present invention may be any organic compounds having at least one hydroperoxy (—OOH) functional group. However, secondary and tertiary hydroperoxides are preferred due to the higher instability and greater safety hazards associated with primary hydroperoxides. The organic hydroperoxide used in the present invention preferably has the following general structure:

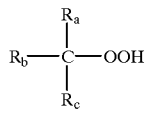

where $R_a$, $R_b$, and $R_c$ are the same or different and $R_a$, $R_b$, and $R_c$ are selected from hydrogen; an alkyl group, such as methyl or ethyl; a cycloaliphatic group, such as cyclohexyl; an aromatic group such as phenyl; or a combination thereof. A combination of two or more of $R_a$, $R_b$, and $R_c$ can also be in the same structural unit such as in the case of a pinanyl group.

Examples of organic hydroperoxides useful in the present invention include tert-butyl hydroperoxide (TBHP); tert-amyl hydroperoxide; cumene hydroperoxide; ethyl benzene hydroperoxide; cyclohexane hydroperoxide; methyl cyclohexane hydroperoxide; pinane hydroperoxide; tetrahydronaphthalene hydroperoxide; isobutyl benzene hydroperoxide; isopropyl hydroperoxide; and ethyl naphthalene hydroperoxide. It is preferred that the hydroperoxide is tert-butyl hydroperoxide or tert-amyl hydroperoxide. Mixtures of organic hydroperoxides may also be employed in the present invention.

The organic hydroperoxide may be pre-formed prior to its use by air-oxidation of a corresponding alkane or aromatic hydrocarbon. Alternatively, the organic hydroperoxide may be formed in situ. The in situ process for making organic hydroperoxide is feasible, but is generally more difficult to control than pre-forming the organic hydroperoxide.

During epoxidation, the organic hydroperoxide is reduced to an alcohol. For example, tert-butyl hydroperoxide is reduced to tert-butanol. It may be necessary to remove the formed alcohol from the reactor during the reaction in order to avoid the deactivation of the catalyst system. The alcohols are known to be ligands to some catalysts, and therefore slow the epoxidation reactions. Co-distillation of alcohol with solvent by passing through a fractional distillation column will separate the solvent, alcohol, and organic hydroperoxide. The unused organic hydroperoxide can thus be recycled into the reactors.

The organic hydroperoxide can be present in water or in an inert organic solvent, which is the same as or different from the solvent used for the epoxidation reaction when a solvent is used. In some instances, the organic hydroperoxide may contain some amount of water present with the organic hydroperoxide prior to its use. In cases where the transition metal complexes, such as $Mo(CO)_6$, are sensitive to water, the water content of the organic hydroperoxide is preferably less than about 5 percent, more preferably less than about 0.5 percent and most preferably less than about 0.05 percent. When the water content of the organic hydroperoxide is more than about 0.05 percent, it is preferred to remove the water prior to use by well known means. For example, the water may be removed from the hydroperoxide by drying the organic hydroperoxide prior to use by utilizing molecular sieves, for example, molecular sieves with 4 Å cavity size. In another embodiment, the water may be removed from the hydroperoxide by azeotropically distilling the water with a solvent(s) prior to the use of the hydroperoxide. When aqueous hydroperoxide oxidants are used, catalysts stable to hydrolysis or catalysts with hydrophobic properties are usually selected.

In a preferred embodiment, the ratio of the inorganic or organic hydroperoxide oxidant used for epoxidation to the aryl ether is preferably in the range of from 0.6 mole to 20 moles of hydroperoxide oxidant to 1 equivalent of aryl allyl ether. More preferably, the ratio of hydroperoxide oxidant used for epoxidation to the aryl ether is in the range of from 1 mole to 5 moles of hydroperoxide oxidant to 1 equivalent of aryl allyl ether. The most preferred ratio for hydroperoxide oxidant used for epoxidation to the aryl ether is from 1 mole to 2.5 moles of hydroperoxide oxidant to 1 equivalent of aryl allyl ether. One equivalent of hydroperoxide oxidant is theoretically required to oxidize one equivalent of a mono-allyl ether substrate, but it may be desirable to employ an excess of hydroperoxide oxidant to optimize conversion to the epoxide.

To carry out the reaction of the present invention, the hydroperoxide oxidant can be added into a reactor in one addition together with an aryl allyl ether such as described in Formula I to V. It is preferred to add hydroperoxide oxidant incrementally when a large amount of hydroperoxide oxidant is used. In another embodiment, the hydroperoxide oxidant can be added concurrently with an aryl allyl ether into the reactor in a continuous fashion.

Catalysts and Ligands

In general, the transition metal catalysts used in the present invention are represented by the following general structure, Formula (A):

Formula (A)

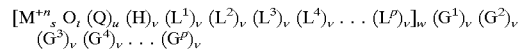

where M is a transition metal; n is the oxidation state of metal M and n is 0 or an integer from 1 to 7; s is an integer from 1 to 5;

O is oxygen such that in the above catalyst structure, Formula (A), it bonds to metal M to form a metal oxo moiety having the following structure:

M=O; M=O;

or O is oxygen such that in the above catalyst structure, Formula (A), it bonds metal M to H, or it bonds metal M to a second M to form a metal μ-oxo moiety having one of the following structures:

M—O—H or M—O—M;

or O is oxygen such that in the above catalyst structure, Formula (A), it bonds to M to form an anionic metal oxo moiety having the following structure:

M—O⁻;

and t is an integer from 0 to 3.

Q is $O_2$ wherein O is oxygen and Q is a peroxo group bonded to metal M in the above formula such that it forms a three-membered ring with one of the apexes being the metal atom M and the other two apexes being formed by the peroxo group as illustrated in the following structure:

and u is an integer from 0 to 3.

In the above catalyst structure, Formula (A), H is a hydrogen atom which is bonded to the metal atom M having the following structure:

M—H;

or H is a hydrogen which is bonded to the oxygen of a metal-μ-oxo moiety having the following structure:

M—O—H.

Each one of $L^1$, $L^2$, $L^3$, $L^4$ . . . $L^p$, in the above general catalyst structure, Formula (A), is a different ligand up to a maximum number of $L^p$ ligands; each one of $G^1$, $G^2$, $G^3$, $G^4$ . . . $G^p$ in the above general catalyst structure, Formula (A), is a different counter cation to an M—O⁻ moiety up to a maximum number of $G^p$ counter cations; v is an integer from 0 to 10; and w is an integer from 1 to 10.

In the above general catalyst structure, Formula (A), M is a transition metal. M is preferably a transition metal of $d^o$ elements, such as, Ti, Zr, V, W, Mo, Re, or Mn; or f° elements, such as, La and Ac. Preferably, the transition metal M is selected from Group IIIa, Group IVa, Group Va, Group VIa, and Group VIIa elements (previous IUPAC periodic table group notation); or from Group 3, Group 4, Group 5, Group 6, and Group 7 (new IUPAC periodic table group notation); more preferably M may be selected from elements V, Mo, W, Mn and Re. When s is greater than 1, when w is greater than 1, or when s is equal to 1 and w is greater than 1, M can be the same transition metal or the combination of two or more different transition metals.

The oxidation state n of the metal M may be from 0 to 7. The highest oxidation state of M satisfies the 18-electron rule for $d^o$ transition metal elements. For example, n is 0 for $Mo(CO)_6$. When s is 1 and t is from 0 to 3, the oxidation state n of metal M can be from 0 to 7. When the oxidation state n of metal M is at a higher oxidation state, that is, when n is 7, the metal M includes, for example, Re and Mn. When higher oxidation state metals such as Re and Mn are used in the present invention, an equivalent or slight excess (based on the metals) of basic ligands, such as, pyridine and pyrazole; or buffering agents are preferably used to reduce the acidity of these types of metal complexes so that the acidic nature of such metals does not decompose both the oxidant and the resulting epoxide product.

In the above general catalyst structure, Formula (A), v is an integer from 0 to 10 for a singular metal; and v can be the same for H, any of $L^1, L^2, L^3, L^4 \ldots L^p$, and any of $G^1, G^2, G^3, G^4 \ldots G^p$; or v can be different for H, any of $L^1, L^2, L^3, L^4 \ldots L^p$, and any of $G^1, G^2, G^3, G^4 \ldots G^p$.

Overall $O_t, (Q)_u, (H)_v, (L^1)_v, (L^2)_v, (L^3)_v, (L^4)_v \ldots (L^p)_v$ and $(G^1)_v, (G^2)_v, (G^3)_v, (G^4)_v \ldots (G^p)_v$ satisfy the bond nature of the transition metal M. For a $d^o$ element metal, the total number of electrons in the d orbital is preferred to be less than or equal to 18.

A preferred embodiment of the transition metal complex useful as catalyst in the present invention may include, for example, mono-metal complexes, and mono-metal oxo complexes, such as, for example, $Mo(CO)_6$; $MoO_2Cl_2$; $MoO_2(OC_2H_4OMe)_2$; $MoO_2$; $MoO_3$; $Cp_2MoCl_2$; $Cp*MoO_2Cl$; $Cp_2MoCl_4$; $Cp_2WCl_2$; $Cp_2ReCl_3$; $Cp*_2MoCl_2$; $CpV(CO)_4$; $Cp_2VCl_2$; $Cp*_2VOCl_2$; $Cp_2V$; $V(CO)_5$; $CH_3ReO_3$; and $Cp*Re(CO)_5Cl$; wherein Cp and Cp* above are cyclopentadienyl and pentamethylcyclopentadienyl ligands, respectively.

Another preferred embodiment of the transition metal complex useful as catalyst in the present invention may include, for example, bi-metal complexes, poly-metal complexes, bi-metal oxo complexes, poly-metal oxo complexes, and metal clusters. In such embodiment, the metal atoms may be bound to one another through metal-metal bonds, but are not required to be bound to one another. Alternatively, the metal atoms may be bound to each other through an oxygen atom such as in a metal $\mu$-oxo moiety M—O—M. The metal atoms may also be bound to each other through bidentate or multidentate ligands which include atoms, such as, sulfur atoms, nitrogen atoms, or phosphorous atoms. Bimetallic complexes or clusters and heterobimetallic complexes or clusters useful for the epoxidation of aryl allyl ethers by inorganic or organic hydroperoxides are complexes, such as, for example, $[CpMo(CO)_2]_2$; $[Cp*Mo(CO)_2]_2$; $[CpW(CO)_2]_2$; and $[Cp*W(CO)_2]_2$, where Cp is a cyclopentadienyl ligand and Cp* is a pentamethylcyclopentadienyl ligand.

Another preferred embodiment of the transition metal complex useful as a catalyst in the present invention may include transition metal complexes with peroxo structures such as peroxomolybdenum complexes for example, $MoO(O_2)L_2$, where L is hexamethylphosphorous triamide or L is picolinic acid; $(L—L)MoO(O_2)_2$, where L—L is 2-(1-octyl-3-pyrazoyl)pyridine; and $VO(O_2) (L) (H_2O)_2$ where L is picolinic acid; and diperoxo molybdenum oxo complexes, such as, for example, $MoO(O_2)L$ where L is endo,endo-3-(diphenylphosphoryl)-2-hydroxybornane. The structures of peroxo and diperoxo transition metal complexes useful in the present invention are by no means limited to those described above.

Mo, W, and Re complexes are commercially available from sources such as Aldrich Chemical Company, Inc. Typically, commercially available Mo complexes may be used as catalysts without further chemically altering their structure.

In the above general catalyst structure, Formula (A), each of the counter cations $G^1, G^2, G^3, G^4 \ldots G^p$ may be an inorganic cation of Group Ia alkali metals, such as $Na^+, K^+$, or $Cs^+$; or Group IIa alkaline earth metals, such as $Mg^{++}$, or $Ca^{++}$; or Group IIIa metals, such as $Al^{+++}$; or an organopnicogen-containing cation where the cation is comprised of at least one pnicogen, that is an element of Group IVa and at least one organic substituent bonded to the pnicogen atom. The above Groups are defined by the old IUPAC periodic table notation.

More specifically, in the above general catalyst structure, Formula (A), each of the $G^1, G^2, G^3, G^4 \ldots G^p$ is a cation moiety comprised of at least one or more quaternary cationic centers, selected from nitrogen, phosphorous, arsenic, antimony, or bismuth, with one or more organic substituents bound to each quaternary cationic center. The organic substituents may be hydrocarbons containing 1 to 20 carbon atoms selected from linear, branched or cyclic aliphatic, or aromatic, with or without heteroatoms, such as, N, P, S, O, Si, or halide atoms, such as, F, Cl, Br, and I, or the combination thereof. Examples of nitrogen-containing quaternary cationic centers having only a single cationic center useful in the present invention are tetramethyl ammonium, tetraethyl ammonium, tetraisopropyl ammonium, tetra-n-butyl ammonium, tetraisobutylammonium, tetra-n-hexyl ammonium, tetra-n-octylammonium, tetraisooctylammonium, tetraphenylammonium, benzyltrimethyl ammonium, benzyltriethylammonium, benzyltrihexylammonium, benzyltri-n-octylammonium, decyltrimetylammonium, tetradodecylammonium, hexadecyltrimethylammonium, hydroxyethyltrimethylammonium, hydroxyethyltriethylammonium, trimethoxysilylpropyltri-n-butylammonium, triethoxysilylpropyltri-n-butylammonium, trimethoxysilylpropyl-trimethylammonium, trimethoxysilylpropyltriethylammonium, octadecyldimethyltrimethoxy-silylpropylammonium, and n-tetradecyldimethyltrimethoxy-silylpropylammonium.

Examples of nitrogen-containing quaternary cationic centers having more than one cationic center useful in the present invention are, for example, N,N,N,N',N',N'-hexamethylethylenediammonium; N,N,N,N',N',N'-hexaethylethylenediammonium; N,N,N,N',N',N'-hexamethylpropylene-1,3-diammonium; and N,N,N,N',N',N'-hexaethylpropylene-1,3-diammonium.

Examples of phosphorous-containing quaternary cationic centers having a single cationic center useful in the present invention are tetramethylphosphonium, tetraethylphosphonium, tetra-n-propylphosphonium, tetraisopropylphosphonium, tetra-n-butylphosphonium, tetra-isobutylphosphonium, tetraheptylphosphonium, tetraphenylphosphonium, benzyltrimethylphosphonium, benzyltriethylphosphonium, ethyltriphenylphosphonium, ethyltritoluylphosphonium, cyclohexyltriphenylphosphonium, 2-chloroethyltriphenylphosphonium, 2-butyltriphenylphosphonium, tetrabenzylphosphonium, allyltrimethylphosphonium, allyltriphenylphosphonium, and trimethylsilylethoxyethyltriphenylphosphonium.

When an organic, inorganic or hybrid organic-inorganic oligomeric or polymeric structure contains more than one hydrocarbon substituent selected from linear, branched or cyclic aliphatic or aromatic, containing 1 to 20 carbon atoms, with or without heteroatoms, such as N, P, S, O, Si, or halide atoms, such as, F, Cl, Br, and I, or the combination thereof; and when such hydrocarbon substituents are pendant to the oligomeric or polymeric backbone and bound to a quaternary cationic center, the organic, inorganic or hybrid organic-inorganic oligomeric or polymeric structure may be linked ionically with more than one transition metal atom. In this case, the transition metal complexes are anchored or tethered to the organic, inorganic or hybrid organic-inorganic polymeric support through more than one cationic center-containing hydrocarbon substituent. An example of such a cationic center-containing hydrocarbon substituent on a polymeric support is the benzyltrimethyl-ammonium cationic group formed when cross-linked polystyrene is first chloromethylated and then aminated with trimethylamine.

When trimethoxysilyl- or triethoxysilyl-containing cationic centers, such as, for example, trimethoxysilylpropyltri-n-butylammonium; triethoxysilylpropyltri-n-butylammonium; trimethoxysilylpropyltrimethylammonium; trimethoxysilylpropyltriethylammonium; octadecyldimethyltrimethoxysilylpropylammonium; n-tetradecyldimethyltrimethoxysilylpropylammonium; and trimethylsilylethoxyethyltriphenylphosphonium; are condensed with tetraethyoxysilane then a sol-gel, silicate or zeolite having multiquaternary ammonium or quaternary phosphonium cationic centers is formed. When these quaternary cationic centers form ionic bonds with the transition metal complex, the transition metal complex is anchored or tethered to the sol-gel, silicate or zeolite. The silicate and zeolite solid support materials useful in the present invention are, for example, those with a microporous crystalline structure having a pore size similar to 4 Å type molecular sieves or those with a mesoporous crystalline structure having a pore size larger than 4 Å type molecular sieves. The zeolites, silicates, aluminophosphates, and silica aluminophosphates useful in the present invention are for example, TS-1, TS-2, ZSM-5, ZSM-11, ZSM-12, ZSM-22, AZM-48, SAPO-5, SAPO-11, zeolite X, zeolite Y, Linde type L, VPI-5, NCL-1, MCM-41, and MCM-48.

In the above general catalyst structure, Formula (A), each of the ligands $L^1, L^2, L^3, L^4 \ldots L^p$ can be either a labile, weakly bonded, neutral or basic, unidentate ligand; a strongly bonded, non-replaceable, neutral or basic, bidentate or multidentate ligand; or the combination thereof. When the ligand is a multidentate ligand, it may be bonded to the same metal atom or to two or more different metal atoms. Moreover, ligands can be linked onto an organic polymeric backbone, an inorganic polymeric backbone, or a hybrid organic-inorganic polymeric backbone. When ligands are linked in such a manner, the transition metal catalyst is anchored onto or tethered to the polymeric backbone.

When the ligands are other than part of an organic or inorganic polymer, such as, an organo siloxane or a silicate, the total number of carbon and heteroatoms in each ligand, excluding hydrogen, is generally in the range of from 1 to 100 and preferably from 5 to 100 atoms.

When the ligands are part of an organic or inorganic polymer, such as, an organo siloxane or a silicate, the total number of carbon and heteroatoms in each ligand, excluding hydrogen, is generally in the range of from 100 to 50,000 and preferably from 100 to 25,000 atoms.

The ligands in the above general catalyst structure, Formula (A), may also contain heteroatoms, such as, O, N, S, Si, B, and P or any combination of two or more of these heteroatoms. The ligands in the above general. catalyst structure, Formula (A), may also contain one or more asymmetric or chiral centers.

Yet in another preferred embodiment of the present invention, the transition metal complex catalyst contains at least one or more stable ligands attached to the transition metal. More particularly, this type of catalyst is preferably used when the aryl allyl ether is not conformationally restricted as defined above. By "stable ligand" it is meant that it is preferred that the ligand is a strongly bonded, for example, coordinatively bonded or ionically bonded, non-replaceable monodentate, bidentate or multidentate ligand; or the combination thereof which is tightly bound to the metal atom center during the epoxidation reaction.

In addition, by "stable ligand" it is meant that the ligand does not react with the oxidant, reaction additives, or epoxide product; and is not detrimentally effected by temperature, time and other reaction conditions.

A stable ligand(s) on the catalyst is desirable because it has been found that certain glycidyl ethers such as phenyl glycidyl ether, the product of epoxidizing allyl phenyl ether, may act as a metal ligand. Such type of interaction between the epoxide from aryl allyl ether and the transition metal may lead to the hydrolysis of the epoxide ring to form the hydrolyzed glycol. An excess of such a glycol, which is a strong ligand for the transition metal, may reduce catalyst activity by impeding the coordination of hydroperoxide to the active metal center and/or by hindering the approach of the aryl allyl ether to the catalytic site. Thus, the glycol in an excess amount will act as a deactivator of the catalyst.

In addition, it has surprisingly been found that when placing different substituents at the ortho positions to the allyl ether or methallyl ether groups on the aryl groups of a series of aryl allyl ethers and methallyl ethers, the size of the substituents has a dramatic effect on the aryl allyl ether conversion, the epoxidation rate, the epoxide selectivity and the organic hydroperoxide efficiency. These better results are an indication of improved catalyst activity and performance. Generally, the larger the substituents on the aromatic ring at the positions ortho to the allyl ethers and methallyl ethers, the better the epoxidation yield. For example, when placing isopropyl or bromo groups on the aryl ring at both positions on the aryl group ortho to the methallyl ether (Formula II), a greater than about 90 percent of methallyl ether epoxidation yield and TBHP selectivity are achieved.

Additionally, it has surprisingly been found that there is a dramatic effect on the aryl allyl ether conversion, the epoxidation rate, the epoxide selectivity, and the hydroperoxide efficiency when the free rotation of the allyl ether-containing aromatic rings of a difunctional aryl (meth)allyl ether is being restricted due to the close proximity of atoms on the aromatic rings adjacent to the aryl (meth)allyl ether ring. The close proximity of atoms on aromatic rings adjacent to the aryl (meth)allyl ether-containing rings provides a crowded spacing of the atoms which limits the mobility of the aryl (meth)allyl ether-containing rings, for example, such crowded spacing of atoms on adjacent aromatic rings can be found in the case of biphenol. The beneficial results of aryl allyl ether conversion, epoxidation yield, impurity reduction in the final epoxide product, and hydroperoxide efficiency are an indication of improved catalyst activity and performance.

It is theorized, without intending to be bound by such theory, that epoxidized aryl allyl ethers having large substituents in the positions ortho to the glycidyl ether groups on the aryl rings and/or having crowded spacing of the atoms on aromatic rings adjacent to the glycidyl ether-containing aromatic rings, both of which limit the mobility of the glycidyl ether groups, are unable to act as metal ligands. That is, during the catalytic epoxidation process, the glycidyl ethers cannot closely approach the transition metal atom center and form coordinating ligands. Therefore, advantageously, if the glycidyl ether cannot form a coordinating ligand with the transition metal atom center, the epoxide rings cannot be hydrolyzed to form an excess of a glycol. An excess of such a glycol, which is a strong ligand for the transition metal, may reduce catalyst activity by impeding the coordination of hydroperoxide to the active metal center and/or by hindering the approach of the aryl allyl ether to the catalytic site, thus acting as a deactivator of the catalyst.

It is therefore postulated that by introducing at least one stable ligand to the transition metal catalyst, will create conformational restriction in the form of steric hindrance around the transition metal atom(s) of the catalyst, thereby preventing the hydrolyzed glycol derivatives from approaching the transition metal atom center(s), and thus becoming strongly bound ligands and hence catalyst deactivators. It is envisioned that conformational restriction in the form of steric hindrance can also be designed around the transition metal atom(s) of the catalyst by bonding the transition metal atom(s) to stable ligand(s). At the same time, by bonding the transition metal atom(s) to stable ligand(s) the electronic nature of the transition metal atom(s) of the catalyst can be varied to enhance the catalytic reactivity of the transition metal catalyst complex useful in the present invention. Varying the steric nature and the electronic nature of stable ligands may be done according to the teachings by Crabtree, R. in *The Organometallic Chemistry of the Transition Metals,* Second Edit., John Wiley & Sons, N.Y. (1994); by Yamamoto, A., in *Organotransition Metal Chemistry,* John Wiley & Sons, N.Y. (1986); and by Cotton, F. and Wilkinson, G., in *Advanced Inorganic Chemistry,* Fourth Edition, John Wiley & Sons, N.Y. (1980).

The stable ligands $L^1$, $L^2$, $L^3$, $L^4$ . . . $L^p$ useful in the present invention for the design of sterically hindered transition metal complexes include, for example, non-replaceable, stable, neutral, monodentate ligands, bidentate ligands, multidentate ligands, or the combination thereof, or polymeric organic or inorganic multidentate ligands; non-replaceable or strongly bonded, anionic monodentate ligands, bidentate ligands, multidentate ligands, or the combination thereof, or polymeric organic or inorganic multidentate ligands.

While it is desired to have one or more stable ligands attached to the transition metal to create sterically hindered complexes, it is also preferred that there is one or more labile ligands or one or more than one vacant coordination sites on the transition metal to allow for the insertion of the hydrogen peroxide or organic hydroperoxide onto the transition metal in order to activate the hydroperoxide to carry on the epoxidation process.

In one embodiment of the present invention, stable ligands useful in the present invention include, for example, the oxygen-containing ligands, the phosphorous-containing ligands, the nitrogen-containing ligands, the aromatic moiety-containing ligands, organosilyl- or organosilyloxy-containing ligands, or combinations thereof. These stable ligands may also contain one or more asymmetric or chiral centers. These stable ligands may also contain one or more hydrophilic moieties such as, for example, but not limited to, sodium sulfonate moiety.

The ligands, including stable ligands, which may be useful in the present invention include, but are not limited to, the following representative ligands:

Oxygen-Containing Ligands

Monodentate, bidentate or polydentate oxygen-containing ligands useful in the present invention include, but are not limited to, for example, aliphatic and cycloaliphatic alcohols and diols; phenolates; carboxylic acids; ketones or the combination of these oxygen-containing ligands. Partially or fully fluorinated monodentate or polydentate oxygen-containing ligands are also included herein as examples useful in the present invention.

Examples of oxygen-containing ligands useful in the present invention are alcohols and diols, such as ethanol; propanol; cyclohexanol; diethyleneglycol monomethylether; propane-1,2-diol; cis- and trans-cyclohexane-1,2-diol; 2,3-dimethylbutane-2,3-diol; octane-1,2-diol; and diethyleneglycol. Also included herein as examples of oxygen-containing ligands useful in the present invention are fluorinated alcohols such as trifluoroethanol; 1,3-difluoro-2-propanol; 2,2,3,3,3-pentafluoro-1-propanol; and hexafluoroisopropanol. Also included herein as examples of oxygen-containing ligands useful in the present invention are carboxylic acids and carboxylic acid esters containing a hydroxy group, such as lactic acid; and ethyl lactate; ketones such as acetoacetate; and acetoacetone; phenolate or bisphenolato ligands such as, for example, 2,6-dimethyl-, 2,6-di-tert-butyl- or 2,6-diisopropyl phenol; 2,2'-methylenebis(6-tert-butyl-4-methylphenol); 2,2'-ethylenebis(6-tert-butyl-4-methylphenol); 1,1'-binaphthyl-2,2'-diol; methylene-1,1'-binaphthyl-2,2'-diol; and 2,2'-thiobis(6-tert-butyl-4-methylphenol); but the present invention is not limited to these ligand structures.

A strongly bonded, non-replaceable, neutral or basic, bidentate or multidentate ligand is usually a more stable ligand than a monodentate ligand. Stable ligands containing oxygen useful in the present invention include, for example, aliphatic and cycloaliphatic diols, bisphenolates, dicarboxylic acids, diketones, or the combination thereof. Such stable ligands useful in the present invention include but are not limited to, for example, propane-1,2-diol; cis- and trans-cyclohexane-1,2-diol; 2,3-dimethylbutane-2,3-diol; octane-1,2-diol; diethyleneglycol; 2,2'-methylenebis(6-tert-butyl-4-methylphenol); 2,2'-ethylenebis(6-tert-butyl-4-methylphenol); 1,1'-binaphthyl-2,2'-diol; methylene-1,1'-binaphthyl-2,2'-diol; and 2,2'-thiobis(6-tert-butyl-4-methylphenol); tartaric acid; cis-, or trans-1,2-cyclohexane dicarboxylic acid; acetoacetate; and acetoacetone.

The oxygen-containing ligands may also contain one or more asymmetric or chiral centers. Such asymmetric or chiral oxygen-containing ligands include, but are not limited to, for example, 1-(S)-2-(R)-(+)- or 1-(R)-2-(S)-(−)-trans-2-phenylcyclohexanol; (S)-(+)- or (R)-(−)-3-hydroxytetrahydrofuran; S-(−)- or R-(+)-alpha-methyl-1-naphthalenemethanol; S-(−)- or R-(+)-alpha-methyl-2-naphthalenemethanol; S-(+)- or R-(−)-propanediol; S-(+)- or R-(−)-3-chloro-1,2-propanediol; (S)-(+)- or R-(−)-1,3-butanediol; (2S,3S)-(+)- or (2R,3R)-(−)-2,3-butanediol; (2S,4S)-(+)- or (2R,4R)-(−)-2,4-pentanediol; (1S,2S,3R,5S)-(+)- or (1R,2R,3S,5R)-(−)-pinanediol; (1S,2S)-trans- or (1R,2R)-trans-1,2-cyclohexanediol; (1S,2S)-trans- or (1R,2R)- trans-1,2-cyclopentanediol; D-xylonic gamma-lactone; D-ribonic gamma-lactone; L- or D-xylose; L- or D-arabinose; L- or D-ribose; L- or D-threitol; L- or D-arabitol; L- or D-flucose; 2-deoxy-D-ribose; D-xylopyranoside; D-fucose; 2-deoxy-D-glucose; 5-thio-D-glucose; L-glucose; methyl-S-(+)- or R-(−)-lactate; diethyl-L- or D-tartrate; diisopropyl-L- or D-tartrate; S-(−)- or R-(+)-1,1'-bi-2-naphthol; and 2S,3S-(−)- or 2R,3R-(+)-1,4-dibenzyloxy-2,3-butanediol.

Partially or fully fluorinated bidentate or polydentate oxygen-containing ligands are also included herein as examples useful in the present invention.

The above-described stable oxygen-containing ligands are useful for designing transition metal complexes for epoxidation of aryl allyl ethers.

Phosphorous-Containing Ligands

Monodentate, bidentate or polydentate phosphorous-containing ligands useful in the present invention include, for example, inorganic or organic phosphoric and phosphorous acid derivatives, aliphatic, cycloaliphatic or aromatic organophosphinyl ligands. Partially or fully fluorinated monodentate or polydentate phosphorous-containing ligands are also included herein as examples useful in the present invention.

Examples of monodentate, bidentate or polydentate phosphorous-containing ligands useful in the present invention include but are not limited to, for example, trimethylphosphine; triethylphosphine; triisopropylphosphine; triphenylphosphine; tricyclohexylphosphine; cyclopentadienyldiphenylphosphine; methyldiphenylphosphine; or any combination of these phosphorous-containing ligands. Also included herein as examples of phosphorous-containing ligands useful in the present invention are 1,2-bis(diphenylphosphino)-ethane; 1,3-bis(diphenylphosphino) propane; 1,4-bis(diphenylphosphino)butane; 1-(1-diphenylphosphinoferrocenyl)-1-dicyclohexylphosphinyl ethane; 2-(diphenylphosphinyl)-cyclohexanol; 2,2'-bis(diphenylphosphino)-1,1'-binaphthyl; 1,1'-bis(diphenylphosphino)-ferrocene; 1,2-bis(2,5-dimtheylphospholano)benzene; 1,2-bis(2,5-dimethylphospholano)ethane; and 1,2-bis(2,5-diethylphospholano)ethane; and camphor-based hydroxylphosphoryl ligands such as endo,endo-3-(diphenylphosphoryl)-2-hydroxybornane. The examples of phosphorous-containing ligands useful in the present invention are not limited to the ligands described above.

A strongly bonded, non-replaceable, neutral or basic, bidentate or multidentate ligand is usually a more stable ligand than a monodentate ligand. Stable ligands containing inorganic phosphoric and phosphorous acid derivatives and organic phosphoric and phosphorous acid derivatives useful in the present invention are bidentate and polydentate ligands such as, for example, phenylphosphonate ($PhPO_3^{-3}$); diphenylphosphinate ($Ph_2PO_2^{-2}$); and hydroxyphosphinate($HPO_3^{-2}$). Stable ligands containing aliphatic, cycloaliphatic, or aromatic organophosphinyl ligands useful in the present invention are bidentate or polydentate ligands, such as, for example, but not limited to 1,2-bis(diphenylphosphino)ethane; 1,3-bis(diphenylphosphino)propane; 1,4-bis(diphenylphosphino)butane; 1-(1'-diphenylphosphino-ferrocenyl)-1-dicyclohexylphosphinyl ethane; 2-(diphenylphosphinyl) cyclohexanol; 2,2'-bis(diphenylphosphino)-1,1'-binaphthyl; 1,1'-bis(diphenyl-phosphino)ferrocene; 1,2-bis(2,5-dimtheylphospholano)benzene; 1,2-bis(2,5-dimethylphospholano)ethane; and 1,2-bis(2,5-diethylphospholano)ethane; and camphor-based hydroxylphosphoryl ligands such as endo,endo-3-(diphenylphosphoryl)-2-hydroxybornane.

The phosphorous-containing ligands may also contain one or more asymmetric or chiral centers. Such asymmetric or chiral phosphorous-containing ligands include, but are not limited to (+)-neomenthyldiphenylphosphine; camphor-based chiral derivatives, such as (1R)-endo,endo-3S-(diphenylphosphoryl)-2R-hyroxybornane; S-(−)- or R-(+)-2,2'-bis(diphenylphosphino)-1,1'-binaphthyl; S-(−)- or R-(+)-2,2'-bis(di-p-tolylylphosphino)-1,1'-binaphthyl; and 2S,3S-(−)- or 2R,3R-(+)-bis(diphenylphosphino)butane.

The phosphorous-containing ligands may also contain one or more hydrophilic moieties. Such hydrophilic phosphorous-containing ligands include, but are not limited to trisodium-3,3',3''-phosphinidynetris(benzenesulfonic acid).

Partially or fully fluorinated monodentate or polydentate phosphorous-containing ligands are also included herein as examples useful in the present invention.

Oxidized monodentate or polydentate phosphorous-containing ligands, for example, organophosphine oxides, such as, triphenylphosphine oxide; tritolylphosphine oxide; tricyclohexylphosphine oxide and 1,2-bis(diphenylphosphino oxide)ethane are also useful in the present invention.

The above-described stable phosphorous-containing ligands are useful for designing transition metal complexes for epoxidation of aryl allyl ethers.

Nitrogen-Containing Ligands

Nitrogen-containing ligands such as monodentate or polydentate amino compounds, heterocyclic ring compounds, biheterocyclic ring compounds or fused heterocyclic ring compounds are ligands useful for the preparation of transition metal complexes of the present invention. The nitrogen-containing ligands may contain heteroatoms other than nitrogen such as O, S, Si, B or P, or any combination of these heteroatoms. Partially or fully fluorinated monodentate or polydentate nitrogen-containing ligands are also included herein as examples useful in the present invention.

The monodentate and bidentate amino ligands useful in the present invention include, for example, but are not limited to, amino ligands having the following general structures, Formulas (B), (B') and (B''):

Formula (B)

$HN(R^6)Ar'$ or

Formula (B')

$HN(SiR^6_3)Ar'$ or

Formula (B'')

$N(SiR^6_3)_2Ar'$ where $R^6$ is methyl, ethyl, isopropyl, tert-butyl, cyclohexyl, and phenyl, and $R^6$ may be partially or fully fluorinated, and Ar' is an aryl group with or without substituents ortho to the nitrogen atom, for example, such as 2,6-diisopropylphenyl; or amino ligands having the following general structure, Formula (C):

Formula (C)

where $R^6$ and Ar' are the same as described above; and n' is from 1 to 5; or tridentate diamino ligands containing oxygen having the following general structure, Formula (D):

Formula (D)

where $R^6$ and Ar' are the same as described above.

Examples of the above amino ligands useful in the present invention are, for example, but not limited to, N,N-bis(2,6-diisopropylphenyl)amine; N-2,6-diisopropylphenyl-N-trimethylsilyl amine; N-tert-butyl-N-3,5-dimethylphenyl amine; N,N-di-trimethylsilyl amine; N,N'-bis(trimethylsilyl)-1,2-diaminoethane; N,N'-bis(2,6-diisopropylpheny)-1,3-diaminopropane; bis[2-(N-2,6-dimethylphenyl aminoethyl)ether; and bis[2-(N-2,6-diisopropylphenyl aminoethyl)ether.

Also included as examples of the amino ligands useful in the present invention are multiaza acyclic, cyclic, and macrocyclic amines, such as, for example, tris[2-(N-trimethylsilyl)aminoethyl]amine; 1,3,5-trimethyl-1,3,5-triazacyclohexane; 1,3,5-tri-tert-butyl-1,3,5-triazacyclohexane; 1,3,5-tribenzyl-1,3,5-triazacyclohexane; 1,5,9-triazacyclododecane; cyclam-(1,4,8,11-tetraazacyclodecane); cyclam-(1,4,7,10-tetraazacyclododecane); 1,2-cyclohexane-diamine-N,N'-bis(3,3-di-tert-butylsalicylidene) known as Jacobsen ligand; ethylenebis-(salicylimine) known as Salen; and 2,6-bis(imino)pyridyl ligands and the related bis(imide)pyridyl ligands described by Gibson, V. C., et al., *Chem. Commun.*, pp. 849–850, (1998) and by Brookhart, M., et al., *J. Am. Chem. Soc.*, 120, 16, pp. 4049–4050, (1998).

The nitrogen-containing monodentate and multidentate monoheterocyclic and multiheterocyclic ligands useful in the present invention include, for example, but are not limited to, monoheterocyclic pyridine ligands such as (2'-pyridyl)propan-2-ol; (2'-pyridyl)-2,4-dimethyl-pentan-3-ol; (2'-pyridyl)cyclohexanol; (2'-pyridyl)pentan-3-ol; 9-(2-pyridyl)-9-fluorenol; bis(4-phenylphenyl)-2-pyridylmethanol; bis[4-(diethylamino)phenyl]-2-pyridylmethanol; 1-(2-pyridyl)dibenzosuberol; 2-cyano-6-(2-hydroxyphenyl)pyridine; and 6-(2-hydroxyphenyl)-pyridine-2-carboxylic acid.

Monodentate and multidentate monoheterocyclic and multiheterocyclic ligands useful in the present invention also include, for example, but not limited to, multiheterocyclic pyridine ligands, such as tris(2'-pyridylaminodimethyl silyl) methane; tris(2'-(4-methylpyridyl)aminodimethyl silyl] methane; tris[2'-(4,6-dimethylpyridyl)aminodimethyl silyl] methane; 2,2'-bipyridine; dendridic bipyridine; and 2,6-bis(2-pyridyl)pyridine.

Monodentate and multidentate monoheterocyclic and multiheterocyclic ligands useful in the present invention include, for example, but are not limited to, multiheterocyclic pyridine-oxazolin, pyridine-pyrazol, and pyrazine-pyrazol ligands such as 2,6-bis[4-methyloxazolin-2-yl] pyridine; and 2,6-bis[4-isopropyloxazolin-2-yl]pyridine; and 4-hydroxymethyl-5-phenyl-2-(2-pyridinyl)4,5-dihydro[2,1-d]oxazole; 2-(5-methylpyrazol-3-yl)pyridine; 2-(5-phenylpyrazol-3-yl)pyridine; 2-(4-chloropyrazol-3-yl) pyridine; 2-(4-bromopyrazol-3-yl)pyridine; 2-(4-nitropyrazol-3-yl)pyridine; 2-(5-methyl-1-octylpyrazol-3-yl)pyridine; 2-(l-octyl-5-phenylpyrazol-3-yl)pyridine; 2-(4-chloro-1-octylpyrazol-3-yl)pyridine; 2-(5-methylpyrazol-3-yl)pyrazine; and 2-(5-methyl-1-octylpyrazol-3-yl)pyrazine.

Nitrogen-containing ligands useful in the present invention include biheterocyclic quinoline and biheterocyclic oxazoline ligands, such as, for example, but are not limited to, 2-methyl-8-hydroxyquinoline; 5,7-dibromo-2-methyl-8-hydroxy quinoline; 2,2'-methylenebis-(oxazoline); and 2,2'-isopropylidenebis(oxazoline).

Nitrogen-containing ligands useful in the present invention also include nitrogen-containing heterocyclic ligands that contain boron, such as, for example, but not limited to, hydrotri(3,5-dimethyl-1-pyrazolyl)borate; hydrotris[5-methyl-3-(3-pyridyl)pyrazolyl]borate; and hydrotris[5-methyl-3-(5-α-picolyl)pyrazolyl]borate.

A strongly bonded, non-replaceable, neutral or basic, bidentate or multidentate ligand is usually a more stable ligand than is a monodentate ligand. Among the stable nitrogen-containing ligands useful in the present invention are those heterocyclic ring or fused heterocyclic rings, such as, for example, but not limited to, N,N-bis(2,6-diisopropylphenyl)amine; N-2,6-diisopropylphenyl-N-trimethylsilyl amine; N-tert-butyl-N-3,5-dimethylphenyl amine; N,N-di-trimethylsilyl amine; N,N'-bis(trimethylsilyl)-1,2-diaminoethane; N,N'-bis(2,6-diisopropylpheny)-1,3-diaminopropane; bis[2-(N-2,6-dimethylphenyl aminoethyl)ether; bis[2-(N-2,6-diisopropylphenyl aminoethyl)ether; tris[2-(N-trimethylsilyl)aminoethyl]amine; 1,3,5-trimethyl-1,3,5-triazacyclohexane; 1,3,5-tri-tert-butyl-1,3,5-triazacyclohexane; 1,3,5-tribenzyl-1,3,5-triazacyclohexane; 1,5,9-triazacyclododecane; cyclam-(1,4,8,11-tetraazacyclodecane); cyclam-(1,4,7,10-tetraazacyclododecane); 1,2-cyclohexanediamine-N,N'-bis(3,3-di-tert-butyl-salicylidene); ethylenebis-(salicylimine); 2,6-bis(imino)-pyridyl ligands; (2'-pyridyl)propan-2-ol; (2'-pyridyl)-2,4-dimethylpentan-3-ol; (2'-pyridyl)cyclohexanol; (2'-pyridyl)-pentan-3-ol; 9-(2-pyridyl)-9-fluorenol; bis(4-phenylphenyl)-2-pyridylmethanol; bis[4-(diethylamino)phenyl]-2-pyridyl-methanol; 1-(2-pyridyl)dibenzosuberol; 2-cyano-6-(2-hydroxy-phenyl)pyridine; 6-(2-hydroxyphenyl)pyridine-2-carboxylic acid; tris(2'-pyridylaminodimethyl silyl) methane; tris[2'-(4-methylpyridyl)aminodimethyl silyl] methane; tris[2'-(4,6-dimethylpyridyl)aminodimethyl silyl] methane; 2,2'-bipyridine; dendridic bipyridine; 2,6-bis(2-pyridyl)pyridine; 2,6-bis[4-methyloxazolin-2-yl]pyridine; 2,6-bis(4-isopropyloxazolin-2-yl)pyridine; 4-hydroxymethyl-5-phenyl-2-(2-pyridinyl)4,5-dihydro[2,1-d]oxazole; 2-(5-methylpyrazol-3-yl)pyridine; 2-(5-phenylpyrazol-3-yl)pyridine; 2-(4-chloropyrazol-3-yl) pyridine; 2-(4-bromopyrazol-3-yl)pyridine; 2-(4-nitropyrazol-3-yl)pyridine; 2-(5-methyl-1-octylpyrazol-3-yl)pyridine; 2-(1-octyl-5-phenylpyrazol-3-yl)pyridine; 2-(4-chloro-1-octylpyrazol-3-yl)pyridine; 2-(5-methylpyrazol-3-yl)pyrazine; 2-(5-methyl-1-octylpyrazol-3-yl)pyrazine; 2-methyl-8-hydroxyquinoline; 5,7-dibromo-2-methyl-8-hydroxy quinoline; 2,2'-methylenebis(oxazoline); 2,2'-isopropylidenebis(oxazoline); hydrotri(3,5-dimethyl-1-pyrazolyl)borate; hydrotris[5-methyl-3-(3-pyridyl) pyrazolyl]borate; and hydrotris[5-methyl-3-(5-α-picolyl) pyrazolyl]borate.

The nitrogen-containing ligands may also contain one or more asymmetric or chiral centers. Such asymmetric or chiral nitrogen-containing ligands include, for example, but are not limited to, (4S,5S)-(+)-4-hydroxymethyl-5-phenyl-2-(2-pyridinyl)-4,5-dihydro-[2,1-d]oxazole; S- or R-(2'-pyridyl)-4-nonanol; S- or R-(2'-pyridyl)cyclohexanol.

Partially or fully fluorinated monodentate or polydentate nitrogen-containing ligands are also included herein as examples useful in the present invention.

Because of their basicity, nitrogen-containing ligands, such as monodentate, monoheterocyclic and bidentate biheterocyclic ligands can also be used as ligands for metals with a higher oxidation state, such as Re. However, some nitrogen-containing ligands are basic substances which may also open the epoxide ring of glycidyl ethers, especially it may open the epoxide ring of aryl glycidyl ethers.

The above-described stable nitrogen-containing ligands are useful for designing transition metal complexes for epoxidation of aryl allyl ethers.

Aromatic Moiety-Containing Ligands

The following Formulas VI to IX represent four types of partial structures for transition metal complexes containing ligands having an aromatic moiety, such as, for example, cyclopentadienyl (Cp), pentamethylcyclopentadienyl (Cp*), indenyl (In), or 9-fluorenyl(Fl) ligands, useful in the hydroperoxide epoxidation process of the present invention.

Formula VI, as follows, is a partial structure of the transition metal complex catalyst illustrated in Scheme I above:

Formula VI

where $R^7$ is Cp, Cp*, In, or Fl; and M is a transition metal, such as Ti, Zr, Hf, V, Mo, W, Re, Mn, La. The above Formula VI represents a "half-shell" transition metal complex.

The monodentate Cp-, Cp*-, In- and Fl-containing ligands are described in Organometallics, 14, pp. 3732–3740 (1995) by Hitchcock, S. An example of such a half-shell transition metal complex is the generalized molybdenum complex shown below in Formula VIa:

Formula VIa

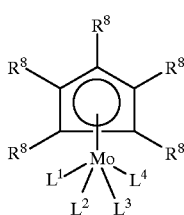

where $R^8$ is hydrogen or methyl, ethyl, isopropyl, cyclohexyl, and phenyl, and are partially or fully fluorinated; $L^1$, $L^2$, $L^3$, and $L^4$ are ligands as defined above and include, for example, the ligands selected from carbon monoxide, Cl, $P(R^6)_3$, $-Si(R^6)_3$, and $-OSi(R^6)_3$; and $R^6$ is the same as defined above.

The Mo complexes having one Cp ligand or the substituted analogue thereof are a very well known class of compounds. Typically these complexes are electronically saturated having 18 valence electrons and contain one or more labile halides or carbon monoxide ligands, for example, Cp*MOCl(CO)$_3$; Cp*(CO)$_2$[(CH$_3$)$_3$P]Mo—Si(CH$_3$)(OH)$_2$; Cp*(CO)$_2$[(CH$_3$)$_3$P]MO—Si(C$_6$H$_5$)(OH)$_2$; CP*(CO)$_2$[(CH$_3$)$_3$P]W—Si(CH$_3$)(OH)$_2$; Cp*(CO)$_2$[(CH$_3$)$_3$P]W—Si(C$_6$H$_5$)(OH)$_2$; Cp*(CO)$_2$[(CH$_3$)$_3$P]Mo—Si(Me)(OSi(CH$_3$)$_2$OH]$_2$; CP*(CO)$_2$[(CH$_3$)$_3$P]MO—Si(C$_6$H$_5$)[OSi(CH$_3$)$_2$OH]$_2$; Cp*(CO)$_2$[(CH$_3$)$_3$P]Mo—Si(OH)$_3$; Cp(CO)$_2$[(CH$_3$)$_3$P]W—Si(OH)$_3$; Cp*(CO)$_2$[(CH$_3$)$_3$P]Mo—Si[OSi(CH$_3$)$_2$H]$_3$; CP*(CO)$_2$[(CH$_3$)$_3$P]W—Si(H)(CH$_3$)$_2$; and CP*(CO)$_2$[(CH$_3$)$_3$P]W—Si(H)(Cl)(CH$_3$).

In such complexes, the labile halide and carbon monoxide ligands may be replaced by more strongly bonding ligands such as, for example, —SiMe$_3$, —OSiMe$_3$, or PMe$_3$. Methods for replacing labile halide and carbon monoxide ligands with more strongly bonding ligands are described by Malisch, W., in J. Chem. Soc., Chem. Commun., pp. 1917–1919 (1995) and in Inorg. Chem., 32, 3, pp. 303–309 (1993).

Also included in the above general Formula VI are electronically unsaturated transition metal complexes with a 16- or 17-electron configuration, for example, Cp*MoCl[P(CH$_3$)$_3$]$_2$; Cp*MoCl$_3$P(CH$_3$)$_3$; Cp*MoCl[P(CH$_3$)$_3$]$_2$ (CO); Cp*MoCl$_2$(dppe); Cp*MoCl$_2$(dppe); and CpMoCl$_2$(dppe) wherein dppe is 1,2-bis(diphenylphosphino)ethane. Examples of such electronically unsaturated transition metal complexes are described in Chem. Rev., 96, pp. 2135–2204 (1996); in Organometallics, 16, pp. 1581–1594 (1997); in J. Am. Chem. Soc., 118, pp. 3617–3625 (1996); and in J. Chem. Soc., Chem. Commun., pp. 2317–2318 (1994), all by Poli, R.

Formula VII set forth below is a partial structure of the transition metal complex catalyst illustrated in Scheme I above:

Formula VII

where $R^7$ and M are as defined above with reference to Formula VI, and wherein each $R^7$ can be the same or different. The above Formula VII represents a metallocene "sandwich" transition metal complex.

An example of such a transition metal metallocene complex useful in the present invention is the generalized molybdenum complex shown below in Formula VIIa:

Formula VIIa

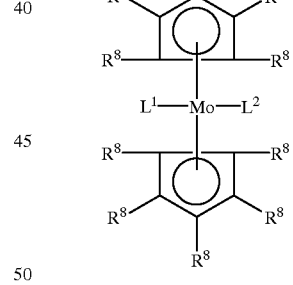

where $R^8$ is as defined above with reference to Formula VI; and $L^1$, $L^2$ are ligands as defined above with reference to Formula VIa.

The above Mo complexes having two Cp ligands or the substituted analogues thereof are a very well known class of compounds. Typically, the complexes are electronically saturated having 18 valence electrons and contain one or more labile halides or carbon monoxide ligands. Examples of such complexes are (Cp)$_2$MoCl$_2$; (Cp)$_2$MoBr$_2$; (Cp*)$_2$MoCl$_2$; (Cp*)$_2$MoBr$_2$; (In)$_2$MoCl$_2$; bis(2-4-methoxyphenyl-4,5,6,7-tetrahydroindenyl)MCl$_2$; bis(2-4-methylphenyl-4,5,6,7-tetrahydroindenyl)MCl$_2$; and bis(2-4-bromophenyl-4,5,6,7-tetrahydroindenyl)MCl$_2$; where in Cp, Cp*, In, and M are as previously defined. The Cl or Br ligands in such complexes can be replaced by more strongly bonding ligands such as, for example, —SiMe$_3$ or —OSiMe$_3$ as described by Malisch, W., in *J. Chem. Soc., Chem. Commun.*, pp. 1917–1919 (1995) and in *Inorg. Chem.*, 32, 3, pp. 303–309 (1993).

Formula VIII set forth below is a partial structure of the transition metal complex catalyst illustrated in Scheme I above:

Formula VIII where R$^7$ and M are as defined with reference to Formula VII above and where X' is a moiety bridging or linking the R$^7$ groups together such that the R$^7$—X'—R$^7$ structure becomes a bidentate ligand, wherein R$^7$ can be the same group or a different group. X' may be, for example, methylene, ethylene, isopropylidene, binaphthyldimethylene, dimethylsilylene, and bis(dimethysilyl)oxy. The above Formula VIII represents an "ansa ring" transition metal complex.

The Mo complexes represented by Formula VIII are a very well known class of compounds. Typically, these complexes are electronically saturated having 18 valence electrons and contain one or more labile halide or carbon monoxide ligands. Such complexes may be synthesized by a method described by Hermann, W., in *Angew. Chem., Int. Ed. Engl.*, 33, 19, pp. 1946–1949 (1994). The synthesis scheme disclosed by Hermann is set forth below for illustration purposes and not to be limited thereby:

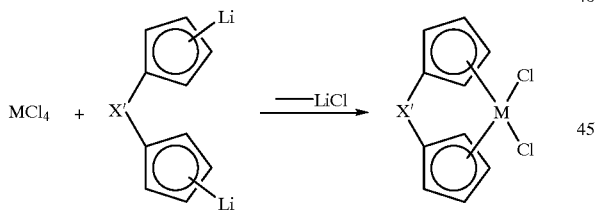

In the above synthesis scheme, M and X' are defined above with reference to Formula VIII.

In such complexes, the labile halide ligands may be replaced by ligands, such as, for example, —SiMe$_3$, or —OSiMe$_3$. Methods to replace labile halide ligands with more strongly bonding ligands are described by Malisch, W., in *J. Chem. Soc., Chem. Commun.*, pp. 1917–1919 (1995) and in *Inorg. Chem.*, 32, 3, pp. 303 309 (1993).

An example of a transition metal complex with bidentate "ansa" ligand according to Formula VIII is a molybdenum complex of Formula VIIIa shown below:

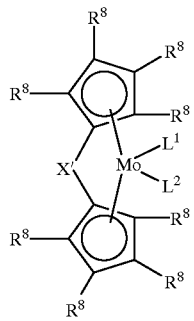

Formula VIIIa where R$^8$ is defined above; L$^1$ and L$^2$ in the above specific molybdenum complex are ligands selected from carbon monoxide, Cl, P(R$^6$)$_3$, —Si(R$^6$)$_3$, and —OSi(R$^6$)$_3$, and R$^6$ is defined above. R$^6$ can also be partially or fully fluorinated. X is the bridge linking the Cp groups together. Therefore, Cp—X'—Cp becomes an "ansa" ring-containing bidentate ligand, X is methylene, ethylene, isopropylene, and dimethylsilylene. Such "ansa" ring-containing bidentate ligands useful in the present invention include, for example, but are not limited to, bis(4-tert-butyl-2-methylcyclopentadienyl)dimethylsilane; bis(cyclopentadienyl)dimethylsilane; bis(9-fluorenyl)dimethylsilane; bis(1-indenyl)dimethylsilane; bis(2-methyl-1-indenyl)dimethylsilane; cyclopentadienyl-(9-fluorenyl)diphenylmethane; cyclopentadienyl-(9-fluorenyl)dimethylsilane; 1,2-bis(1-indenyl)ethane; 1,2-bis(2'-methyl-1-indenyl)ethane; 1,2-bis(4',5',6',7'-tetrahydro-1-indenyl)ethane; 2,2-(cyclopentadienyl)-(9-fluorenyl)propane; and bis-(1-benzoindenyl)-dimethylsilane.

A strongly bonded, non-replaceable, neutral or basic, bidentate or multidentate ligand is usually a more stable ligand than monodentate ligand. Among the stable ligands useful in the present invention having Cp, Cp*, In, and Fl are, for example, those bidentate ligands or multidentate ligands as shown in Formula VIII above.

Formulas IXA, IXB, IXC set forth below represent "ansa" type transition metal complexes wherein one of the metal ligand bonds is formed through an ancillary group:

Formula IXA

Formula IXB

Formula IXC where R$^7$, X', and M in Formulas IXA, IXB and IXC are as defined above with reference to Formula VIII. A is an ancillary group attached to the R$^7$ or X' group, wherein A is a moiety including, for example, but not limited to, an alkyl amine, a cycloalkyl amine, an aromatic amine or any combination thereof; an alkyl alcohol, a cycloalkyl alcohol, an aromatic alcohol, or any combination thereof; an alkyl ether, a cycloalkyl ether, an aromatic ether or any combination thereof; an alkyl organophosphine, a cycloalkyl organophosphine, an aromatic organophosphine or any combination thereof. Therefore, the $R^7$—A moiety is a bidentate ligand.

A strongly bonded, non-replaceable, neutral or basic, bidentate or multidentate ligand is usually a more stable ligand than a monodentate ligand. Among the stable ligands useful in the present invention having Cp, Cp*, In, and Fl are those bidentate ligands or multidentate ligands as shown in Formula IXA, IXB and IXC above.

A specific structure of an "ansa" type molybdenum complex having a stable Cp ligand with ancillary group is shown below as Formula IXAa:

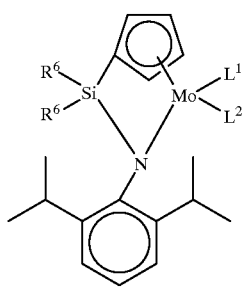

Formula IXAa where $R^6$, $L^1$ and $L^2$ are ligands and $L^1$, $L^2$ and $R^6$ are as defined with reference to Formula VIa above. Other than the 2,6-diisopropylphenyl group, the substituent on the nitrogen atom in the above Formula IXAa can also be, for example, isopropyl, tert-butyl, n-butyl, adamantyl, 2,6-dimethylphenyl, cyclohexyl, and dodecanyl. Complexes of Formula IXAa are described, for example, in J. Chem. Soc., Dalton Trans., pp. 4143–4146 (1996) and in Organometallics, 15, pp. 3176 3181 (1996) both by Roesky, H.

In such complexes having remaining labile ligands, such as, for example, halide or carbon monoxide, the remaining labile ligands may be replaced by ligands such as, for example, —SiMe$_3$, or —OSiMe$_3$. Methods to replace labile ligands with such ligands are described by Malisch, W., in J. Chem. Soc., Chem. Commun., pp. 1917–1919 (1995) and in Inorg. Chem., 32, 3, pp. 303–309 (1993).

Other specific "ansa" type ligands with an ancillary group include, for example, but are not limited to, bis(Cp*)(3-methoxy-1-propyl)methylsilane; bis(Cp*)(3-methoxy-1-pentyl)methylsilane; dimethyl (dimethylaminoethylcyclopentadienyl)(Cp*)silane; trimethyl(2-methoxyethylcyclopentadienyl)silane; trimethyl (2-isobornyloxyethylcyclopentadienyl)silane; trimethyl(2-menthylethyloxycyclopentadienyl)silane; trimethyl(2-fenchyloxyethylcyclopentadienyl)silane; N,N-dimethyl-2-aminoethylcyclopentadiene; N,N-dimethyl-3 -aminopropylcyclopentadiene; and (Cp)dimethyl(diphenylphosphinomethyl)silane.

A strongly bonded, non-replaceable, neutral or basic, bidentate or multidentate ligand is usually a more stable ligand than a monodentate ligand. Among the stable ligands useful in the present invention having Cp, Cp*, in, and Fl are those bidentate ligands or multidentate ligands as shown in Formula IXA, IXB and IXC above.

Organosilyl- and Organosilyloxy-containing Ligands

The incorporation of silicon-based functionality within the transition metal complexes of the present invention is important not only because it provides the chemical functionality for bonding of the transition metal complexes to solid supports, but also the silicon-based ligands impart advantageous catalyst solubility and catalyst hydrolytic stability properties. The silicon-based ligands also impart hydrophobic properties to the catalysts that can reduce the hydrolysis of epoxide to glycol.

Silicon-containing ligands can be generally divided into two groups, organosilyl-containing ligands and organosilyloxy-containing ligands.

In the organosilyl-containing ligands, the silicon atom is directly bonded to the transition metal atom. An example of a monodentate organosilyl-containing ligand is —Si(R$^6$)$_3$ and an example of bidentate or multidentate organosilyl-containing ligand is —Si(R$^6$)$_2$[—O—Si(R$^6$)$_2$]$_{m''}$—O—Si (R$^6$)$_2$— where R$^6$ is the same as described above and m" is from 0 to 10.

Transition metal complexes with organosilyl-containing ligands can be made by reacting an organosilyl alkali metal salt wherein the alkali metal is lithium, sodium, or potassium; or by reacting a transition metal chloride- or a transition metal bromide-containing complex with an organosilyl magnesium chloride salt. Thus, the transition metal to chloride or transition metal to bromide bond is replaced by a transition metal to silicon bond. The method used to make such organosilyl ligands where the silicon atom is directly linked to the transition metal is taught, for example, by Malisch, W., in Inorg. Chem., 34, 23, pp. 5701–5702 (1995).

Organosilyl-containing ligands may also be introduced into a transition metal complex by indirectly attaching the organosilyl-containing moiety to the transition metal atom through a monodentate ligand, such as —L—Si(R$^6$)$_3$ wherein L is a ligand as defined above. An example of such a monodentate organosilyl-containing ligand is γ-aminopropyltrimethoxy-silane, wherein an amido moiety is attached to one terminus and an organosilyl moiety is attached to the other terminus of the ligand such as described in U.S. Pat. No. 5,620,938.

Organosilyloxy-containing ligands, may be monodentate ligands such as —O—Si(R$^6$)$_3$ or multidentate ligands, such as, —O—Si(R$^6$)$_2$[—O—Si(R$^6$)$_2$]$_{m''}$—O—Si(R$^6$)$_2$—O—, wherein the silicon atom is indirectly bonded to the transition metal through an oxygen atom, where R$^6$ and m" are as defined above.

Organosilyloxy-containing ligands may also be introduced into a transition metal complex by indirectly attaching the organosilyloxy-containing moiety to the transition metal atom through a monodentate ligand, such as —L—O—Si (R$^6$)$_3$ wherein L is as defined above. One such method to introduce an organosilyloxy-containing ligand into a transition metal complex is taught, for example, by Malisch, W., in Inorg. Chem., 34, 23, pp. 5701–5702 (1995). The synthesis scheme disclosed by Malisch is set forth below for illustration purposes and not to be limited thereby.

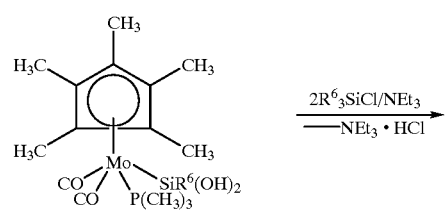

-continued

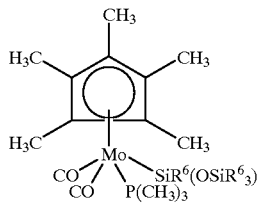

When using the lithium salts of organosilane diols or triols to react with transition metal halides, transition metal complexes having the following general structures, Formulas (E) and (F) can be formed:

Formula (E)

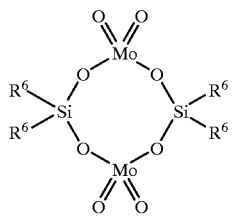

and

Formula (F)

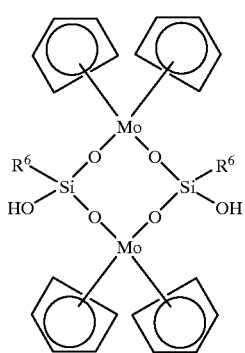

where the substituent $R^6$ is as described above.

When a transition metal complex with mono-, di- or trifunctional organosilyl hydroxy groups is condensed with mono-, di-, tri- or tetramethoxy or mono-, di-, tri- or tetraethoxy silane, a hybrid organic-inorganic material is formed. Such hybrid organic-inorganic material may be soluble or partially soluble in organic solvents. One process for making organic soluble or partially organic-soluble hybrid organic-inorganic materials useful in the present invention is described by Shea, K. J., et al., in *Chem. Rev.*, 95, pp. 1431–1442 (1995). Another process for making organic soluble or partially organic-soluble hybrid organic-inorganic materials uses Si—OH containing dendrimers and is described by Majoral, J. P., et al., in *Chem. Rev.*, 99, pp. 845–880 (1999).

When transition metals with ligands are singly bonded to a silsesquioxane, an organic soluble metallosiloxane is formed, such as the example shown in the general structure—, Formula (G) below:

Formula (G)

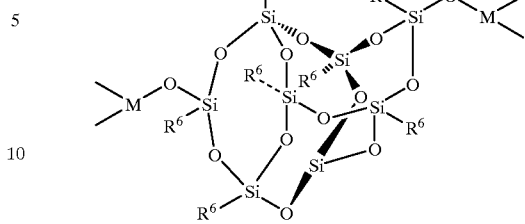

where the substituent $R^6$ is as described above.

The organic soluble, transition metal silsesquioxane shown above can be anchored or bonded onto a silicate-based, solid support to form a heterogeneous catalyst. When the transition metal is linked to the silsesquioxane through multiple M—O—Si bonds, it is very tightly bonded as shown in the general structure, Formula (H) below:

Formula (H)

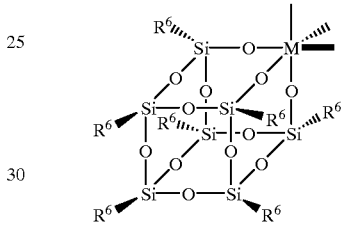

where the substituent $R^6$ is as described above. Therefore, when an M—O bond of an M—O—Si moiety is dissociated by the insertion of a hydroperoxide, such as TBHP, during the epoxidation reaction, the transition metal atom still remains bound to the silsesquioxane framework through one or more M—O—Si bonds. Therefore, there will be less undesirable "leaching" of the transition metals.

A strongly bonded, non-replaceable bidentate or multidentate ligand is usually more stable than a monodentate ligand. Among the stable ligands useful in the present invention are the bidentate ligands or multidentate ligands having organosilyl or organosilyloxy moieties described above.

The above-described stable organosilyl- and organosilyloxy-containing ligands are useful for designing transition metal complexes for epoxidation of aryl allyl ethers.

Homogeneous/Heterogeneous Catalyst Systems

One embodiment of the present invention includes a process for making the epoxies of aryl glycidyl ethers via epoxidation of aryl allyl ethers which optionally utilizes either a homogeneous or a heterogeneous transition metal complex as the catalyst.

When certain ligands or combinations of ligands are selected to make a transition metal complex catalyst, the transition metal complex catalyst will be soluble in the epoxidation reaction mixture. When a transition metal complex catalyst is soluble, high efficiency in the epoxidation reaction is attained because of the homogeneous mixing.

In the epoxidation process of the present invention utilizing a homogeneous catalyst, a preferred molar ratio of the transition metal catalyst to aryl allyl ether present in the reaction mixture is from $1 \times 10^{-6}$ to 1 mole of catalyst per 1 mole of aryl allyl ether; a more preferred molar ratio of the transition metal catalyst to aryl allyl ether present in the reaction mixture is from $1 \times 10^{-6}$ to $1 \times 10^{-1}$ mole of catalyst per 1 mole of aryl allyl ether; the most preferred molar ratio of the transition metal catalyst to aryl allyl ether present in the reaction mixture is from $1 \times 10^{-6}$ to $1 \times 10^{-2}$ mole of catalyst per 1 mole of aryl allyl ether.

Once the epoxidation has been carried out to the desired degree of conversion, the epoxide product may be separated and recovered from the reaction mixture using appropriate techniques such as filtration, fractional distillation, extractive distillation, liquid-liquid extraction, solid-liquid extraction and crystallization, or any combination of these.

In another embodiment of the present invention, a transition metal catalyst complex which is a heterogeneous catalyst may be used. By heterogeneous catalyst it is meant that the transition metal complex catalyst is (i) insoluble in the epoxidation reaction mixture; (ii) placed onto a solid support material by deposition onto the solid support or by anchoring onto the solid support; or (iii) placed in a solid support by encapsulation in the solid support.

When the heterogeneous catalyst is formed by deposition of the transition metal catalyst of Formula (A) onto a solid support, the transition metal catalyst of Formula (A) is dissolved in a solvent and the solution of transition metal catalyst of Formula (A) is then absorbed onto the solid support and the solvent subsequently removed by any of several procedures well know to those familiar in the art.

The heterogeneous catalyst, made by the process of depositing the transition metal catalyst of Formula (A) onto a solid support, may be utilized directly or the heterogeneous catalyst may be subsequently calcined. When a calcination process is involved, the calcination temperature may be from 50° C. to 1000° C., more preferably from 100° C. to 700° C., and even more preferably from 150° C. to 500° C. When calcination occurs at these temperatures, the organic ligands bound to the transition metal catalyst may be totally displaced by reactive groups, such as, for instance, the hydroxyl groups of silicate supports, on the support. In this case, the transition metal catalyst is strongly bound to the silicate solid support through the formation of stable siloxy bonds between the transition metal and the silicate solid support.

In the process wherein the transition metal catalyst of Formula (A) is deposited onto a solid support, the solid support may include, for example, but is not limited to, cross-linked polymers or ion exchange resins such as those based on styrene-co-divinyl benzene or vinyl pyridine-co-divinyl benzene; aromatic polyimides; organosol gels; charcoals; carbons; silicas; aluminas; $Ba_2SO_4$; MgO; clays; silicates; zeolites; phosphites; aluminates; or any combination thereof.

The zeolite or silicate solid support materials useful in the present invention are those with a microporous crystalline structure having a pore size similar to 4 Å type molecular sieves or those with a mesoporous crystalline structure having a pore size larger than 4 Å type molecular sieves. The zeolites, silicates, aluminophosphates, and silica aluminophosphates useful in the present invention are, for example, TS-1, TS-2, ZSM-5, ZSM-11, ZSM-12, ZSM-22, AZM-48, SAPO-5, SAPO-11, zeolite X, zeolite Y, Linde type L, VPI-5, NCL-1, MCM-41, and MCM-48.

Also useful as support materials for the heterogeneous catalysts of the present invention include, for example, the zeolites or silicates having a larger pore size described above which have been modified to be less acidic in nature, such as low aluminate-containing silicate, "zeolite beta," as described by Bekkum, H., et al., in *Applied Catalysis, A: General*, 167, pp. 331–342, (1998). Zeolites or silicates having a larger pore size described above which have been modified to be less acidic in nature also include the zeolites or silicates which have been neutralized by ion exchange with alkali metal salts such as, for example, lithium acetate and sodium acetate.

Other examples of supports modified to be less acidic and which are therefore useful as supports for the heterogeneous catalysts of the present invention include Ti-beta, Ti-MCM-41, Ti-silicalite-1 (TS-1), TS-2, Ti-ZSM-48, Ti-APSO-5 and Ti-HMS. Solid supports, which are acidic in nature and which are used to support epoxidation catalysts in epoxidizing aliphatic alkenes, are known to destroy epoxide rings and form a ring-opened by-product with a glycol structure. Such acidic support materials are undesirable for use in the present invention to achieve high epoxidation yields for aryl allyl ethers. Thus, the zeolite and silicate support materials described above which have less acidity are preferably used in the present invention as support materials for heterogeneous epoxidation catalysts.

As aforementioned, a heterogeneous catalyst may be formed by anchoring the transition metal catalyst of Formula (A) onto a solid support. By anchoring the transition metal catalyst of Formula (A) onto a solid support, it is meant that stable, covalent chemical bonds or strong ionic bonds are formed between the transition metal catalyst and the solid support, therefore rendering the transition metal catalyst into the heterogeneous state.

The heterogeneous catalyst useful in the present invention may further be made by a process wherein the transition metal complex catalyst of Formula (A) is anchored onto a solid support through the formation of a strong, stable ligand-metal bond. In this process for the preparation of a heterogeneous catalyst, a ligand(s) is bound onto, or is a part of, the constituents of the solid support. The transition metal catalyst is anchored to the solid support via an exchange reaction in which the stronger, more stable ligand of the solid support displaces a weaker ligand on the transition metal complex to form a new transition metal complex in which the solid support is part of a ligand attached to the metal. Examples of such process for the formation of transition metal catalysts anchored onto a solid support is described by Jiang, J., et al., in *J. Macromolecular Science, Part A: Chem.*, 35, 3, pp. 531–538 (1998) and by Clark, J., et al., in *Chem. Commun.*, pp. 853–860 (1998).

The heterogeneous catalyst of the present invention may further be made by a process wherein the transition metal complex catalyst of Formula (A) is anchored onto a solid support through a condensation reaction between a reactive group on a ligand of the transition metal complex and a reactive group on the solid support. An example of such a process for the formation of transition metal catalysts anchored onto a solid support is described by Corma, A., in *J. Chem. Soc., Chem. Commun.*, pp. 795–796 (1997). For example, a transition metal catalyst of Formula (A) may be anchored onto a solid support through a condensation reaction between Si—OH groups on the transition metal complex and Si—OH groups on a solid support. Transition metal complex catalysts, which are soluble in organic solvents and which contain organosiloxane moieties such as —Si—OH and —O—Si—OH, can be anchored or tethered onto highly cross-linked siloxane gels; or onto dendrimers terminated with Si—OH moieties, such as the example described by Majoral, J. P., et al., in *Chem. Rev.*, 99, pp. 845–880 (1999); or onto silicates through Si—OH condensation reactions, to form a heterogeneous catalyst. In another embodiment, the transition metal catalyst having an —L—Si—OH moiety may also be anchored to a siloxane gel or a silicate through condensation of Si—OH groups as shown in the example general structure, Formula (J) below, where $L_1$ and $L_2$ are ligands as described above.

Formula (J)

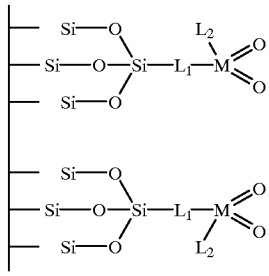

An example of Si—OH condensation reactions used to form heterogeneous catalysts is described by Arai, T., et al., in *J. Polymer Sci., Part A: Polymer Chemistry*, 36, pp. 421–428 (1998). Partially or fully fluorinated monodentate or polydentate silicon-containing ligands are also included herein.

More specifically, transition metal catalysts of Formula (A) having M—Si—OH or M—L—Si—OH groups are anchored onto a silsesquioxane, by first forming a single bond to an organic-soluble metallosiloxane, such as, for example, the aforementioned structure, Formula (G), shown below:

Formula (G)

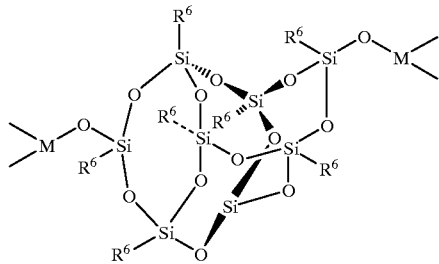

where the substituent $R^6$ is as defined above. Then the organic soluble metallosilsesquioxane shown above in structure, Formula (G), is anchored onto a silicate-based, solid support to form a heterogeneous catalyst.

Furthermore when the transition metal of the organic soluble metallosilsesquioxane transition metal catalyst is multiply bonded through M—O—Si bonds, it is very tightly bonded to the silsesquioxane as illustrated in structure (H) below:

Formula (H)

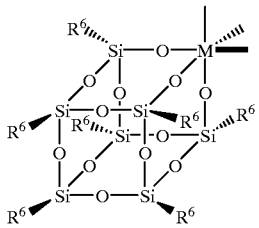

Therefore, when an M—O bond of an M—O—Si moiety dissociates because of the insertion of a hydroperoxide, such as TBHP, into the M—O bond, the metal atom remains bound to the silsesquioxane framework through one or more remaining M—O—Si moieties. Thus, after the metallosilsesquioxane is anchored to a solid support through hydroxyl condensation reactions, there will be less leaching of the transition metals after repeated use of the heterogeneous catalyst and the reuse of heterogeneous metal complex catalyst is possible.

More specifically, the heterogeneous catalyst of the present invention may be made by a process wherein the transition metal complex catalyst of Formula (A) is anchored or tethered to an oligomeric or polymeric solid support through an ionic bond between the transition metal complex and a cationic moiety which is attached or tethered to the solid support. In the above general catalyst structure, Formula (A), each of the $G^1$, $G^2$, $G^3$, $G^4$ . . . $G^p$ is a cation moiety comprised of one or more quaternary cation centers of nitrogen, phosphorous, arsenic, antimony, or bismuth, with one or more organic substituents bound to each quaternary cationic center. When an organic, inorganic or hybrid organic-inorganic oligomeric or polymeric structure contains multiple hydrocarbon substituents containing 1–20 carbon atoms selected from linear, branched or cyclic aliphatic or aromatic, with or without heteroatoms, such as N, P, S, O, Si, or halide atoms, such as F, Cl, Br, and I, or the combination thereof and such hydrocarbon substituents are pendant to the oligomeric or polymeric backbone and bound to a quaternary cationic center, the organic, inorganic or hybrid organic-inorganic oligomeric or polymeric structure may be linked to more than one transition metal atom. In this case, the transition metal catalysts are anchored or tethered to the organic, inorganic or hybrid organic-inorganic polymeric support. An example of such a hydrocarbon substituent pendant to an oligomeric or polymeric backbone and bound to a quaternary cationic center is the benzyl moiety of the benzyltrimethylammonium group formed when cross-linked polystyrene is first chloromethylated and then aminated with trimethylamine.

In another embodiment of the present invention, when trimethoxysilyl- or triethoxysilyl-containing cationic centers, such as, for example, trimethoxysilylpropyltri-n-butylammonium, triethoxysilylpropyltri-n-butylammonium, trimethoxysilyl-propyltrimethylammonium, trimethoxysilylpropyltriethylammonium, octadecyl-dimethyltrimethoxysilylpropylammonium, n-tetradecyldimethyltrimethoxysilylpropyl-ammonium, and trimethylsilylethoxyethyltriphenylphosphonium, are condensed with tetraethoxysilane; a Si—OH containing dendrimer, such as ones described by Majoral, J. P., et al., in *Chem. Rev.*, 99, pp. 845–880 (1999); a silicate; or a zeolite, then a sol-gel, silicate or zeolite, which contains quaternary ammonium or quaternary phosphonium cationic centers, is formed. When these quaternary cationic centers form ionic bonds with the transition metal complex, the transition metal complex is anchored or tethered to the sol-gel, silicate or zeolite.

The silicate and zeolite solid support materials useful in the present invention are, for example, those with a microporous crystalline structure having a pore size similar to 4 Å type molecular sieves or those with a mesoporous crystalline structure having a pore size larger than 4 Å type molecular sieves. The zeolites, silicates, aluminophosphates, and silica aluminophosphates useful in the present invention are, for example, TS-1, TS-2, ZSM-5, ZSM-11, ZSM-12, ZSM-22, AZM-48, SAPO-5, SAPO-11, zeolite X, zeolite Y, Linde type L, VPI-5, NCL-1, MCM-41, and MCM-48.

As aforementioned, a heterogeneous catalyst may also be formed by encapsulating the transition metal catalyst of Formula (A) in a solid support. The encapsulating process involves assembling a transition metal catalyst of Formula (A) in the intrazeolite space of the support such that the transition metal catalyst of Formula (A), once formed inside the zeolite is too large to diffuse out of the zeolite. There is no covalent attachment of the transition metal complexes of Formula (A) to the intrazeolite surface; therefore, the transition metal catalyst complexes of Formula (A) can be expected to more closely resemble their homogeneous counterparts. The encapsulation of transition metal catalyst of Formula (A) will simplify the separation of the transition metal catalyst from the final epoxidation product. An example of this encapsulation technique is described in *Coord. Chem. Rev.*, 144(1995), p.39, by Bedioui, F.

In one embodiment of the heterogeneous catalyst process of the present invention, the ratio of the amount of the transition metal or transition metal complex in the catalyst to the total weight of the solid support material is preferably in the range of from $1 \times 10^{-6}$ part to 1 part of transition metal or transition metal complex per 1 part of solid support; more preferably the ratio of the total weight of the transition metal or transition metal complex metal in the catalyst to the total weight of the solid support material is in the range of from $1 \times 10^{-6}$ part to $1 \times 10^{-1}$ part of transition metal or transition metal complex metal per 1 part of solid support; and most preferably, the ratio of the total weight of the transition metal or transition metal complex metal in the catalyst to the total weight of the solid support material is in the range from $1 \times 10^{-6}$ part to $1 \times 10^{-2}$ part of transition metal or transition metal complex metal per 1 part of solid support.

In another embodiment of the heterogeneous catalyst of the present invention, the weight ratio of heterogeneous catalyst to substrate aryl allyl ether in the epoxidation reaction mixture is in the range of from $1 \times 10^{6}$ parts to $1 \times 10^{-6}$ part of heterogeneous catalyst to 1 part of aryl allyl ether; preferably, the weight ratio of heterogeneous catalyst to substrate aryl allyl ether in the epoxidation reaction mixture is in the range of from $1 \times 10^{3}$ parts to $1 \times 10^{-4}$ part of heterogeneous catalyst to 1 part of aryl allyl ether; and more preferably, the weight ratio of heterogeneous catalyst to substrate aryl allyl ether in the epoxidation reaction mixture is in the range of from $1 \times 10^{2}$ parts to $1 \times 10^{-2}$ part of heterogeneous catalyst to 1 part of aryl allyl ether.

The heterogeneous catalysts of the present invention are reusable after each reaction by purification through washing with certain non-reactive solvents or dilute acid or base. Once the epoxidation has been carried out to the desired degree of conversion, the epoxide product may be separated and recovered from the reaction mixture using appropriate techniques such as filtration, washing, fractional distillation, extractive distillation, liquid—liquid extraction, solid-liquid extraction and crystallization, or any combination of these methods.

Solvent

The reaction of the present invention may be carried out optionally in the presence of a solvent. Solvents that may be used in the reaction mixture of the present invention include solvents that do not react with the inorganic or organic hydroperoxide used in the reaction mixture of the present invention. For example, some solvents, such as dimethylsulfoxide, will react with organic hydroperoxide, such as tert-butyl hydroperoxide (TBHP). Solvents which can be used in the present invention include, for example, aliphatic, cycloaliphatic or aromatic hydrocarbon solvents; partially or fully chlorinated, fluorinated, or combinations therefor halogenated aliphatic, cycloaliphatic or aromatic hydrocarbon solvents; aliphatic, cycloaliphatic or aromatic alcohols and nitrites; and partially or fully fluorinated aliphatic, cycloaliphatic or aromatic alcohol and nitrile solvents.

Preferably, the solvents used in the present invention are chlorinated solvents such as methylene chloride, chloroform, carbon tetrachloride, chloroethane, dichloroethane, tetrachloroethane, 1-chloropropane, 2-chloropropane, and chlorobenzene; nitrile solvents such as acetonitrile, propionitrile, and benzonitrile; hydrocarbon solvents such as n-pentane, cyclopentane, methylcyclopentane, n-hexane, 2,5-dimethylhexane, 2,3-dimethylbutane, cyclohexane, methylcyclohexane, 1,3-dimethylcyclohexane, n-heptane, n-octane, isooctane, n-nonane, and n-decane; aromatic solvents such as benzene, toluene, ethyl benzene, xylene, and cumene; and low boiling point alcohols such as ethanol, propanol, isopropanol, n-butanol, sec-butanol, tert-butanol, n-amyl alcohol, tert-amyl alcohol, n-hexanol and cyclohexanol. The above list of solvents is not intended to be an exhaustive list but only a representation of the solvents that are useful in the present invention.

Preferably, the chlorinated solvents are used in the present invention, such as, for example, methylene chloride, dichloroethane, tetrachloroethane and chlorobenzene.

In another embodiment of the present invention, solvents which may be used in the present invention are solvents that may be used under dense phase or supercritical conditions. Such solvents include, for example, but are not limited to, carbon dioxide, ethane, and dimethyl ether.

Solvents of particular utility in the present invention are ones that form azeotropic boiling mixtures with water or an alcohol, such as, t-butanol or tert-amyl alcohol produced when the hydroperoxide is reduced in the epoxidation reaction. Such a solvent choice allows for continuous removal of the water or the alcohol produced in the epoxidation reaction, and hence, allows for more efficient catalyst productivity since the water or the alcohol produced may form strong ligand bonds to the transition metal atom thus reducing its catalytic activity.

Solvents that form azeotropic boiling mixtures with water or an alcohol such as t-butanol, include, for example, cyclopentane, pentane, benzene, cyclohexane, methylcyclopentane, 2,3-dimethylbutane, hexane, heptane, ethylbenzene, 1,3-dimethylcyclohexane, and 2,5-dimethylhexane.

Solvents that form azeotropic boiling mixtures with water or an alcohol, such as tert-amyl alcohol, include, for example, benzene, cyclohexane, methylcyclopentane, toluene, methylcyclohexane, heptane, ethylbenzene, 1,3-dimethylcyclohexane, 2,5-dimethylcyclohexane, and octane.

The continuous removal of azeotropic compositions can be done at ambient, sub-ambient, or super-ambient conditions. The azeotropic composition can be separated and the solvent continuously returned to the reactor.

The solvent useful in the present invention is generally employed in an amount of from 0 parts by weight to 100 parts by weight of solvent per one part of substrate aryl allyl ether. Preferably, the solvent amount used is from 0 parts to 25 parts by weight of solvent per one part of substrate aryl allyl ether and more preferably from 0 parts to 10 parts by weight of solvent per one part of substrate aryl allyl ether.

Additives

An optional additive which may be used in the present invention may include, for example, a free-radical inhibitor.

Such free-radical inhibitors are advantageously used to reduce non-epoxidation reactions and thus to improve the hydroperoxide selectivity. Examples of free-radical inhibitors useful in the present invention include, for example, 4-methyl-2,6-di-tert-butylphenol, 1,4-hydroquinone, 4-methoxyphenol, phenothiazine, and 4-tert-butylcatechol. The amount of such free-radical additive used in the present invention may be from 0 to less than 5 weight percent based upon the total weight of substrate aryl allyl ether.

Another optional additive which may be used in the present invention may include, for example, an organic base or buffering agent. An organic base or buffering agent is particularly useful in combination with a transition metal complex catalyst having a higher oxidation state metal such as the aforementioned Mn- and Re-based catalysts. Such organic base or buffering agent is preferably used in the process of the present invention so that the epoxidation reaction is carried out under neutral or slightly basic conditions. When the epoxidation reaction is carried out under neutral or slightly basic conditions, the undesirable ring opening of the epoxide product is avoided.

Organic bases useful in the present invention include, for example, organic pyridinyl derivatives such as pyridine, and 3-cyanopyridine. The amount of such organic base additive used in the present invention may be from 0 to less than 20 weight percent based upon the total weight of substrate aryl allyl ether. However, some organic bases such as pyridine are catalysts for opening the epoxide ring of a glycidyl ether. The epoxide ring(s) of an aryl glycidyl ether is particularly susceptible to ring opening by organic bases. Therefore, it is preferred to use an amount of the organic base which is not detrimental to the epoxidation reaction, for example, the amount of organic base may be preferably less than about 5 weight percent based upon the total weight of substrate aryl allyl ether.

Reaction Conditions

The reaction temperature of the present invention should be sufficient to accomplish substantial conversion of the aryl allyl ether to epoxide within a reasonably short period of time. It is generally advantageous to carry out the reaction to achieve as high hydroperoxide conversion as possible, preferably at least 50 percent and desirably at least 90 percent, consistent with reasonable selectivities. The optimum reaction temperature will be influenced by catalyst activity, aryl allyl ether reactivity, reactant concentrations, and type of solvent employed, among other factors. But typically, the reaction of the present invention is carried out at a temperature of from 0° C. to 120° C., preferably from 10° C. to 100° C., and more preferably from 20° C. to 80° C.

Reaction times of from 10 minutes to 48 hours will typically be appropriate, depending upon the above-identified variables. Preferably, the reaction time may vary from 30 minutes to 24 hours.

The reaction pressure may be atmospheric, sub-atmospheric (for example, from 5 millimeters of mercury to less than 760 millimeters of mercury) or super-atmospheric (for example, from 1 atmosphere to 100 atmospheres). It is preferred to carry out the reaction under an inert atmosphere such as nitrogen, helium or argon. Generally, it will be desirable to maintain the reaction components as a liquid phase mixture. However, the reaction may be run under such conditions that water or alcohol produced by reduction of the hydroperoxide in the epoxidation reaction with solvent are removed as vapor.

The process of the present invention may be carried out in a stirred batch, semi-continuous or continuous manner, using any appropriate type of reaction vessel or apparatus. Thus, the reactants may be combined all at once or sequentially. For example, the hydroperoxide may be added incrementally to the reaction zone. For example, when hydroperoxide is used in an excess amount, it is preferred that the hydroperoxide be continuously added into the mixture of aryl allyl ether and catalyst.

During the period of reaction, the reaction mixture may be analyzed by gas chromatography, high pressure liquid chromatography or other well-known analytic means.

After the epoxidation reaction is carried out, the reaction mixture is subjected to purification and separation by known process means and the excess, unused, organic oxidant may be recycled. For example, once the epoxidation reaction has been carried out to the desired degree of conversion, the desired epoxide product may be separated and recovered from the reaction mixture using appropriate techniques such as filtration, fractional distillation, extractive distillation, liquid—liquid extraction, solid-liquid extraction, or crystallization.

The co-product of the reaction will generally be the corresponding alcohol derived from the reduction of organic hydroperoxide and may similarly be separated and recovered for use as a valuable product in its own right. For example, tert-butyl alcohol will be produced if TBHP is employed as the oxidant, while 1-phenylethanol is obtained using ethyl benzene hydroperoxide as the oxidant. The alcohol product can, in turn, be readily dehydrated to a useful olefin such as isobutylene or styrene. Similarly, any unreacted olefin or organic hydroperoxide may be separated and recycled. After separating from the epoxidation reaction mixture, the recovered catalyst may be economically re-used in subsequent epoxidations.

Glycidyl Ether Epoxides

In general, the process of the present invention is useful for making aryl glycidyl ether epoxies. A specific example of an aryl glycidyl ether made by the process of the present invention includes 4,4'-bisphenol A diglycidyl ether.

In one embodiment of the present invention, the aryl glycidyl ethers made by the process of the present invention are represented by, but are not limited to, the structures of the following Formula X:

  Formula X.

In Formula X, x is from 0 to 750, y is from 0 to 750; and z is from 1 to 150.

Ar is a moiety containing a mononuclear aromatic ring such as phenyl. Ar may also be a moiety containing multinuclear aromatic rings, such as biphenyl, 2,2-diphenyl propane, bisphenylene oxide, tetrakis(1,1,2,2-phenyl) ethane, and stilbene. Also included are examples having multinuclear aromatic rings, such as phenol-formaldehyde novolac, cresol-formaldehyde novolac, phenol-dicyclopentadiene novolac, and hyper-branched aromatic phenol dendrimers. Ar may also be a moiety containing multinuclear fused aromatic rings such as naphthalene, anthracene, and naphthalene-formaldehyde novolac. Ar may also be a moiety containing multinuclear fused aromatic rings with one or more heteroatoms such as O, N, S, Si, B or P, or any combination of these heteroatoms, for example, quinoxaline, thiophene, and quinoline. Ar may also be a moiety containing mononuclear or multinuclear aromatic rings fused with a cycloaliphatic ring(s) such as indane, 1,2,3,4-tetrahydronaphthalene, and fluorene. Ar may also be a moiety containing mononuclear or multinuclear aromatic rings fused with a cycloaliphatic ring(s) containing one or more heteroatoms such as O, N, S, Si, B or P, or any combination of these heteroatoms, for example, chroman, indoline, and thioindane. Ar as described in Formula I can also be partially or fully fluorinated.

Ar can also be a moiety containing aryl groups in which each aryl group is connected to oligomeric (for example, less than 5000 molecular weight average) or high molecular weight (for example, greater than 5000 molecular weight average) organosiloxane units. The aryl groups are attached directly to the Si atoms of the organosiloxane units, or the aryl groups are indirectly attached to the Si atoms of the organosiloxane units via an organic aliphatic moiety, organic cycloaliphatic moiety, organic aromatic moiety, or any combination thereof. The organic aliphatic, cycloaliphatic, or aromatic moiety should contain no more than 20 carbon atoms. When the Ar moiety contains such oligomeric or high molecular weight organosiloxane units then z is preferably from 1 to 150.

In one embodiment of the present invention, the glycidyl ether-containing aromatic ring(s) of the Ar moiety in Formula X is conformationally restricted. The glycidyl ether-containing aromatic ring(s) of the Ar moiety in Formula X is conformationally restricted because (a) the free rotation of the glycidyl ether containing aromatic ring(s) of the Ar moiety is being restricted due to the close proximity of atoms on the glycidyl ether-containing aromatic ring(s) of the Ar moiety to adjacent aromatic ring(s), which may or may not contain a glycidyl ether group(s), of the Ar moiety providing a crowded spacing of the atoms which limits the mobility of the glycidyl ether-containing aromatic ring(s) of the Ar moiety and therefore limits the mobility of the glycidyl ether group(s) $OR^4$, for example, such as in the case where Ar is biphenyl; (b) the free rotation of the glycidyl ether-containing aromatic ring(s) of the Ar moiety is being restricted due to the presence of a rigid segment such as $-CH=CR^5-$, an amide group, and an ester group, linking the glycidyl ether-containing aromatic ring(s) to another aromatic ring, which may or may not contain a glycidyl ether group(s), of the Ar moiety which limits the mobility of the glycidyl ether-containing aromatic ring(s) of the Ar moiety and therefore limits the mobility of the glycidyl ether group(s) $OR^4$ or; (c) the free rotation of the $OR^4$ group(s) on the aromatic ring(s) of the Ar moiety is restricted by the presence of at least one or more bulky, sterically hindering $R^1$ groups, other than hydrogen, ortho to the $OR^4$ group(s). Advantageously, in such instance, the yield of glycidyl ether epoxy and the selectivity of hydroperoxide are usually higher.

In Formula X, $R^1$ is a group substituted for the hydrogen atom at a position that is ortho to the $OR^4$ group(s) on the aromatic ring(s) of the Ar moiety. $R^1$ is halogen such as bromo, and chloro; or a hydrocarbon radical such as an alkyl group, cycloaliphatic group or aromatic group. $R^1$ is preferably an alkyl group having from 1 to 20 carbon atoms, such as methyl, ethyl, or isopropyl; a cycloaliphatic group having from 3 to 20 carbon atoms such as cyclopentyl, and cyclohexyl; or an aromatic group having from 6 to 20 carbon atoms such as phenyl, and naphthyl; or any combination thereof. The hydrocarbon radicals above may also contain one or more heteroatoms, such as O, N, S, Si, B or P, or any combination of these heteroatoms. An example of a hydrocarbon radical containing an O heteroatom is a methoxy group, an ethoxy group or a polyalkylene oxide group derived from ethylene oxide, propylene oxide, butylene oxide and cyclohexene oxide or the like. $R^1$ as described above in Formula X can be partially or fully fluorinated.

In one preferred embodiment, there are at least one or more $R^1$ substituents in the position(s) ortho to the $OR^4$ group(s) on the aromatic ring(s) of the Ar moiety. In this preferred embodiment the glycidyl ether(s) $OR^4$ is conformationally restricted because the free rotation of the $OR^4$ group(s) on the aromatic ring(s) of the Ar moiety is restricted by the presence of at least one or more $R^1$ groups on the ortho position(s) ortho to the $OR^4$ group(s) on the aromatic ring(s) of the Ar moiety. Advantageously, in such instance, the yield of glycidyl ether epoxy and the selectivity of hydroperoxide are usually higher than those glycidyl ether epoxies without $R^1$ groups(s) in the position(s) ortho to the $OR^4$ group(s).

In Formula X, $R^2$ is a group substituted for a hydrogen atom at a position(s) that is not ortho to the $OR^4$ group(s) on the aromatic ring(s) of the Ar moiety. $R^2$ is a halogen such as bromo, and chloro; or a hydrocarbon radical such as an alkyl group, a cycloaliphatic group or aromatic group. $R^2$ is preferably an alkyl group having from 1 to 20 carbon atoms such as methyl, ethyl, and propyl; a cycloaliphatic group having from 3 to 20 carbon atoms such as cyclopentyl, and cyclohexyl; or an aromatic group having from 6 to 20 carbon atoms such as phenyl, and naphthyl; or any combination thereof. The hydrocarbon radicals above may also contain one or more heteroatoms such as O, N, S, Si, B or P, or any combination of these heteroatoms. An example of a hydrocarbon radical containing an O heteroatom is a methoxy group, an ethoxy group or a polyalkylene oxide group derived from ethylene oxide, propylene oxide, butylene oxide and cyclohexene oxide or the like. $R^2$ as described above in Formula X can be partially or fully fluorinated.

In Formula X, $OR^4$ is an epoxide-containing oxy group substituted for a hydrogen atom on the aromatic ring(s) of the Ar moiety, where $R^4$ is an epoxide-containing moiety selected from:

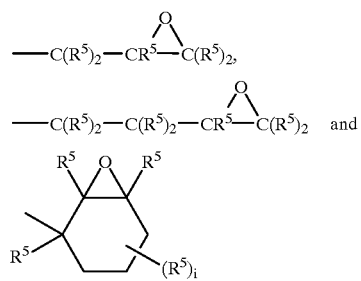

where $R^5$ is hydrogen; or an alkyl group, a cycloaliphatic group or aromatic group; and i is from 0 to 6. $R^5$ is preferably an alkyl group having from 1 to 20 carbon atoms such as methyl, ethyl, and propyl; a cycloaliphatic group having from 3 to 20 carbon atoms such as cyclopentyl, and cyclohexyl; or an aromatic group having from 6 to 20 carbon atoms such as phenyl, and naphthyl; or any combination thereof. Each individual $R^5$ may be the same group or may be a different group from each other.

$R^4$ may also be a monoalkylene oxide group or a polyalkylene oxide group derived from ethylene oxide, propylene oxide, butylene oxide, cyclohexene oxide or the like, wherein each monoalkylene oxide group and each polyalkylene oxide group is terminated with an epoxide-containing moiety selected from:

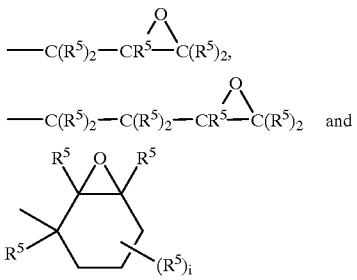

where $R^5$ is as described above.

In one embodiment, when $R^4$ in Formula X is

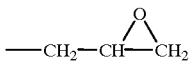

the ether is an "aryl glycidyl ether."

In another embodiment, when $R^4$ in Formula X is

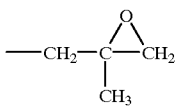

the ether is an "aryl methylglycidyl ether."

In yet another embodiment, when $R^4$ in Formula X is

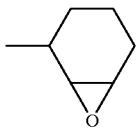

the ether is an "aryl 2,3-epoxycyclohexan-1-yl ether."

More specific and preferred examples of aryl glycidyl ether epoxies prepared by the process of the present invention are represented by the following Formulas XI–XIV.

Examples of mononuclear aryl glycidyl ether epoxies prepared by the process of the present invention are represented by the following Formula XI:

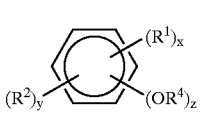

Formula XI

In Formula XI, $R^1$, $R^2$, $OR^4$ and $R^4$ have the same meaning as described above with reference to Formula X. In Formula XI, x is from 0 to 4, y is from 0 to 3 and z is from 1 to 4.

Examples of "aryl glycidyl ethers" and "aryl methylglycidyl ethers" represented by Formula XI include, for example, 2,6-dimethylphenyl glycidyl ether; 2,6-dimethylphenylmethylglycidyl ether; 4-methyl-2,6-dibromophenyl methylglycidyl ether; and 1,4-, 1,5- or 2,6-naphthalene diglycidyl ethers.

Other examples of aryl glycidyl ethers prepared by the process of the present invention are binuclear aryl glycidyl ethers which are represented by the following Formula XII:

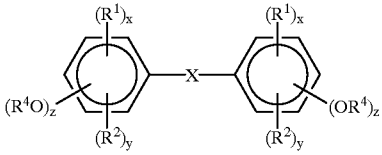

Formula XII

In Formula XII, $R^1$, $R^2$, $OR^4$ and $R^4$ have the same meaning as described above with reference to Formula X. In Formula XII, each x is from 0 to 3 and each x can be the same or different, each y is from 0 to 2 and each y can be the same or different, and each z is from 1 to 2 and each z can be the same or different.

In Formula XII, X may be nil; or X can be a heteroatom with or without substituents thereon to complete its necessary bonding valance; the heteroatom is selected from O, N, S, Si, B or P, or any combination of two or more of the above heteroatoms; X can also be, for example, —C(O)—; —S(O$_2$)—, —C(O)—NH—; —P(O)Ar—; an organic aliphatic moiety, with or without heteroatoms, such as, for example, oxydimethylene, methylene, 2,2-isopropylidene, isobutylene, and —CR$^5$=CH— where $R^5$ is defined above in Formula X; a cycloaliphatic group, with or without heteroatoms, such as, for example, a cycloaliphatic ring with greater than 3 carbon atoms; or an aromatic group, with or without heteroatoms; or any combination thereof, preferably with no more than 60 carbon atoms. X as described above in Formula XII can be partially or fully fluorinated, such as, for example, 2,2-perfluoroisopropylidene.

Examples of "aryl glycidyl ethers" and "aryl methyl glycidyl ethers" represented by Formula XII include, for example, 4,4'-bisphenol A diglycidyl ether; 4,4'-(3,3',5,5'-tetramethyl)bisphenol A diglycidyl ether; 4,4'-(3,3',5,5'-tetrabromo)bisphenol A diglycidyl ether; 4,4'-(3,3',5,5'-tetramethyl-2,2',6,6'-tetrabromo)bisphenol A diglycidyl ether; 4,4'-(3,3',5,5'-tetramethyl)bisphenol F diglycidyl ether; 4,4'-bisphenol F diglycidyl ether 4,4'-bisphenol sulfone diglycidyl ether; 4,4'-bisphenol K diglycidyl ether; 4,4'-(3,3'5,5'-tetramethyl-2,2',6,6'-tetrabromobiphenol) diglycidyl ether; 9,9-bis(4-glycidyloxyphenyl)fluorene; 4,4'-biphenol diglycidyl ether; 4,4'-(3,3',5,5'-tetramethylbiphenol)diglycidyl ether; 4,4'-dihydroxy-α-methylstilbene diglycidyl ether; 1,3-bis(4-glycidyloxyphenyl)adamantane; 4,4'-bisphenol A dimethylglycidyl ether; 4,4'-(3,3',5,5'-tetramethyl)bisphenol A dimethylglycidyl ether; 4,4'-(3,3',5,5'-tetrabromo) bisphenol A dimethylglycidyl ether; 4,4'-(3,3',5,5'-tetramethyl-2,2',6,6'-tetrabromo)bisphenol A dimethylglycidyl ether; 4,4'-(3,3',5,5'-tetramethyl)bisphenol F dimethylglycidyl ether; 4,4'-bisphenol F dimethylglycidyl ether; 4,4'-bisphenol sulfone dimethylglycidyl ether; 4,4'-bisphenol K dimethylglycidyl ether; 4,4'-(3,3'5,5'-tetramethyl-2,2',6,6'-tetrabromobiphenol)dimethylglycidyl ether; 9,9-bis(4-methylglycidyloxyphenyl)fluorene; 4,4'-biphenol dimethylglycidyl ether; 4,4'-(3,3',5,5'-tetramethylbiphenol)dimethylglycidyl ether; 4,4'-dihydroxy-α-methylstilbene dimethylglycidyl ether; and 1,3-bis(4-methylglycidyl-oxyphenyl)adamantane.

Other examples of aryl glycidyl ethers prepared by the process of the present invention are multi-nuclear aryl glycidyl ethers which are represented by the following Formula XIII:

Formula XIII

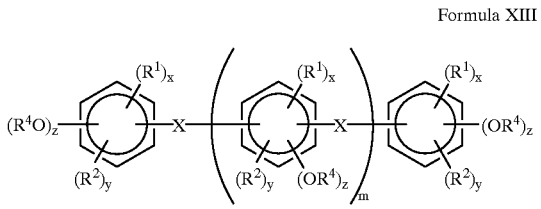

In Formula XIII, $R^1$, $R^2$, $OR^4$, $R^4$, and X have the same meaning as described above with reference to Formula XII. In Formula XIII, each x is from 0 to 3 and each x can be the same or different, each y is from 0 to 3 and each y can be the same or different, and each z is from 1 to 2 and each z can be the same or different. In Formula XIII m is from 0.001 to 10.

Examples of "aryl glycidyl ethers" and "aryl methylglycidyl ethers" represented by Formula XII include, for example, glycidyl ether of o-cresol-formaldehyde novolac (functionality greater than 2), glycidyl ether of phenol-formaldehyde novolac (functionality greater than 2), glycidyl ether of phenol-dicyclopentadienyl novolac (functionality greater than 2), glycidyl ether of naphthol-formaldehyde novolac (functionality greater than 2), methylglycidyl ether of o-cresol-formaldehyde novolac, methylglycidyl ether of phenol-formaldehyde novolac, methylglycidyl ether of phenol-dicyclopentadienyl novolac, and methylglycidyl ether of naphthol-formaldehyde novolac.

Other examples of aryl glycidyl ethers prepared by the process of the present invention are multi-nuclear aryl glycidyl ethers which are represented by the following Formula XIV:

Formula XIV

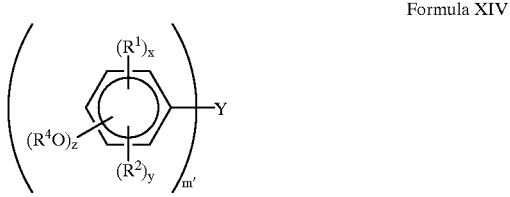

In Formula XIV, $R^1$, $R^2$, $OR^4$ and $R^4$ have the same meaning as described previously with reference to Formula XIII. In Formula XIV, each x is from 0 to 3 and each x can be the same or different, each y is from 0 to 3 and each y can be the same or different, and each z is from 1 to 2 and each z can be the same or different.

In Formula XIV, Y is an organic aliphatic moiety, with or without heteroatoms such as, O, N, S, Si, B or P, or any combination of two or more of the above heteroatoms, wherein the aliphatic moiety has from 1 to 20 carbon atoms, such as, for example, methine; a cycloaliphatic moiety, with or without heteroatoms, having from 3 to 20 carbon atoms such as, for example, cyclohexanetriyl; an aromatic moiety, with or without heteroatoms, such as, for example, benzenetriyl, naphthylenetriyl, or fluorenetriyl; or any combination thereof, with no more than 20 carbon atoms. Y as described above in Formula XIV can be partially or fully fluorinated such as fluoromethane.

In Formula XIV, m' is generally 3 or 4. However, Y may also be an oligomeric or high molecular weight organosiloxane unit. In which case, the aryl groups are attached to the Si atoms of the organosiloxane unit directly or indirectly through an organic aliphatic, cycloaliphatic, aromatic group, or any combination thereof, with no more than 20 carbon atoms. Thus, m' in Formula XIV is from 1 to 150.

Examples of "aryl glycidyl ethers" and "aryl methylglycidyl ethers" represented by Formula XIV include, for example, trisphenylol methane triglycidyl ether; tris(2,6-dimethylphenylol)methane triglycidyl ether; 1,1,2,2-tetraphenylol ethane tetraglycidyl ether; trisphenylol methane trimethylglycidyl ether; tris(2,6-dimethylphenylol) methane trimethylglycidyl ether; and 1,1,2,2-tetraphenylol ethane tetramethyl glycidyl ether.

In another embodiment of the present invention, the glycidyl ethers in Formulas XI to XIV above, are conformationally restricted by the presence of at least one or more $R^1$ group(s) such as methyl, ethyl, isopropyl, phenyl or halogen, such as a bromo group on the aromatic rings in the position(s) ortho to the $OR^4$ group(s). In such an instance, the yield of glycidyl ether epoxy and the selectivity of hydroperoxide are very high compared to those of aryl glycidyl ethers without $R^1$ group(s) in the position(s) ortho to the $OR^4$ group(s). For example such steric hindrance can be found in the case of 2,6-diisopropylphenyl glycidyl ether.

In other preferred embodiments of the present invention, in Formula XII to XIV above, there is either the close proximity of atoms on aromatic ring(s) adjacent to the aryl glycidyl ether-containing aromatic ring(s) providing a crowded spacing of the atoms which limits the mobility of the aryl glycidyl ether group(s); or there is a rigid moiety linking the glycidyl ether-containing aromatic ring(s) of the aryl glycidyl ether structure to another aromatic ring which limits the mobility of the aryl glycidyl ether structure. In both instances, the allyl ether conversion, the epoxidation yield, and the selectivity of hydroperoxide are very high compared to those of aryl allyl ethers without the effect of the crowded spacing of atoms or without the effect of a rigid moiety linking aromatic rings.

It is theorized when such conformationally restricted aryl glycidyl ethers are formed that the interaction between the epoxide of an aryl glycidyl ether and the transition metal of the transition metal catalyst, which may lead to the hydrolysis of the epoxide to form the undesired hydrolyzed glycol is impeded.

The epoxy resins prepared by the process of the present invention are useful in applications such as, for example, electrodeposition coatings, powder coatings, automotive paints, industrial and civil engineering paints, electrical encapsulants, molding, casting, composites, laminates, and adhesives.

The epoxy resins prepared by the process of the present invention based on aromatic hydroxyl-containing compounds, for example, those based on cresol-formaldehyde novolac resins are particularly useful in the preparation of electrical laminates and encapsulated electronic components, cathodic electrodeposition and powder coatings since halogen atoms are known to be undesirable components in epoxy resins used in these applications.

From the foregoing description, one skilled in the art can readily ascertain the essential characteristics of the present invention, and, without departing from the spirit and scope of the present invention, can make various changes and modifications of the present invention to adapt it to various usages, conditions and embodiments.

The following examples further illustrate the process of the present invention, but are not intended to limit the present invention in any manner whatsoever.

EXAMPLES 1 TO 9

In Examples 1 to 9, various aryl monoallyl ethers described in Table I below were epoxidized using the following general procedure:

To a four-necked, glass reactor equipped with a cooling condenser, a thermometer, a magnetic stirrer, a nitrogen inlet, and a heating lamp with thermo-controller, was added a mixture of aryl allyl ether, tetrachloroethane solvent, and tert-butylhydro-peroxide (TBHP; 3 molar (M) in isooctane, anhydrous grade, water content less than 800 parts per million (ppm)). A catalyst, $Mo(CO)_6$, was added at ambient temperature under a nitrogen atmosphere. The amount of aryl allyl ether used was 0.05 mole. The molar ratio of aryl allyl ether to TBHP was 1:1.1. The amount of $Mo(CO)_6$ catalyst used was 2.5 mole percent based on the amount of allyl ether used. The amount of tetrachloroethane was 30 milliliters (mL). The reaction was carried out at 65° C. for 8 hours (hr). After the reaction was completed, the reaction mixture was analyzed by gas chromatography (GC)/mass spectrometry (MS) for unreacted aryl alkyl ether, for glycidyl ether epoxy and for hydrolyzed epoxy that is, a glycol impurity.

Experimental results for Examples 1 to 9 are described in Table I below, wherein the "Epoxide Yield, %" and the "TBHP Conv. (conversion), %" are based on GC peak area. In Table I, the "TBHP Sel. (selectivity), %" is the "Epoxide Yield, %" divided by "TBHP Conv., %."

The $R^1$, $R^2$ and $R^3$ groups described in Table I are based on the reaction illustrated by the following general equation:

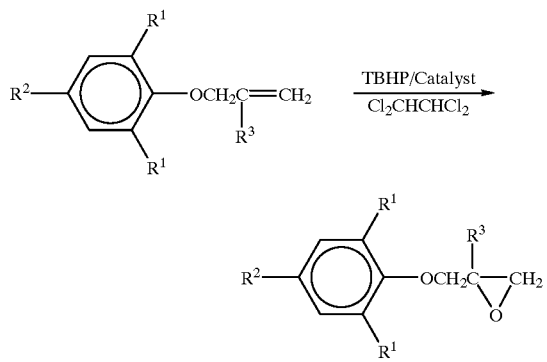

TABLE I

| Example | Substituents $R^1$, $R^2$, $R^3$ | Epoxide Yield, % | TBHP Conv. (Sel.), % | Epoxide Yield, %* |
|---|---|---|---|---|
| Example 1 | $R^1$, $R^2$ = H; $R^3$ = methyl | 60 | 82(73) | |
| Example 2 | $R^1$, $R^3$ = methyl; $R^2$ = H | 75 | 80(94) | >90 |
| Example 3 | $R^1$ = isopropyl; $R^3$ = methyl; $R^2$ = H | >90 | 92(>98) | >95 |
| Example 4 | $R^1$ = bromo; $R^3$ = methyl; $R^2$ = H | 85 | 88(97) | >90 |
| Example 5 | $R^1$, $R^2$, $R^3$ = H | 12 | 90(13) | |
| Example 6 | $R^1$ = methyl; $R^2$, $R^3$ = H | 38 | 73(52) | |
| Example 7 | $R^1$ = isopropyl; $R^2$, $R^3$ = H | 47 | 83 (57) | |
| Example 8 | $R^1$ = t-butyl; $R^2$, $R^3$ = H | 27 | 63(43) | |
| Example 9 | $R^1$ = bromo; $R^2$, $R^3$ = H | 39 | 69(57) | |

*In these experiments, additional TBHP was added after the initial TBHP was consumed to bring the total molar ratio of TBHP to aryl allyl ether used to 1.6:1.

The above results of Examples 2 to 4 compared to Example 1 and Examples 6 to 9 compared to Example 5 in Table I show that glycidyl ethers, which are conformationally restricted because the free rotation of the aromatic rings of the glycidyl ether is being restricted due to the different substituents at both positions ortho to the $OR^4$ substituent, are produced in higher yield with greater TBHP selectivities. It was found that substituent size has a dramatic affect on epoxidation yield and purity of the final "methylglycidyl ether" epoxy product in Examples 1 to 4 in Table I. For example, placing methyl, isopropyl and bromo groups at both positions on the aromatic ring ortho to the $OR^4$ groups, achieved 75 percent to 90 percent epoxidation yields and a TBHP selectivity of greater than 90 percent as shown in Table I, Examples 2 to 4. At the same time in Examples 2 to 4, the amount of impurity hydrolyzed epoxide product is from less than 1 percent to 3 percent.

Improvements were also observed in epoxidation yield of the final "glycidyl ether" epoxy product as shown in Table I, Examples 6 to 9. For example, placing methyl, isopropyl, tert-butyl and bromo groups at both positions on the aromatic ring ortho to the $OR^4$ groups, achieved a two to four fold improvement in the epoxidation yields and a three to four fold improvement in the TBHP selectivity as shown in Table I in Examples 5 to 9.

Similar results were also observed when diglycidyl ethers of Formula XII were synthesized as shown in Table II. When conformationally restricted diallyl ethers of biphenol(s) were used, such as in the examples in Table II, not only was the epoxidation yield improved, but also the total amount of the diglycidyl ether diepoxides was increased.

EXAMPLES 10 TO 18

Examples 10 to 18 in Table II were carried out as in Examples 1 to 9 except that aryl bisallyl ethers and bismethallyl ethers were used as the substrates. The amount of aryl bis(meth)allyl ether used was 0.025 mole. The molar ratio of aryl bis(meth)allyl ether to the TBHP was 1:2.2. The amount of $Mo(CO)_6$ catalyst was 5 mole percent based on the amount of aryl bis(meth)allyl ether used. The amount of tetrachloroethane was 50 mL. The reaction was carried out at 65° C. for a period of from 6 to 20 hours wherein two or more reaction samples were analyzed after the time indicated in Table II. The reaction mixture was analyzed by high pressure liquid chromatography (HPLC) and the product structure was confirmed by gas chromatography/mass spectrometry. In Examples 11 to 15, and Example 17, when the reaction rate became very slow, an additional amounts of TBHP were added after the initial TBHP was consumed to bring the total molar ratio of TBHP to aryl allyl ether used to 3.2:1. Then, the reactions were continued until the rates became very slow once again.

The results for Examples 10 to 18 are shown in Table II, where the aryl di(methyl)glycidyl ether diepoxide ("Di-E, %") to aryl mono(methyl)glycidyl ether monoepoxide ("Mono-E, %") to aryl bis(meth)allyl ether ("Bis-AE, %") ratio ("Di-E, %:Mono-E, %:Bis-AE, %") is based on the peak areas measured by HPLC. The total epoxide yield ("TEY, %") is calculated as follows:

$$TEY, \% = [(2 \times \text{peak area of } Di\text{-}E) + \text{peak area of } Mono\text{-}E] \div 2 \times [(\text{peak area of } Di\text{-}E) + (\text{peak area of } Mono\text{-}E) + (\text{peak area of } Bis\text{-}AE)]$$

The reaction in these examples using the substrates described in Table II is illustrated in general form by the following equation:

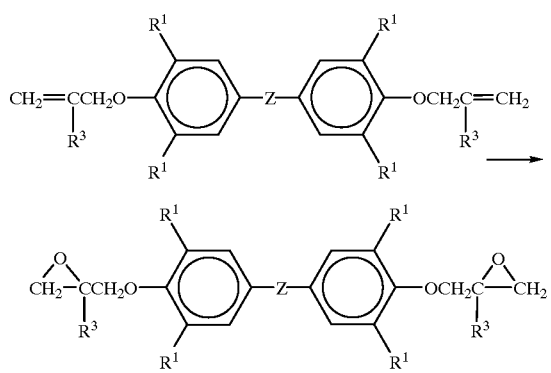

TABLE II

| Example | Substrate | Reaction Time, hours | Di-E %:Mono-E %:Bis-AE % (TEY, %) |
|---|---|---|---|
| 10 | $R^1$ = H; $R^3$ = methyl; Z = isopropylidene | 16 | 46:43:11 (68) |
| 11 | $R^1$ = $R^3$ = methyl; Z = isopropylidene | 16 | 58:36:6 (76) |
|  |  | 20* | 74:23:3 (86) |
| 12 | $R^1$ = H; $R^3$ = methyl; Z = nil | 8 | 29:4:22 (54) |
|  |  | 16* | 56:37:6 (75) |
| 13 | $R^1$ = $R^3$ = methyl; Z = nil | 8 | 23:51:26 (48) |
|  |  | 12 | 26:52:10 (52) |
|  |  | 20* | 53:40:7 (72) |
| 14 | $R^1$ = isopropyl; $R^3$ = methyl; Z = nil | 6 | 38:47:15 (62) |
|  |  | 12* | 72:26:2 (85) |
| 15 | $R^1$ = $R^3$ = H; Z = isopropylidene | 8 | 6:36:58 (24) |
|  |  | 16* | 9:39:51 (29) |
| 16 | $R^1$ = methyl; $R^3$ = H; Z = isopropylidene | 8 | 12:46:42 (35) |
|  |  | 16 | 24:52:24 (50) |
| 17 | $R^1$ = Br; $R^3$ = H; Z = isopropylidene | 8 | 9:41:50 (30) |
|  |  | 16* | 15:48:37 (39) |
| 18 | $R^1$ = isopropyl; $R^3$ = H; Z = isopropylidene | 8 | 9:42:49 (30) |
|  |  | 16 | 23:53:28 (48) |

*Additional TBHP was added to bring the mole ratio of TBHP:aryl bisallyl ether to 3.2:1

The above results in Table II show that, when glycidyl ethers which were conformationally restricted because the free rotation of the aromatic rings of the glycidyl ether was being restricted due to the close proximity of the hydrogen atoms on aromatic rings adjacent to the glycidyl ether-containing aromatic rings providing a crowded spacing of the atoms which limited the mobility of the glycidyl ether structure, in such instances, the yields of glycidyl ether epoxies were usually high as shown in Examples 11, 13, and 14, and Examples 16 to 18 in Table II above.

EXAMPLES 19 TO 32

In Examples 19 to 32, various catalysts with different ligands, such as cyclopentadienyl(Cp) and DPPE (diphenylphosphinylethane), were used for epoxidation of aryl methallyl ethers using the same general procedure as described in Examples 1 to 9, except that the amount of catalyst was varied and the reaction was run at various temperatures as shown in Table III. The results of Examples 19 to 32 are described in Table III.

The $R^1$, $R^2$ and $R^3$ groups described in Table III below are based on the reaction as illustrated by the following general equation:

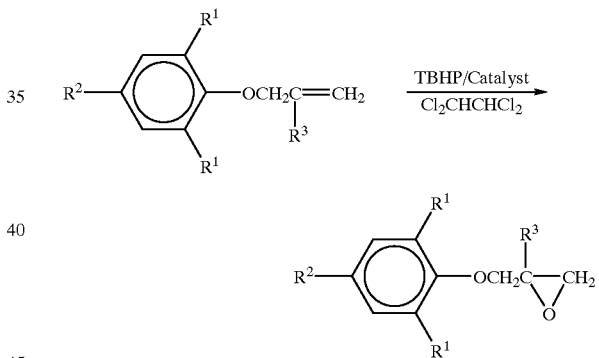

TABLE III

| Example | Catalyst | Catalyst, Mole % | Temperature, °C. | Reaction Time, hour | Epoxide Yield, % | TBHP Conv., % | TBHP Sel., % |
|---|---|---|---|---|---|---|---|
| 19[1] | Mo(CO)$_6$ | 2.5 | 65 | 8 | 57 | 82 | 70 |
| 20[1] | MoCp$_2$Cl$_2$ | 1.25 | 60 | 8 | 52 | 75 | 69 |
| 21[1] | [CpMo(CO)$_2$]$_2$ | 1.25 | 40 | 8 | 42 | 49 | 86 |
| 22[2] | MoO$_2$Cl$_2$ | 2.5 | 65 | 2 | 64 | 82 | 78 |
| 23[2] | MoCp$_2$Cl$_2$ | 1.25 | 65 | 4 | 57 | 75 | 76 |
| 24[2] | MOCp$_2$Cl$_2$ | 1.25 | 55 | 8 | 57 | 75 | 76 |
| 25[1] | (DPPE)Mo(CO)$_4$ | 1.25 | 55 | 7 | 54 | 80 | 68 |
| 26[1] | Cp(CO)(DPPE)MoCl | 1.25 | 55 | 8 | 55 | 84 | 65 |
| 27[1] | MoO$_2$Cl$_2$.Pyrazole | 1.25 | 55 | 7 | 52 | 77 | 68 |
| 28[1] | MoO$_2$(AcAc)$_2$ | 1.25 | 55 | 5 | 50 | 81 | 62 |
| 29[1] | MoO$_2$Cl$_2$ + NaOSi(CH$_3$)$_3$ | 1.25 | 55 | 10 | 54 | 71 | 76 |
| 30[3] | Mo(CO)$_6$ | 1.25 | 65 | 8 | 81 | 99 | 85 |
| 31[3] | MOCp$_2$Cl$_2$ | 1.25 | 65 | 8 | 82 | 85 | 95 |
| 32[3] | MoO$_2$(AcAc)$_2$ | 1.25 | 65 | 8 | 77 | 80 | 96 |

[1]Examples 19–21, 25–29: $R^1$ = H; $R^2$ = tert-butyl; $R^3$ = methyl.

TABLE III-continued

| Example | Catalyst | Catalyst, Mole % | Temperature, °C. | Reaction Time, hour | Epoxide Yield, % | TBHP Conv., % | TBHP Sel., % |
|---|---|---|---|---|---|---|---|

[2]Examples 22–24: $R^1$ = methyl; $R^2$ = H; $R^3$ = methyl.
[3]Examples 30–32: R = isopropyl; $R^2$ = H; $R^3$ = methyl.

COMPARATIVE EXAMPLES A AND B

In Comparative Examples A and B, aryl monoallyl ethers with structures described in Table IV below were epoxidized using the process described in U.S. Pat. No. 5,633,391 as follows:

To a four-necked, glass reactor equipped with a cooling condenser, a thermometer, a magnetic stirrer, a nitrogen inlet, and a heating lamp with thermo-controller, was added 8.8 g (0.06 mole) of bis(trimethylsilyl)peroxide, 50 g of tert-amyl alcohol, and 0.32 g methyltrioxide rhenium (MTO, 2.5 mole percent based on monoallyl ether) which were stirred at ambient temperature under a nitrogen atmosphere for 5 minutes. Then 0.05 mole of the monoallyl ether was added into the reactor. The molar ratio of aryl allyl ether to oxidant was 1:1.2. The reaction was carried out at 25° C. for 5 to 8 hours. After the reaction was completed, the reaction mixture was analyzed by gas chromatography (GC)/mass spectrometry (MS) for unreacted aryl alkyl ether, for glycidyl ether epoxy and for hydrolyzed epoxy that is, a glycol impurity.

Experimental results for Comparative Examples A and B are described in Table IV below, wherein the "Epoxide Yield, %" and "Impurity Glycol Yield, %" are based on GC peak area.

The $R^1$, $R^2$ and $R^3$ groups described in Table IV below are based on the reaction as illustrated by the following general equation:

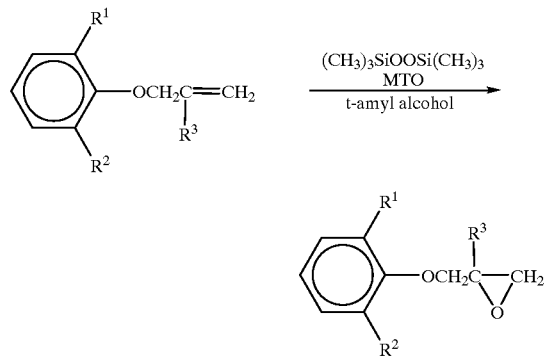

TABLE IV

| Comparative Example | Substituents $R^1$, $R^2$, $R^3$ | Epoxide Yield, % | Impurity Glycol Yield, % |
|---|---|---|---|
| Comparative Example A | $R^1$, $R^3$ = methyl; $R^2$ = H | 58* | 12 |
| Comparative Example B | $R^1$, $R^2$, $R^3$ = H | <1 | 9 |

*All of the epoxide decomposed after standing at ambient temperature for 3 days.

Comparative Examples A and B in Table IV show that the oxidant-catalyst system described in U.S. Pat. No. 5,633,391 had a deleterious affect on epoxidation yield and purity of the final glycidyl ether epoxy product.

In Comparative Example A, in which bis(trimethylsilyl) peroxide and methyltrioxide rhenium were used, before product finishing, the epoxide yield was only 58 percent and there was 12 percent hydrolyzed glycol impurity. After finishing and standing at ambient temperature for three days, the Comparative Example A reaction product decomposed and all of the epoxide disappeared. In comparison, in Example 2 in Table I, the epoxide yield was 75 percent without significant impurity glycol present; and after finishing and standing at ambient temperature for several months, there was no sign of epoxide decomposition in Example 2 product. These two results indicate that higher valence catalysts such as methyltrioxide rhenium are very acidic causing the hydrolysis of the epoxide both during the epoxidation reaction and after the epoxidation product is finished.

Results similar to those described above for Comparative Example A and Example 2 were obtained when Comparative Example B and Example 5 were compared.

COMPARATIVE EXAMPLES C–F

Prior to beginning the epoxidation reaction, in the following Comparative Examples C to F, 12.5 mole percent and 25 mole percent of 3-phenoxy-1,2-dihydroxypropane (Comparative Example C and D) or 12.5 mole percent and 25 mole percent of 1,2-propanediol (Comparative Example E and F) based on phenyl allyl ether as shown in Table V below, were added to an epoxidation reaction mixture including an aryl allyl ether and TBHP. The general procedure used in Comparative Examples C to F was as follows:

To a four-necked, glass reactor equipped with a cooling condenser, a thermometer, a magnetic stirrer, a nitrogen inlet, and a heating lamp with thermo-controller, was added glycol (as shown in the following Table V), 0.05 mole of 2,6-dimethyl phenyl methallyl ether, $1.25 \times 10^{-3}$ $Mo(CO)_6$ and 50 g of tetrachloroethane at ambient temperature under a nitrogen atmosphere. After mixing for 30 minutes at 65° C., the reaction mixture was cooled to ambient temperature and 0.06 mole of TBHP was added into the reactor. The molar ratio of aryl methallyl ether to oxidant was 1:1.2. The amount of $Mo(CO)_6$ catalyst used was 2.5 mole percent based on the amount of methallyl ether used. The reaction was carried out at 65° C. for 4 hours. After the reaction was completed, the reaction mixture was analyzed by gas chromatography (GC)/mass spectrometry (MS). Experimental results for Comparative Examples C to F are described in Table V below, wherein the "Epoxide Yield, percent" is based on the GC peak area.

TABLE V

| Example | Glycol Added to the Epoxidation Reaction Mixture | Epoxide Yield, % |
|---|---|---|
| Example 2 | none | 60 |
| Comparative Example C | 3-phenoxy-1,2-dihydroxypropane | <2 |

TABLE V-continued

| Example | Glycol Added to the Epoxidation Reaction Mixture | Epoxide Yield, % |
|---|---|---|
| Comparative Example D | 3-phenoxy-1,2-dihydroxypropane | <20 |
| Comparative Example E | 1,2-propanediol | <5 |
| Comparative Example F | 1,2-propanediol | <10 |

Comparative Examples C and D show that the addition of 3-phenoxy-1,2-dihydroxypropane to the epoxidation reaction mixture, immediately caused the deactivation of the molybdenum catalyst, and there was low yield of glycidyl ether. Comparative Examples E and F show the similar deactivation effect of the glycol. When adding 1,2-propanediol to the epoxidation reaction mixture, the molybdenum catalyst was also deactivated and there was low yield of glycidyl ether.

The results of Comparative Examples C to F, when compared to Example 2 of this present invention, illustrate the hypothesis that deactivation of an epoxidation catalyst was caused by the formation of hydrolyzed glycol of an aryl glycidyl ether during the epoxidation process. It is further hypothesized that the formation of glycol is through the interaction of the aryl glycidyl ether with the transition metal catalyst, and that the use of a conformationally restricted aryl allyl ether impedes or prevents the formation of hydrolyzed glycol.

What is claimed is:

1. A process for making an aromatic glycidyl ether epoxy compound comprising contacting an aryl allyl ether with a hydroperoxide oxidant in the presence of a transition metal complex catalyst, wherein at least (a) the aryl allyl ether is conformationally restricted; or (b) the transition metal complex catalyst contains at least one or more stable ligands attached to the transition metal.

2. The process of claim 1 wherein the aryl allyl ether is conformationally restricted.

3. The process of claim 2 wherein the aryl allyl ether is conformationally restricted due to the presence of atomic spacings which limit the mobility of the aryl allyl ether structure.

4. The process of claim 2 wherein the aryl allyl ether is conformationally restricted due to the presence of a rigid segment linking the aromatic rings, of which at least one is an aryl allyl ether moiety, which limits the mobility of the aryl allyl ether structure.

5. The process of claim 2 wherein the aryl allyl ether is conformationally restricted due to the presence of at least one substituent on the aromatic ring(s) of the aryl allyl ether in a position ortho to the allyl ether group(s) which sterically hinders or restricts the freedom of rotation of the allyl ether group(s).

6. The process of claim 1 wherein the transition metal complex catalyst contains at least one or more stable ligands attached to the transition metal.

7. The process of claim 1 wherein the aryl allyl ether is conformationally restricted and the transition metal complex catalyst contains at least one or more stable ligands attached to the transition metal.

8. A process for making a multi-functional, aryl glycidyl ether epoxy compound comprising contacting a multifunctional aryl allyl ether of aryl phenol with an hydroperoxide oxidant in the presence of a transition metal complex catalyst.

9. The process of claim 8 wherein at least (a) the multifunctional aryl allyl ether is conformationally restricted or (b) the transition metal complex catalyst contains at least one or more stable ligands attached to the transition metal.

10. The process of claim 8 wherein the multifunctional aryl allyl ether is conformationally restricted and the transition metal complex catalyst contains at least one or more stable ligands attached to the transition metal.

11. The process of claim 1 wherein the aryl allyl ether is the allyl ether of an aryl phenol.

12. The process of claim 1 wherein the aryl allyl ether has the structure represented by the following Formula I:

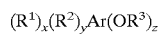

Formula I wherein x is from 0 to 750, y is from 0 to 750, z is from 1 to 150;

Ar is a moiety containing aromatic rings;

$R^1$ is a group substituted for a hydrogen atom at the positions that are ortho to the $OR^3$ group(s) on the aromatic ring(s) of the Ar moiety;

$R^2$ is a group substituted for a hydrogen atom at the positions that are not ortho to the $OR^3$ group(s) on the aromatic ring(s) of the Ar moiety;

$OR^3$ is a propenyl-containing oxy group substituted for a hydrogen atom on the aromatic ring(s) of the Ar moiety; and $R^3$ is a propenyl-containing group.

13. The process of claim 12 wherein Ar is a moiety selected from the group comprising a moiety containing a mononuclear aromatic ring; a moiety containing multinuclear aromatic rings; a moiety containing multinuclear fused aromatic rings; a moiety containing multinuclear fused aromatic rings with one or more heteroatoms; a moiety containing mononuclear or multinuclear aromatic ring(s) fused with a cycloaliphatic ring(s); a moiety containing mononuclear or multinuclear aromatic ring(s) fused with a cycloaliphatic ring(s) containing one or more heteroatoms selected from the group comprising O, N, S, Si, B, P and combinations thereof; and a group of aryl moieties in which each aryl moiety is connected to oligomeric or high molecular weight organosiloxane units.

14. The process of claim 12 wherein the aryl allyl ether has the structure represented by the following Formula II:

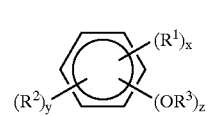

Formula II wherein x is 0 to 4, y is 0 to 3, and z is from 1 to 4;

$R^1$ is a group substituted for a hydrogen atom at the positions that are ortho to the $OR^3$ group(s) on the aromatic ring;

$R^2$ is a group substituted for a hydrogen atom at the positions that are not ortho to the $OR^3$ group(s) on the aromatic ring;

$OR^3$ is a propenyl-containing oxy group substituted for a hydrogen atom on the aromatic ring; and $R^3$ is a propenyl-containing moiety.

15. The process of claim 12 wherein the aryl allyl ether has the structure represented by the following Formula III:

Formula III

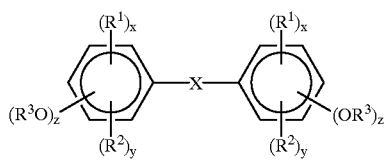

wherein x is 0 to 3, y is 0 to 2, z is from 1 to 2;

X is nil; a heteroatom; —C(O)—; —S(O$_2$)—; —C(O)—NH—; —P(O)Ar—; an organic aliphatic moiety, with or without heteroatoms; a cycloaliphatic group, with or without heteroatoms; an aromatic group, with or without heteroatoms; or any combination thereof;

$R^1$ is a group substituted for a hydrogen atom at the positions that are ortho to the $OR^3$ group(s) on the aromatic ring(s);

$R^2$ is a group substituted for a hydrogen atom at the positions that are not ortho to the $OR^3$ group(s) on the aromatic ring(s);

$OR^3$ is a propenyl-containing oxy group substituted for a hydrogen atom on the aromatic ring(s); and $R^3$ is a propenyl-containing moiety.

16. The process of claim 12 wherein the aryl allyl ether has the structure represented by the following Formula IV:

Formula IV

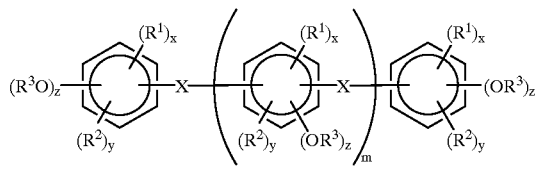

wherein x is 0 to 3, y is 0 to 2, z is from 1 to 2;
m is from 0.001 to 10;

X is nil; a heteroatom; —C(O)—; —S(O$_2$)—; —C(O)—NH—; —P(O)Ar—; an organic aliphatic moiety, with or without heteroatoms; a cycloaliphatic group, with or without heteroatoms; an aromatic group, with or without heteroatoms; or any combination thereof;

$R^1$ is a group substituted for a hydrogen atom at the positions that are ortho to the $OR^3$ group(s) on the aromatic ring(s);

$R^2$ is a group substituted for a hydrogen atom at the positions that are not ortho to the $OR^3$ group(s) on the aromatic ring(s);

$OR^3$ is a propenyl-containing oxy group substituted for a hydrogen atom on the aromatic ring(s); and $R^3$ is a propenyl-containing moiety.

17. The process of claim 12 wherein the aryl allyl ether has the structure represented by the following Formula V:

Formula V

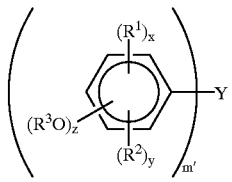

wherein x from is 0 to 3, y is from 0 to 3, z is from 1 to 2;

Y is an organic aliphatic moiety, with or without heteroatoms, having 1 to about 20 carbon atoms; a cycloaliphatic moiety, with or without heteroatoms, having 3 to 20 carbon atoms; an aromatic moiety, with or without heteroatoms, with no more than about 20 carbon atoms; or Y is an oligomeric or high molecular weight organosiloxane unit;

m' is from 3 or 4, or when Y is an oligomeric or high molecular weight organosiloxane unit, m' is from 1 to 150;

$R^1$ is a group substituted for a hydrogen atom at the positions that are ortho to the $OR^3$ group(s) on the aromatic ring;

$R^2$ is a group substituted for a hydrogen atom at the positions that are not ortho to the $OR^3$ group(s) on the aromatic ring;

$OR^3$ is a propenyl-containing oxy group substituted for a hydrogen atom on the aromatic ring(s); and $R^3$ is a propenyl-containing moiety.

18. The process of claims 12–17 wherein $R^1$ and $R^2$ are selected from a group consisting of a halogen; an alkyl group having from 1 to about 20 carbon atoms; a cycloaliphatic group having from 3 to about 20 carbon atoms; an aromatic group having from 6 to about 20 carbon atoms; or any combination thereof; wherein $R^1$ and $R^2$ can be different or the same.

19. The process of claim 18 wherein the alkyl group; the cycloaliphatic group; or the aromatic group contains one or more heteroatoms.

20. The process of claim 19 wherein the heteroatoms are selected from the group consisting of O, N, S, Si, B or P, or any combination of these heteroatoms with or without substituents thereon necessary to complete the bonding valence of the heteroatoms.

21. The process of claim 20 wherein $R^1$ and $R^2$ can be partially or fully fluorinated.

22. The process of claim 18 wherein $R^1$ is selected from the group consisting of methyl, ethyl, isopropyl, and halogen.

23. The process of claims 12–17 wherein $R^3$ is selected from the group consisting of:
—C($R^5$)$_2$C$R^5$=C($R^5$)$_2$, —C($R^5$)$_2$C($R^5$)$_2$C$R^5$=C($R^5$)$_2$ and

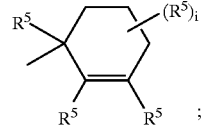

and a polyalkylene oxide group derived from ethylene oxide, propylene oxide, butylene oxide and cyclohexene oxide, terminated with one of the structures selected from the group comprising:
—C($R^5$)$_2$C$R^5$=C($R^5$)$_2$, —C($R^5$)$_2$C($R^5$)$_2$C$R^5$=C($R^5$)$_2$ and

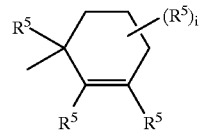

where $R^5$ is hydrogen; an alkyl group having 1 to about 20 carbon atoms; a cycloaliphatic group having from 3 to about 20 carbon atoms; or an aromatic group having from 6 to about 20 carbon atoms, wherein each individual $R^5$ is the same group or may be a different group from one another; and i is from 0 to 6.

24. The process of claim 23 wherein $R^3$ is selected from the group consisting of:

$-C(R^5)_2CR^5=C(R^5)_2$, $-C(R^5)_2C(R^5)_2CR^5=C(R^5)_2$ and

[structure: cyclohexene ring with $R^5$ substituents and $(R^5)_i$]

wherein $R^5$ is hydrogen, methyl, ethyl; wherein each individual $R^5$ is the same group or may be a different group from one another.

25. The process of claim 24 wherein $R^3$ is $-CH_2CH=CH_2$.

26. The process of claim 24 wherein $R^3$ is $-CH_2C(CH_3)=CH_2$.

27. The process of claim 24 wherein $R^3$ is

[structure: cyclohexene ring with H H labels]

28. The process of claim 12 wherein the aryl allyl ether is selected from the group comprising 2,6-dimethylphenyl allyl ether; 2,6-dimethylphenyl methallyl ether; 4-methyl-2,6-dibromophenyl allyl ether; 4-methyl-2,6-dibromophenyl methallyl ether; 1,4-, 1,5- or 2,6-naphthalene diallyl ethers; 1,4-, 1,5- or 2,6-naphthalene dimethallyl ethers; 4,4'-bisphenol A diallyl ether; 4,4'-(3,3',5,5'-tetramethyl) bisphenol A diallyl ether; 4,4'-(3,3',5,5'-tetrabromo) bisphenol A diallyl ether; 4,4'-(3,3',5,5'-tetramethyl-2,2',6,6'-tetrabromo)bisphenol A diallyl ether; 4,4'-(3,3',5,5'-tetramethyl)bisphenol F diallyl ether; 4,4'-bisphenol F diallyl ether; 4,4'-bisphenol sulfone diallyl ether; 4,4'-bisphenol K diallyl ether; 4,4'-(3,3'5,5'-tetramethyl-2,2',6,6'-tetrabromobiphenol)diallyl ether; 9,9-bis(4-allyloxyphenyl) fluorene; 4,4'-biphenol diallyl ether; 4,4'-(3,3',5,5'-tetramethylbiphenol)diallyl ether; 4,4'-diallyloxy-α-methylstilbene; 1,3-bis(4-allyloxyphenyl)adamantane; 4,4'-bisphenol A dimethallyl ether; 4,4'-(3,3',5,5'-tetramethyl) bisphenol A dimethallyl ether; 4,4'-(3,3',5,5'-tetrabromo) bisphenol A dimethallyl ether; 4,4'-(3,3',5,5'-tetramethyl-2,2',6,6'-tetrabromo)bisphenol A dimethallyl ether; 4,4'-(3,3',5,5'-tetramethyl)bisphenol F dimethallyl ether; 4,4'-bisphenol F dimethallyl ether; 4,4'-bisphenol sulfone dimethallyl ether; 4,4'-bisphenol K dimethallyl ether; 4,4'-(3,3',5,5'-tetramethyl-2,2',6,6'-tetrabromobiphenol) dimethallyl ether; 9,9-bis(4-methallyloxyphenyl)fluorene; 4,4'-biphenol dimethallyl ether; 4,4'-(3,3',5,5'-tetramethylbiphenol)dimethallyl ether; 4,4'-dimethallyloxy-α-methylstilbene; 1,3-bis(4-methallyloxyphenyl) adamantane; allyl ether of o-cresol-formaldehyde novolac (functionality>2); allyl ether of phenol-formaldehyde novolac (functionality>2); allyl ether of phenol-dicyclopentadienyl novolac (functionality>2); allyl ether of naphthol-formaldehyde novolac (functionality>2); methallyl ether of o-cresol-formaldehyde novolac (functionality>2); methallyl ether of phenol-formaldehyde novolac (functionality>2); methallyl ether of phenol-dicyclopentadienyl novolac (functionality>2); methallyl ether of naphthol-formaldehyde novolac (functionality>2); trisphenylol methane triallyl ether; tris(2,6-dimethylphenylol)methane triallyl ether; 1,1,2,2-tetraphenylol ethane tetraallyl ether; trisphenylol methane trimethallyl ether; tris(2,6-dimethylphenylol)methane trimethallyl ether; and 1,1,2,2-tetraphenylol ethane tetramethallyl ether.

29. The process of claim 28 wherein the aryl allyl ether is selected from the group consisting of 4,4'-bisphenol A diallyl ether; 4,4'-bisphenol A dimethallyl ether; 4,4'-(3,3',5,5'-tetramethyl)bisphenol A diallyl ether; 4,4'-(3,3',5,5'-tetramethyl)bisphenol A dimethallyl ether; 4,4'-(3,3',5,5'-tetrabromo)bisphenol A diallyl ether; 4,4'-(3,3',5,5'-tetrabromo)bisphenol A dimethallyl ether; 4,4'-(3,3',5,5'-tetramethyl-2,2',6,6'-tetrabromo)bisphenol A diallyl ether; 4,4'-(3,3',5,5'-tetramethyl-2,2',6,6'-tetrabromo)bisphenol A dimethallyl ether; 4,4'-bisphenol F diallyl ether; 4,4'-bisphenol F dimethallyl ether; 4,4'-(3,3',5,5'-tetramethyl) bisphenol F diallyl ether; 4,4'-(3,3',5,5'-tetramethyl) bisphenol F dimethallyl ether; 4,4'-(3,3',5,5'-tetramethylbiphenol)diallyl ether; and 4,4'-(3,3',5,5'-tetramethylbiphenol)dimethallyl ether.

30. The process of claim 1 wherein the hydroperoxide oxidant is aqueous hydrogen peroxide.

31. The process of claim 30 wherein the aqueous hydrogen peroxide contains 3 to 75% by weight of hydrogen peroxide.

32. The process of claim 1 wherein the hydroperoxide oxidant is an organic hydroperoxide having the following general structure:

$$R_b-\underset{\underset{R_c}{|}}{\overset{\overset{R_a}{|}}{C}}-OOH$$

where $R_a$, $R_b$, $R_c$ are the same or different and are selected from the group consisting of hydrogen, an alkyl group, a cycloaliphatic group, an aromatic group, or a combination thereof; or a combination of two or more of $R_a$, $R_b$, $R_c$ reside in the same structural unit.

33. The process of claim 32 wherein the organic oxidant is selected from the group consisting of t-butyl hydroperoxide and t-amyl hydroperoxide.

34. The process of claim 33 wherein the t-butyl hydroperoxide and t-amyl hydroperoxide are in inert organic solvent(s) or in water solution.

35. The process of claim 34 wherein the t-butyl hydroperoxide and t-amyl hydroperoxide solution contain from 3 to 75% organic hydroperoxide by weight.

36. The process of claim 1 wherein the transition metal complex catalyst has the following general structure:

$$[M^{+n}{}_s O_t (Q)_u (H)_v (L^1)_v (L^2)_v (L^3)_v (L^4)_v \ldots (L^p)_v]_w (G^1)_v (G^2)_v (G^3)_v (G^4)_v \ldots (G^p)_v$$

where M is a $d^o$ or $f^o$ transition metal element;

n is the oxidation state of metal M and n is 0 or an integer from 1 to 7;

s is an integer from 1 to 5;

O is the oxygen of a metal oxo moiety having the structure

M=O;

or O is the oxygen of M-μ-oxo- moiety having the structure

M—O—H or M—O—M t is an integer from 0 to 3;

Q is $O_2$ wherein O is oxygen and Q is a peroxo group bonded to metal M such that it forms a three-membered ring with one of the apexes being the metal atom M and the other two apexes being formed by the peroxo group as illustrated in the structure

u is an integer from 0 to 3;

H is a hydrogen atom bonded to the metal atom M having the structure

M—H or H is a hydrogen atom bonded to the oxygen of a metal-$\mu$-oxo moiety having the structure

M—O—H;

L, $L^1$, $L^2$, $L^3$, $L^4$, and $L^p$ are ligands up to a maximum number of p ligands;

$G^1$, $G^2$, $G^3$, $G^4$, and $G^p$ are counter cation groups to M—O$^-$ anions up to maximum number of p cations;

v is an integer from 0 to 10; and w is an integer from 1 to 10.

37. The process of claim 36 wherein the transition metal M is selected from the group consisting of Group IVa, Va, VIa and VIIa.

38. The process of claim 36 wherein the transition metal M is selected from the group consisting of Ti, Zr, V, Mo, W, Re and Mn.

39. The process of claim 36 wherein the transition metal M is Mo, W or Re.

40. The process of claim 36 wherein each of the ligands $L^1$, $L^2$, $L^3$, $L^4$ . . . $L^p$ can be either a strongly bonded, non-replaceable, neutral or basic, unidentate or multidentate ligand; or a labile, weakly bonded, neutral or basic, unidentate or multidentate ligand; or the combination thereof.

41. The process of claim 40 wherein the ligand is a multidentate ligand and is bonded to one same metal atom or to two or more different metal atoms.

42. The process of claim 40 wherein the ligands are linked onto an organic polymeric backbone, an inorganic polymeric backbone, or a hybrid inorganic-organic polymeric backbone.

43. The process of claim 36 wherein the ligands contain heteroatoms selected from the group consisting of O, N, S, Si, B, P or any combination of these heteroatoms.

44. The process of claim 36 wherein the ligand is a unidentate or multidentate ligand selected from the group consisting of oxygen-containing ligands, phosphorous-containing ligands, nitrogen-containing ligands, aromatic moiety-containing ligands, organosilyl-containing ligands, organosilyloxy-containing ligands, and a combination thereof.

45. The process of claim 36 wherein the ligands are partially or fully fluorinated.

46. The process of claim 36, wherein the ligand L contains one or more asymmetric centers or chiral centers in the ligand structure.

47. The process of claim 36 wherein the transition metal complex contains at least one or more stable ligands attached to the transition metal.

48. The process of claim 44 wherein the ligand is a bidentate or multidentate ligand selected from the group consisting of oxygen-containing ligands, phosphorous-containing ligands, nitrogen-containing ligands, aromatic moiety-containing ligands, organosilyl-containing, organosilyloxy-containing ligands, and a combination thereof.

49. The process of claim 36 wherein each of the counter cations $G^1$, $G^2$, $G^3$, $G^4$ . . . $G^p$ is an inorganic cation of Group Ia alkali metals.

50. The process of claim 36 wherein each of the Group Ia alkali metals counter cations is $Na^+$, $K^+$, or $Cs^+$.

51. The process of claim 36 wherein each of the counter cations $G^1$, $G^2$, $G^3$, $G^4$ . . . $G^p$ is an inorganic cation of Group IIa alkaline earth metals.

52. The process of claim 36 wherein each of the inorganic cations of Group IIa alkaline earth metals is $Mg^{++}$ or $Ca^{++}$.

53. The process of claim 36 wherein each of the counter cations $G^1$, $G^2$, $G^3$, $G^4$ . . . $G^p$ is an inorganic cation of Group IIIa metals.

54. The process of claim 36 wherein the inorganic cations of Group IIIa metals is $Al^{+++}$.

55. The process of claim 36 wherein each of the counter cations $G^1$, $G^2$, $G^3$, $G^4$ . . . $G^p$ is an organopnicogen-containing cation comprised of at least one pnicogen element of Group IVa and at least one organic substituent bonded to the pnicogen atom.

56. The process of claim 55 wherein each organopnicogen-containing cation is comprised of at least one or more quaternary cationic centers selected from the group consisting of nitrogen, phosphorous, arsenic, antimony, or bismuth.

57. The process of claim 55 wherein the organic substituent(s) bonded to the pnicogen atom is selected from the group consisting of C1–C20 aliphatic hydrocarbon, aromatic hydrocarbon, heterocyclic aliphatic or aromatic hydrocarbon, and halogen-containing aliphatic or aromatic hydrocarbon moieties.

58. The process of claim 55, wherein the organic substituents bonded to the pnicogen atom are on the backbone or side chain of an organic, inorganic or hybrid organic-inorganic oligomeric or polymeric structure.

59. The process of claim 58 wherein the organic substituents bonded to the pnicogen atoms are selected from the group consisting of C1–C20 aliphatic hydrocarbon, aromatic hydrocarbon, heterocyclic aliphatic or aromatic hydrocarbon moieties; and halogen-containing aliphatic or aromatic hydrocarbon moieties.

60. The process of claim 1 wherein the transition metal complex catalyst is a homogeneous catalyst.

61. The process of claim 1 wherein the transition metal complex catalyst is a heterogeneous catalyst.

62. The process of claim 61 wherein the transition metal complex catalyst is a transition metal complex of Ti, Zr, V, Mo, W, Re, Mn or any combination thereof.

63. The process of claim 62 wherein the transition metal complex catalyst is a transition metal complex of Mo, W, Re, Mn or a combination thereof.

64. The process of claim 1 wherein the transition metal complex catalyst is on a solid support.

65. The process of claim 64 wherein the transition metal complex catalyst is deposited onto the solid support.

66. The process of claim 64 wherein the transition metal complex catalyst is anchored onto the solid support through a condensation reaction between a reactive group on a ligand of a transition metal complex and a reactive group on the solid support.

67. The process of claim 66 wherein the transition metal complex catalyst is a transition metal complex of Ti, Zr, V, Mo, W, Re or Mn, or any combination thereof.

68. The process of claim 67 wherein the transition metal complex catalyst is a transition metal complex of Mo, W, Re or Mn, or a combination thereof.

69. The process of claim 64 wherein the transition metal complex catalyst is anchored onto the solid support through the formation of a strong, stable metal-ligand bond, wherein the ligand(s) is originally bound onto, or is part of, the constituents of the solid support.

70. The process of claim 69 wherein the transition metal complex catalyst is a transition metal complex of Ti, Zr, V, Mo, W, Re or Mn, or any combination thereof.

71. The process of claim 70 wherein the transition metal complex catalyst is a transition metal complex of Mo, W, Re or Mn, or a combination thereof.

72. The process of claim 71 wherein the transition metal complex catalyst is deposited onto, anchored onto, or encapsulated in a support which is selected from the group consisting of styrene-co-divinyl benzene based crosslinked polymers, ion exchange resins, aromatic polyimides, organosol gels, charcoals, carbons, silicas, aluminas, $Ba_2SO_4$, MgO, clays, silicates, zeolites, phosphites, aluminates, or the combination thereof.

73. The process of claim 1 wherein the aryl glycidyl ether is conformationally restricted.

74. The process of claim 2 wherein the aryl glycidyl ether is conformationally restricted due to the presence of atomic spacings which limit the mobility of the aryl glycidyl ether structure.

75. The process of claim 2 wherein the aryl glycidyl ether is conformationally restricted due to the presence of a rigid segment linking the aromatic rings, of which at least one is an aryl glycidyl ether moiety, which limits the mobility of the aryl glycidyl ether structure.

76. The process of claim 2 wherein the aryl glycidyl ether is conformationally restricted due to the presence of at least one substituent on the aromatic ring of the aryl glycidyl ether in a position ortho to the glycidyl ether group(s) which sterically hinders or restricts the freedom of rotation of the glycidyl ether group(s).

77. The process of claim 1 wherein the aryl glycidyl ether has the structure represented by the following Formula X:

$(R^1)_x(R^2)_yAr(OR^4)_z$           Formula X wherein x is 0 to 750, y is from 0 to 750, z is from 1 to 150;
Ar is a moiety containing aromatic ring(s);
$R^1$ is a group substituted for a hydrogen atom at the positions that are ortho to the $OR^4$ group(s) on the aromatic ring(s) of the Ar moiety;
$R^2$ is a group substituted for a hydrogen atom at the positions that are not ortho to the $OR^4$ group(s) on the aromatic ring(s) of the Ar moiety; and
$OR^4$ is a epoxide-containing oxy group substituted for a hydrogen on the aromatic ring(s) of the Ar moiety; and
$R^4$ is an epoxide-containing moiety.

78. The process of claim 77 wherein Ar is a moiety containing a mononuclear aromatic ring; a moiety containing multinuclear aromatic rings; a moiety containing multinuclear fused aromatic rings; a moiety containing multinuclear fused aromatic rings with one or more heteroatoms selected from the group comprising O, N, S, Si, B, P and combinations thereof; a moiety containing mononuclear or multinuclear aromatic ring(s) fused with a cycloaliphatic ring(s); a moiety containing mononuclear or multinuclear aromatic ring(s) fused with a cycloaliphatic ring(s) containing one or more heteroatoms; or a group of aryl moieties in which each aryl moiety is connected to oligomeric or high molecular weight organosiloxane units.

79. The process of claim 77 wherein the aryl glycidyl ether has the structure represented by the following Formula XI:

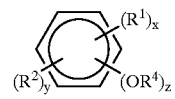

Formula XI wherein x is 0 to 4, y is 0 to 3, and z is from 1 to 4;
$R^1$ is a group substituted for a hydrogen atom at the positions that are ortho to the $OR^4$ group(s) on the aromatic ring(s);
$R^2$ is a group substituted for a hydrogen atom at the positions that are not ortho to the $OR^4$ group(s) on the aromatic ring(s);
$OR^4$ is an epoxide-containing oxy group substituted for a hydrogen on the aromatic ring(s); and
$R^4$ is an epoxide-containing moiety.

80. The process of claim 77 wherein the aryl glycidyl ether has the structure represented by the following Formula XII:

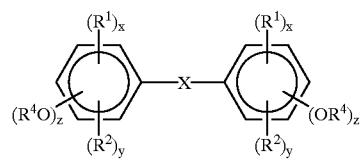

Formula XII wherein x is 0 to 3, y is 0 to 2, z is from 1 to 2;
X is nil; a heteroatom; —C(O)—; —S(O$_2$)—; —C(O)—NH—; —P(O)Ar—; an organic aliphatic moiety, with or without heteroatoms; a cycloaliphatic group, with or without heteroatoms; an aromatic group, with or without heteroatoms; or any combination thereof;
$R^1$ is a group substituted for a hydrogen atom at the positions that are ortho to the $OR^4$ group(s) on the aromatic ring(s);
$R^2$ is a group substituted for a hydrogen atom at the positions that are not ortho to the $OR^4$ group(s) on the aromatic ring;
$OR^4$ is an epoxide-containing oxy group substituted for a hydrogen on the aromatic ring(s); and
$R^4$ is an epoxide-containing moiety.

81. The process of claim 77 wherein the aryl glycidyl ether has the structure represented by the following Formula XIII:

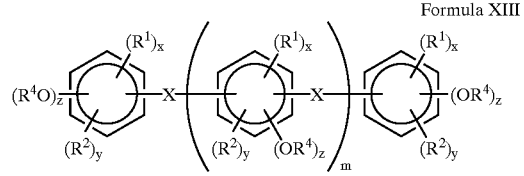

Formula XIII wherein x is 0 to 3, y is 0 to 2, z is from 1 to 2;
m is from 0.001 to 10;

X is nil; a heteroatom, —C(O)—; —S(O$_2$)—; —C(O)—NH—; —P(O)Ar—; an organic aliphatic moiety, with or without heteroatoms; a cycloaliphatic group, with or without heteroatoms; an aromatic group, with or without heteroatoms; or any combination thereof;

R$^1$ is a group substituted for a hydrogen atom at the positions that are ortho to the OR$^4$ group(s) on the aromatic ring(s);

R$^2$ is a group substituted for a hydrogen atom at the positions that are not ortho to the OR$^4$ group(s) on the aromatic ring(s);

OR$^4$ is a epoxide-containing oxy group substituted for a hydrogen on the aromatic ring(s); and R$^4$ is an epoxide-containing moiety.

82. The process of claim 77 wherein the glycidyl ether has the structure represented by the following Formula XIV:

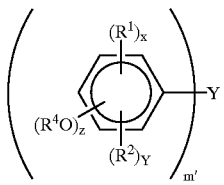

Formula XIV wherein x is 0 to 4, y is 0 to 4, z is from 1 to 3;

Y is an organic aliphatic moiety, with or without heteroatoms, having 1 to about 20 carbon atoms; a cycloaliphatic moiety, with or without heteroatoms, having 3 to about 20 carbon atoms; an aromatic moiety, with or without heteroatoms, with no more than about 20 carbon atoms; or Y is an oligomeric or high molecular weight organosiloxane unit;

m' is from 3 to 4, or when Y is an oligomeric or high molecular weight organosiloxane unit m' is from 1 to 150;

R$^1$ is a group substituted for a hydrogen atom at the positions that are ortho to the OR$^4$ group(s) on the aromatic ring(s);

R$^2$ is a group substituted for a hydrogen atom at the positions that are not ortho to the OR$^4$ group(s) on the aromatic ring(s);

OR$^4$ is a epoxide-containing oxy group substituted for a hydrogen on the aromatic ring(s); and R$^4$ is an epoxide-containing moiety.

83. The process of any one of claims 77, 79, 80, 81, and 82 wherein R$^4$ is selected from the group consisting of:

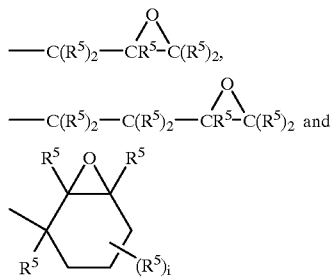

and a polyalkylene oxide group derived from ethylene oxide, propylene oxide, butylene oxide and cyclohexene oxide, terminated with the following structures selected from the group comprising:

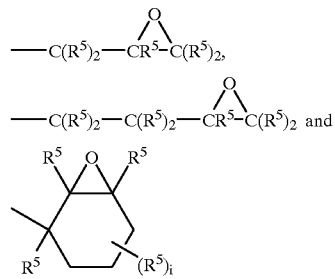

where R$^5$ is hydrogen; an alkyl group having 1 to about 20 carbon atoms; a cycloaliphatic group having from 3 to about 20 carbon atoms; or an aromatic group having from 6 to about 20 carbon atoms, wherein each individual R$^5$ is the same group or may be a different group from one another; and i is from 0 to 6.

84. The process of claim 83 wherein R$^4$ is a moiety selected from the group consisting of:

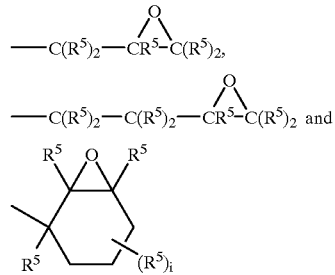

wherein R$^5$ is hydrogen, methyl, ethyl, wherein each individual R$^5$ is the same group or may be a different group from one another.

85. The process of claim 84 wherein R$^4$ is

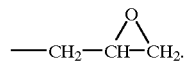

86. The process of claim 84 wherein R$^4$ is

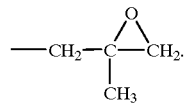

87. The process of claim 84 wherein R$^4$ is

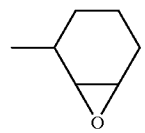

88. The process of claim 77 wherein the aryl glycidyl ether is selected from the group comprising 2,6-dimethylphenyl glycidyl ether; 2,6-dimethylphenyl methyl glycidyl ether; 4-methyl-2,6-dibromophenyl glycidyl ether; 4-methyl-2,6-dibromophenyl methyl glycidyl ether; 1,4-,1,5- or 2,6-naphthalene diglycidyl ethers; 4,4'-bisphenol A diglycidyl ether; 4,4'-(3,3',5,5'-tetramethyl)bisphenol A diglycidyl ether; 4,4'-(3,3',5,5'-tetrabromo)bisphenol A diglycidyl ether; 4,4'-(3,3',5,5'-tetramethyl-2,2',6,6'-tetrabromo) bisphenol A diglycidyl ether; 4,4'-(3,3',5,5'-tetramethyl) bisphenol F diglycidyl ether; 4,4'-bisphenol F diglycidyl ether; 4,4'-bisphenol sulfone diglycidyl ether; 4,4'-bisphenol K diglycidyl ether; 4,4'-(3,3',5,5'-tetramethyl-2,2',6,6'-tetrabromobiphenol)diglycidyl ether; 9,9-bis(4-glycidyloxyphenyl)fluorene; 4,4'-biphenol diglycidyl ether; 4,4'-(3,3',5,5'-tetramethylbiphenol)diglycidyl ether; 4,4'-dihydroxy-α-methylstilbene diglycidyl ether; 1,3-bis(4-glycidyloxyphenyl)adamantane; 4,4'-bisphenol A dimethylglycidyl ether; 4,4'-(3,3',5,5'-tetramethyl)bisphenol A dimethylglycidyl ether; 4,4'-(3,3',5,5'-tetrabromo)bisphenol A dimethylglycidyl ether; 4,4'-(3,3',5,5'-tetramethyl-2,2',6,6'-tetrabromo)bisphenol A dimethylglycidyl ether; 4,4'-(3,3',5,5'-tetramethyl)bisphenol F dimethylglycidyl ether; 4,4'-bisphenol F dimethylglycidyl ether; 4,4'-bisphenol sulfone dimethylglycidyl ether; 4,4'-bisphenol K dimethylglycidyl ether; 4,4'-(3,3'5,5'-tetramethyl-2,2',6,6'-tetrabromobiphenol)dimethylglycidyl ether; 9,9-bis(4-methylglycidyloxyphenyl)fluorene; 4,4'-biphenol dimethylglycidyl ether; 4,4'-(3,3',5,5'-tetramethylbiphenol) dimethylglycidyl ether; 4,4'-dihydroxy-α-methylstilbene dimethylglycidyl ether; 1,3-bis(4-methylglycidyloxyphenyl)adamantane; glycidyl ether of o-cresol-formaldehyde novolac (functionality>2); glycidyl ether of phenol-formaldehyde novolac (functionality>2); glycidyl ether of phenol-dicyclopentadienyl novolac (functionality>2); glycidyl ether of naphthol-formaldehyde novolac (functionality>2); methyl glycidyl ether of o-cresol-formaldehyde novolac (functionality>2); methyl glycidyl ether of phenol-formaldehyde novolac (functionality>2); methyl glycidyl ether of phenol-dicyclopentadienyl novolac (functionality>2); methyl glycidyl ether of naphthol-formaldehyde novolac (functionality>2); trisphenylol methane triglycidyl ether; tris(2,6-dimethylphenylol)methane triglycidyl ether; 1,1,2,2-tetraphenylol ethane tetraglycidyl ether; trisphenylol methane trimethyl glycidyl ether; tris(2,6-dimethylphenylol)methane trimethyl glycidyl ether; and 1,1,2,2-tetraphenylol ethane tetramethyl glycidyl ether.

89. The process of claim 88 wherein the aryl glycidyl ether is selected from the group consisting of 4,4'-bisphenol A diglycidyl ether; 4,4'-bisphenol a dimethyl glycidyl ether; 4,4'-(3,3',5,5'-tetramethyl)bisphenol A diglycidyl ether; 4,4'-(3,3',5,5'-tetramethyl)bisphenol A dimethyl glycidyl ether; 4,4'-(3,3',5,5'-tetrabromo)bisphenol A diglycidyl ether; 4,4'-(3,3',5,5'-tetrabromo)bisphenol A dimethyl glycidyl ether; 4,4'-(3,3',5,5'-tetramethyl-2,2',6,6'-tetrabromo)bisphenol A diglycidyl ether; 4,4'-(3,3',5,5'-tetramethyl-2,2',6,6'-tetrabromo)bisphenol A dimethyl glycidyl ether; 4,4'-bisphenol F dimethyl glycidyl ether; 4,4'-bisphenol F dimethyl glycidyl ether; 4,4'-(3,3',5,5'-tetramethyl)bisphenol F diglycidyl ether; 4,4'-(3,3',5,5'-tetramethyl)bisphenol F dimethyl glycidyl ether; 4,4'-(3,3',5,5'-tetramethylbiphenol) diglycidyl ether; and 4,4'-(3,3',5,5'-tetramethylbiphenol) dimethyl glycidyl ether.

90. The process of claim 1 wherein the reaction is carried out at a temperature of from about 0° C. to about 120° C.

91. The process of claim 90 wherein the reaction is carried out at a temperature of from about 10° C. to about 100° C.

92. The process of claim 1 wherein the reaction is carried out at atmospheric pressure, sub-atmospheric pressure or super-atmospheric pressure.

93. The process of claim 1 including a solvent present in the reaction mixture.

94. The process of claim 93 wherein the solvent is selected from the group consisting of aliphatic, cycloaliphatic or aromatic hydrocarbon solvents; partially or fully halogenated aliphatic, cycloaliphatic or aromatic hydrocarbon solvents; aliphatic, cycloaliphatic or aromatic alcohols or nitriles; partially or fully fluorinated aliphatic, cycloaliphatic or aromatic alcohol solvents; $CO_2$ and combinations thereof.

95. The process of claim 60 wherein the molar ratio of the catalyst to aryl allyl ether present in a reaction mixture is from about $1 \times 10^{-6}$ to about 1 mole of catalyst per 1 mole of aryl allyl ether.

96. The process of claim 95 wherein the molar ratio of the catalyst to aryl allyl ether present in the reaction mixture is from about $1 \times 10^{-6}$ to about $1 \times 10^{-1}$ mole of catalyst per 1 mole of aryl allyl ether.

97. The process of claim 96 wherein the molar ratio of the catalyst to aryl allyl ether present in the reaction mixture is from about $1 \times 10^{-6}$ to about $1 \times 10^{-2}$ mole of catalyst per 1 mole of aryl allyl ether.

98. The process of claim 64 wherein the total weight of the metal in the catalyst complex to the total weight of the solid support material is in the range of from about $1 \times 10^{-6}$ part to about 1 part of metal per 1 part of solid support.

99. The process of claim 98 wherein the total weight of the metal in the catalyst complex to the total weight of the solid support material is in the range of from about $1 \times 10^{-6}$ part to $1 \times 10^{-1}$ part of metal per about 1 part of solid support.

100. The process of claim 99 wherein the total weight of the metal in the catalyst complex to the total weight of the solid support material is in the range of from about $1 \times 10^{-6}$ part to about $1 \times 10^{-2}$ part of metal per 1 part of solid support.

101. The process of claim 64 wherein the weight ratio of heterogeneous catalyst to substrate aryl allyl ether is in the range of from about 100 parts to about 10 parts of heterogeneous catalyst to 1 part of aryl allyl ether.

102. The process of claim 101 wherein the weight ratio of heterogeneous catalyst to substrate aryl allyl ether is in the range of from about 100 parts to about 1 part of heterogeneous catalyst to 1 part of aryl allyl ether.

103. The process of claim 102 wherein the weight ratio of heterogeneous catalyst to substrate aryl allyl ether is in the range of from about 100 parts to about $1 \times 10^{-3}$ part of heterogeneous catalyst to 1 part of aryl allyl ether.

104. The process of claim 32 wherein the molar ratio of oxidant to allyl ether is from about 0.6 mole to about 20 moles to 1 equivalent of aryl allyl ether.

105. A product made by the process of claim 1.

106. A composition comprising a reaction mixture of:

(A) an aryl allyl ether, (B) a hydroperoxide oxidant, and (C) a transition metal complex catalyst, wherein at least (a) the aryl allyl ether is conformationally restricted; or (b) the transition metal complex catalyst contains at least one or more stable ligands attached to the transition metal.

* * * * *